US010654825B2

(12) United States Patent
By et al.

(10) Patent No.: US 10,654,825 B2
(45) Date of Patent: May 19, 2020

(54) PROCESSES FOR MAKING TRIAZOLO[4,5D] PYRAMIDINE DERIVATIVES AND INTERMEDIATES THEREOF

(71) Applicant: Corvus Pharmaceuticals, Inc., Burlingame, CA (US)

(72) Inventors: Kolbot By, San Ramon, CA (US); William Benton Jones, Oakland, CA (US); Bradley Hamilton Wolfe, Pacifica, CA (US)

(73) Assignee: CORVUS PHARMACEUTICALS, INC., Burlingame, CA (US)

( * ) Notice: Subject to any disclaimer, the term of this patent is extended or adjusted under 35 U.S.C. 154(b) by 0 days.

(21) Appl. No.: 15/942,362

(22) Filed: Mar. 30, 2018

(65) Prior Publication Data
US 2018/0290999 A1    Oct. 11, 2018

Related U.S. Application Data

(60) Provisional application No. 62/479,235, filed on Mar. 30, 2017.

(51) Int. Cl.
| | | |
|---|---|---|
| *C07D 401/12* | (2006.01) | |
| *C07D 487/04* | (2006.01) | |
| *C07D 405/12* | (2006.01) | |
| *C07D 487/18* | (2006.01) | |
| *C07D 405/14* | (2006.01) | |

(52) U.S. Cl.
CPC ......... *C07D 401/12* (2013.01); *C07D 405/12* (2013.01); *C07D 405/14* (2013.01); *C07D 487/04* (2013.01); *C07D 487/18* (2013.01)

(58) Field of Classification Search
CPC .. C07D 401/12; C07D 405/12; C07D 405/14; C07D 487/04; C07D 487/18
See application file for complete search history.

(56) References Cited

U.S. PATENT DOCUMENTS

| | | | |
|---|---|---|---|
| 5,242,890 A * | 9/1993 | Cho | A01N 43/82 504/100 |
| 6,156,756 A | 12/2000 | Hardern et al. | |
| 7,589,097 B2 | 9/2009 | Gillespie et al. | |
| 8,450,328 B2 * | 5/2013 | Bamford | C07D 405/12 514/261.1 |
| 9,376,443 B2 | 6/2016 | Bamford et al. | |
| 10,138,212 B2 * | 11/2018 | Ali | C07D 401/14 |

FOREIGN PATENT DOCUMENTS

| | | | | |
|---|---|---|---|---|
| WO | WO-2007092496 A2 * | 8/2007 | ......... | A61K 38/1709 |
| WO | WO-2009156737 A1 * | 12/2009 | ........... | C07D 487/04 |

OTHER PUBLICATIONS

M. Li et al., 5 Bioconjugate Chemistry, 454-458 (1994).*
N.G. Anderson, Practical Process Research and Development (2nd ed., 2000) (Year: 2000).*

* cited by examiner

*Primary Examiner* — Alexander R Pagano
(74) *Attorney, Agent, or Firm* — Mintz, Levin, Cohn, Ferris, Glovsky and Popeo, P.C.; Irina E Britva

(57) ABSTRACT

Provided herein are, inter alia, methods for making triazolo [4,5]pyramidine derivatives and intermediates thereof that are useful for treating diseases.

57 Claims, No Drawings

PROCESSES FOR MAKING TRIAZOLO[4,5D] PYRAMIDINE DERIVATIVES AND INTERMEDIATES THEREOF

CROSS-REFERENCES TO RELATED APPLICATIONS

This application claims the benefit of U.S. Provisional Patent Application No. 62/479,235 filed Mar. 30, 2017, which is incorporated herein by reference in its entirety.

FIELD OF THE INVENTION

The present disclosure relates to improved methods for making triazolo[4,5]pyramidine derivatives and intermediates thereof.

BACKGROUND OF THE INVENTION

Processes for making triazolo[4,5]pyramidine derivatives and intermediates thereof have been previously described. Such processes, however, often yield products that contain unacceptable levels of residual palladium. Moreover, such processes are not economical when manufacturing commercial quantities. Accordingly, it would be desirable to provide a process for the production of triazolo[4,5]pyramidine derivatives and intermediates thereof having acceptable levels of palladium and that are economically efficient for commercial scale-up. Provided herein are solutions to those and other challenges in the art.

BRIEF SUMMARY OF THE INVENTION

In an aspect, there is provided a precipitate of formula (I):

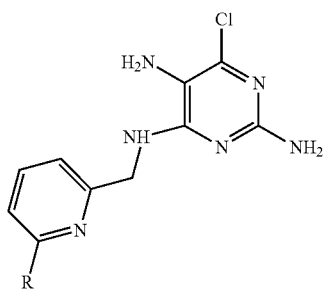

(I)

or a tautomer, stereoisomer, or pharmaceutically acceptable salt thereof, wherein:

R is —(CR$^a$R$^b$)—O—R$^2$;

R$^a$ is H or alkyl;

R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocyclic ring comprising a ring member selected from O, N(R$^3$) and S;

R$^2$ is H, alkyl, cycloalkyl or heterocycloalkyl, wherein the alkyl or cycloalkyl may optionally be substituted with halo, alkoxy or heterocycloalkyl;

R$^3$ is H or alkyl;

wherein, heteroaryl is a 5 or 6 membered aromatic ring, comprising one or two ring members selected from N, N(R$^4$), S and O;

alkyl (or the alkyl group of the alkoxy group) is a linear or branched saturated hydrocarbon containing up to 10 carbon atoms;

alkoxy is a linear or branched saturated hydrocarbon containing up to 10 carbon atoms attached to the remainder of the molecule through an oxygen linker;

heterocycloalkyl is a C-linked or N-linked 3 to 10 membered non-aromatic, monocyclic ring, wherein said heterocycloalkyl ring comprises 1, 2 or 3 ring members independently selected from N, N(R$^4$), S(O)$_q$ and O;

R$^4$ is H or alkyl; and q is 0, 1 or 2.

In another aspect, there is provided a compound of formula (II):

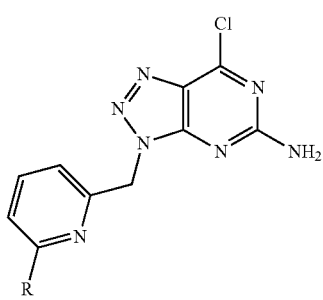

(II)

or a tautomer, stereoisomer, or pharmaceutically acceptable salt thereof, wherein:

R is —(CR$^a$R$^b$)—O—R$^2$;

R$^a$ is H or alkyl;

R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocyclic ring comprising a ring member selected from O, N(R$^3$) and S;

R$^2$ is H, alkyl, cycloalkyl or heterocycloalkyl, wherein said alkyl or cycloalkyl may optionally be substituted with halo, alkoxy or heterocycloalkyl;

R$^3$ is H or alkyl;

wherein, heteroaryl is a 5 or 6 membered aromatic ring, comprising one or two ring members selected from N, N(R$^4$), S and O;

alkyl (or the alkyl group of the alkoxy group) is a linear or branched saturated hydrocarbon containing up to 10 carbon atoms;

alkoxy is a linear or branched saturated hydrocarbon containing up to 10 carbon atoms attached to the remainder of the molecule through an oxygen linker;

heterocycloalkyl is a C-linked or N-linked 3 to 10 membered non-aromatic, monocyclic ring, wherein said heterocycloalkyl ring comprises 1, 2 or 3 ring members independently selected from N, N(R$^4$), S(O)$_q$ and O;

R$^4$ is H or alkyl; and q is 0, 1 or 2.

In another aspect, there is provided a method of isolating a precipitate of formula (I):

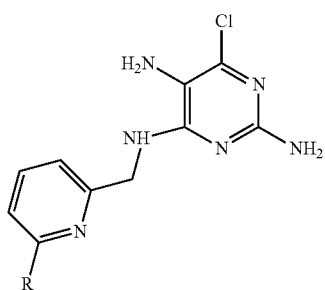

(I)

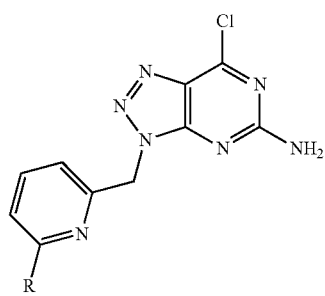

(II)

comprising the steps of:
(a) reacting a compound of the formula:

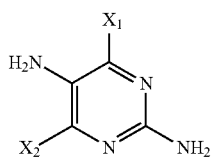

with a compound of the formula:

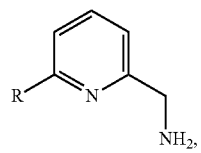

in the presence of a base;
wherein,
$X_1$ and $X_2$ are independently halo, and
wherein R is $—(CR^aR^b)—O—R^2$;
$R^a$ is H or alkyl;
$R^b$ is H or alkyl; or $R^a$ and $R^b$ together with the atom to which they are attached form a 3 to 8 membered saturated or partially saturated hydrocarbon ring or form a 4 to 8 membered saturated or partially saturated heterocyclic ring comprising a ring member selected from O, $N(R^3)$ and S;
$R^2$ is H, alkyl, cycloalkyl or heterocycloalkyl, wherein said alkyl or cycloalkyl may optionally be substituted with halo, alkoxy or heterocycloalkyl;
$R^3$ is H or alkyl;
wherein, heteroaryl is a 5 or 6 membered aromatic ring, comprising one or two ring members selected from N, $N(R^4)$, S and O;
alkyl (or the alkyl group of the alkoxy group) is a linear or branched saturated hydrocarbon containing up to 10 carbon atoms;
alkoxy is a linear or branched saturated hydrocarbon containing up to 10 carbon atoms attached to the remainder of the molecule through an oxygen linker;
heterocycloalkyl is a C-linked or N-linked 3 to 10 membered non-aromatic, monocyclic ring, wherein said heterocycloalkyl ring comprises 1, 2 or 3 ring members independently selected from N, $N(R^4)$, $S(O)_q$ and O;
$R^4$ is H or alkyl; and
q is 0, 1 or 2; and
(b) isolating the precipitate of formula (I).
In another aspect, the method comprises the step of forming a compound of formula (II):

wherein R is as defined above, by:
(a) reacting the precipitate of formula (I) with a nitrite; and
(b) isolating the compound of formula (II).
In another aspect, the method comprises the step of forming a compound of formula (III):

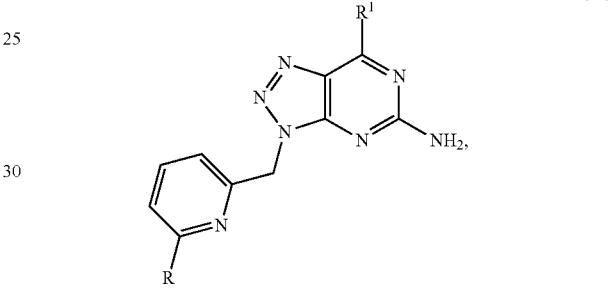

by:
(a) reacting a compound of formula (II) with a compound of the formula $R^1—Y$ in the presence of a palladium catalyst and a base, wherein Y is a leaving group,
wherein, R is $—(CR^aR^b)—O—R^2$;
$R^a$ is H or alkyl;
$R^b$ is H or alkyl; or $R^a$ and $R^b$ together with the atom to which they are attached form a 3 to 8 membered saturated or partially saturated hydrocarbon ring or form a 4 to 8 membered saturated or partially saturated heterocylic ring comprising a ring member selected from O, $N(R^3)$ and S;
$R^1$ is phenyl or heteroaryl, wherein said phenyl or said heteroaryl group may be optionally substituted with alkyl, alkoxy, halo or —CN;
$R^2$ is H, alkyl, cycloalkyl or heterocycloalkyl, wherein said alkyl or cycloalkyl may optionally be substituted with halo, alkoxy or heterocycloalkyl;
$R^3$ is H or alkyl;
wherein, heteroaryl is a 5 or 6 membered aromatic ring, comprising one or two ring members selected from N, $N(R^4)$, S and O;
alkyl (or the alkyl group of the alkoxy group) is a linear or branched saturated hydrocarbon containing up to 10 carbon atoms;
alkoxy is a linear or branched saturated hydrocarbon containing up to 10 carbon atoms attached to the remainder of the molecule through an oxygen linker;
heterocycloalkyl is a C-linked or N-linked 3 to 10 membered non-aromatic, monocyclic ring, wherein said heterocycloalkyl ring comprises 1, 2 or 3 ring members independently selected from N, $N(R^4)$, $S(O)_q$ and O;

$R^4$ is H or alkyl; and
q is 0, 1 or 2; and
(b) isolating the compound of formula (III).

In another aspect, there is provided a precipitate of formula (IV):

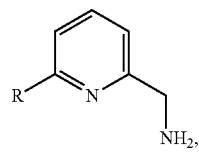
(IV)

or a hydrate, tautomer, stereoisomer, or pharmaceutically acceptable salt thereof, wherein:

R is —(CR$^a$R$^b$)—O—R$^2$;

R$^a$ is H or alkyl;

R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocylic ring comprising a ring member selected from O, N(R$^3$) and S;

R$^2$ is H, alkyl, cycloalkyl or heterocycloalkyl, wherein the alkyl or cycloalkyl may optionally be substituted with halo, alkoxy or heterocycloalkyl;

R$^3$ is H or alkyl;

wherein:

heteroaryl is a 5 or 6 membered aromatic ring, comprising one or two ring members selected from N, N(R$^4$), S and O;

alkyl (or the alkyl group of the alkoxy group) is a linear or branched saturated hydrocarbon containing up to 10 carbon atoms;

alkoxy is a linear or branched saturated hydrocarbon containing up to 10 carbon atoms attached to the remainder of the molecule through an oxygen linker;

heterocycloalkyl is a C-linked or N-linked 3 to 10 membered non-aromatic, monocyclic ring, wherein said heterocycloalkyl ring comprises 1, 2 or 3 ring members independently selected from N, N(R$^4$), S(O)$_q$ and O; and R$^4$ is H or alkyl.

In another aspect, there is provided a compound of formula (V):

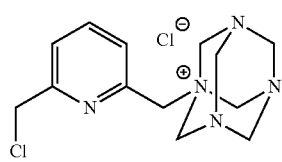
(V)

In another aspect, provided is a method of forming the compound of formula (V):

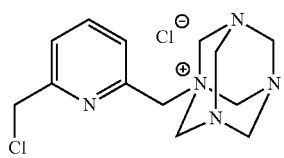 [SMILES: ClCc1cccc(C[N+]23CN4CN(CN(C4)C2)C3)n1 ; [Cl-]]

comprising the step of reacting the compound of formula:

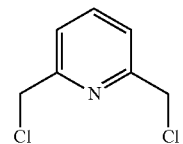

with hexamethylenetetraamine (HMTA) of formula:

In another aspect, provided is a compound of formula (VII):

(VII)

In another aspect, provided is a method of forming the compound of formula (VII):

(VII)

comprising the step of reacting the compound of formula:

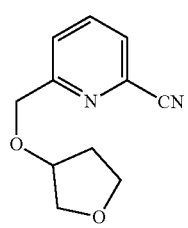 [SMILES: N#Cc1cccc(COC2CCOC2)n1]

with a methylating agent.

These and other aspects of the present disclosure will become apparent from the following description of the preferred embodiment taken in conjunction with the following drawings, although variations and modifications therein may be affected without departing from the spirit and scope of the novel concepts of the disclosure.

DETAILED DESCRIPTION OF THE INVENTION

Definitions

While various embodiments and aspects of the present disclosure are shown and described herein, it will be obvious to those skilled in the art that such embodiments and aspects are provided by way of example only. Numerous variations, changes, and substitutions will now occur to those skilled in the art without departing from the disclosure. It should be understood that various alternatives to the embodiments of the disclosure described herein may be employed in practicing the disclosure.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present disclosure. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched non-cyclic chain, or combinations thereof, including at least one carbon atom and at least one heteroatom (e.g. O, N, P, Si, and S), and wherein the nitrogen and sulfur atoms may optionally be oxidized, and the nitrogen heteroatom may optionally be quaternized. The heteroatom(s) (e.g. O, N, P, S, and Si) may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl"

and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The term alkoxy is a linear or branched saturated hydrocarbon containing up to 10 carbon atoms attached to the remainder of the molecule through an oxygen linker.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$—$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl", "heteroalkyl", "cycloalkyl", "heterocycloalkyl", "aryl", and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the disclosure includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the disclosure includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present disclosure. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present disclosure may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject).

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

As used herein, the term "salt" refers to acid or base salts of the compounds used in the methods of the present disclosure. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms.

Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

The symbol "$\sim$" denotes the point of attachment of a chemical moiety to the remainder of a molecule or chemical formula.

In embodiments, a compound as described herein may include multiple instances of $R^2$ and/or other variables. In such embodiments, each variable may optional be different and be appropriately labeled to distinguish each group for greater clarity. For example, where each $R^2$ is different, they may be referred to, for example, as $R^{2.1}$, $R^{2.2}$, $R^{2.3}$, and/or $R^{2.4}$ respectively, wherein the definition of $R^2$ is assumed by $R^{2.1}$, $R^{2.2}$, $R^{2.3}$, and/or $R^{2.4}$. The variables used within a definition of $R^2$ and/or other variables that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{12}$-substituted or unsubstituted alkyl, a plurality of $R^{12}$ substituents may be attached to the alkyl moiety wherein each $R^{12}$ substituent is optionally different. Where an R-substituted moiety is substituted with a plurality R substituents, each of the R-substituents may be differentiated herein using a prime symbol (') such as R', R'', etc. For example, where a moiety is $R^{12}$-substituted or unsubstituted alkyl, and the moiety is substituted with a plurality of $R^{12}$ substituents, the plurality of $R^{12}$ substituents may be differentiated as $R^{12'}$, $R^{12''}$, $R^{12'''}$, etc. In embodiments, the plurality of R substituents is 3. In embodiments, the plurality of R substituents is 2.

In embodiments, a compound as described herein may include multiple instances of $R^1$, $R^2$, $R^3$, $R^4$, $R^5$, $R^6$, $R^7$, $R^9$, $R^{10}$, $R^{11}$, $R^{12}$, $R^{13}$, $R^{14}$ and/or other variables. In such embodiments, each variable may optional be different and be appropriately labeled to distinguish each group for greater clarity. For example, where each $R^1$, $R^2$, $R^3$, $R^4$, $R^5$, $R^6$, $R^7$, $R^9$, $R^{10}$, $R^{11}$, $R^{12}$, $R^{13}$, and/or $R^{14}$, is different, they may be referred to, for example, as $R^{1.1}$, $R^{1.2}$, $R^{1.3}$, $R^{1.4}$, $R^{2.1}$, $R^{2.2}$, $R^{2.3}$, $R^{2.4}$, $R^{3.1}$, $R^{3.2}$, $R^{3.3}$, $R^{3.4}$, $R^{4.1}$, $R^{4.2}$, $R^{4.3}$, $R^{4.4}$, $R^{5.1}$, $R^{5.2}$, $R^{5.3}$, $R^{5.4}$, $R^{6.1}$, $R^{6.2}$, $R^{6.3}$, $R^{6.4}$, $R^{7.1}$, $R^{7.2}$, $R^{7.3}$, $R^{7.4}$, $R^{9.1}$, $R^{9.2}$, $R^{9.3}$, $R^{9.4}$, $R^{10.1}$, $R^{10.2}$, $R^{10.3}$, $R^{10.4}$, $R^{11.1}$, $R^{11.2}$, $R^{11.3}$, $R^{11.4}$, $R^{12.1}$, $R^{12.2}$, $R^{12.3}$, $R^{12.4}$, $R^{13.1}$, $R^{13.2}$, $R^{13.3}$, $R^{13.4}$, $R^{14.1}$, $R^{14.2}$, $R^{14.3}$, and/or $R^{14.4}$, respectively, wherein the definition of $R^1$ is assumed by $R^{1.1}$, $R^{1.2}$, $R^{1.3}$, and/or $R^{1.4}$, the definition of $R^2$ is assumed by $R^{2.1}$, $R^{2.2}$, $R^{2.3}$, and/or $R^{2.4}$, the definition of $R^3$ is assumed by $R^{3.1}$, $R^{3.2}$, $R^{3.3}$, and/or $R^{3.4}$, the definition of $R^4$ is assumed by $R^{4.1}$, $R^{4.2}$, $R^{4.3}$, and/or $R^{4.4}$, the definition of $R^5$ is assumed by $R^{5.1}$, $R^{5.2}$, $R^{5.3}$, and/or $R^{5.4}$, the definition of $R^6$ is assumed by $R^{6.1}$, $R^{6.2}$, $R^{6.3}$, and/or $R^{6.4}$, the definition of $R^7$ is assumed by $R^{7.1}$, $R^{7.2}$, $R^{7.3}$, and/or $R^{7.4}$, the definition of $R^9$ is assumed by $R^{9.1}$, $R^{9.2}$, $R^{9.3}$, and/or $R^{9.4}$, the definition of $R^{10}$ is assumed by $R^{10.1}$, $R^{10.2}$, $R^{10.3}$, and/or $R^{10.4}$, the definition of $R^{11}$ is assumed by $R^{11.1}$, $R^{11.2}$, $R^{11.3}$, and/or $R^{11.4}$, the definition of $R^{12}$ is assumed by $R^{12.1}$, $R^{12.2}$, $R^{12.3}$, and/or $R^{12.4}$, the definition of $R^{13}$ is assumed by $R^{13.1}$, $R^{13.2}$, $R^{13.3}$, and/or $R^{13.4}$, the definition of $R^{14}$ is assumed by $R^{14.1}$, $R^{14.2}$, $R^{14.3}$, and/or $R^{14.4}$. The variables used within a definition of $R^1$, $R^2$, $R^3$, $R^4$, $R^5$, $R^6$, $R^7$, $R^9$, $R^{10}$, $R^{11}$, $R^{12}$, $R^{13}$ and/or $R^{14}$, and/or other variables that appear at multiple instances and are different may similarly be appropriately labeled to distinguish each group for greater clarity.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a pharmaceutical composition as provided herein and a cell or a pCREB detection agent as described herein and a pCREB antigen. In embodiments contacting includes, for example, allowing a pharmaceutical composition as described herein to interact with a cell or a patient. In further embodiments, contacting includes, for example, allowing a pCREB detection agent as described herein to interact with a pCREB antigen.

As defined herein, the term "inhibition", "inhibit", "inhibiting" and the like in reference to a protein-inhibitor (e.g., an A2A receptor antagonist or a PD-1 signaling pathway inhibitor) interaction means negatively affecting (e.g., decreasing) the activity or function of the protein (e.g., decreasing the activity of an A2A receptor or a PD-1 protein or PD-L1 protein) relative to the activity or function of the protein in the absence of the inhibitor (e.g., an A2A receptor antagonist or a PD-1 signaling pathway inhibitor). In some embodiments, inhibition refers to reduction of a disease or symptoms of disease (e.g., cancer). Thus, inhibition includes, at least in part, partially or totally blocking stimulation, decreasing, preventing, or delaying activation, or inactivating, desensitizing, or down-regulating signal transduction or enzymatic activity or the amount of a protein (e.g., an A2A receptor or a PD-1 protein or PD-L1 protein). Similarly an "inhibitor" is a compound or protein that inhibits an A2A receptor or a PD-1 protein or PD-L1 protein, e.g., by binding, partially or totally blocking, decreasing, preventing, delaying, inactivating, desensitizing, or down-regulating activity (e.g., an A2A receptor activity or a PD-1 protein activity or PD-L1 protein activity).

An "anti-cancer agent" is a therapeutic used in the treatment or prevention of cancer. An anti-cancer agent can be a large or small molecule. Example anti-cancer agents include antibodies, small molecules, and large molecules or combinations thereof.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds or platinum containing agents (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec.®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-nl; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol.™ (i.e. paclitaxel), Taxotere.™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), Vincristine sulfate, Cryptophycin 52 (i.e. LY-355703), Vitilevuamide, Tubulysin A, Canadensol, Centaureidin (i.e. NSC-106969), Oncocidin A1 (i.e. BTO-956 and DIME), Fijianolide B, Laulimalide, Narcosine (also known as NSC-5366), Nascapine, Hemiasterlin, Vanadocene acetylacetonate, Monsatrol, lnanocine (i.e. NSC-698666), Eleutherobins (such as Desmethyl eleutherobin, Desaetyleleutherobin, Isoeleutherobin A, and Z-Eleutherobin), Caribaeoside, Caribaeolin, Halichondrin B, Diazonamide A, Taccalonolide A, Diozostatin, (-)-Phenylahistin (i.e. NSCL-96F037), Myoseverin B, Resverastatin phosphate sodium, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{11}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, hormonal therapies, or the like.

"Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound. In embodiments, an analog is an adenosine analog.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

As used herein, the terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). The disease may be an autoimmune, inflammatory, cancer, infectious, metabolic, developmental, cardiovascular, liver, intestinal, endocrine, neurological, or other disease.

As used herein, the term "nitrite" refers to a nitrite compound which is either a salt or an ester of nitrous acid As used herein, the terms "boronic acid moiety" and "boronic ester moiety" refer to a compound related to boric acid in which one of the three hydroxyl groups is replaced by an alkyl or aryl group, or contains an ester moiety.

As used herein, the term "organometallic leaving group" refers to a moiety contemplating zinc, silate, tin, or boron moieties.

As used herein, the term "palladium complex' refers to organic palladium compounds that are used as catalysts in the reduction of alkenes and alkynes with hydrogen. This process involves the formation of a palladium-carbon covalent bond. Palladium complexes are also used in carbon-carbon coupling reactions.

As used herein, the term "palladium scavengers" refers to palladium compounds that are capable of serquestering organic functionalities from a solution in order to ease the purification process upon completion of a synthesis.

As used herein, the term "residual palladium" refers to palladium that is present in a sample, i.e., moiety, solution, etc.

As used herein, the terms "charcoal particle" and "polymer-bound charcoal particle" refer to a residue of graphitic carbon of small sizes (tens or hundreds of microns) that are conjugated to a polymer.

As used herein, the term "thiol moiety" refers to an organosulfur compound in which a thio group —SH is attached to a carbon atom of an aliphatic or aromatic moiety.

As used herein, the term "polymer-bound thiol moiety" refers to a thiol moiety that is conjugated to a polymer.

As used herein, the term "amine moiety" refers to an organonitrogen compound in which a nitrogen-containing group is attached to a carbon atom of an aliphatic or aromatic moiety.

As used herein, the term "polymer-bound amine moiety" refers to an amine moiety that is conjugated to a polymer.

As used herein, the term "Pd(dtbpf)Cl$_2$" refers to [1,1'-Bis(di-tert-butylphosphino) ferrocene]dichloropalladium.

As used herein, the term "PdCl$_2$P(Ph$_3$)$_2$" refers to bis(triphenylphosphine)palladium chloride.

As used herein, the terms "Pd(dppf)Cl$_2$" and "Pd(dippf)Cl$_2$" refer to [1,1'-Bis(diphenylphosphino)ferrocene]dichloropalladium.

As used herein, the term "Pd$_2$(dba)$_3$" refers to tris(dibenzylideneacetone)dipalladium.

As used herein, the term "Boc" refers to tert-Butoxycarbonyl. The term "Boc$_2$O" refers to di-tert-butyl dicarbonate.

As used herein, the term "Cbz" refers to cabroxybenzyl. The term "CbzCl" refers to benzyl chloroformate, i.e., the benzyl ester of chloroformic acid.

Pharmaceutical Compositions

The compounds described herein can be used for the preparation of pharmaceutical compositions for the treatment of diseases, including cancer. The provided compositions are, inter alia, suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject.

Compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient.

Pharmaceutical compositions provided by the present disclosure include compositions wherein the active ingredient (e.g. compositions described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, the compounds and antibodies described herein will contain an amount of active ingredient effective to achieve the desired result, e.g., modulating the activity of a target molecule, and/or reducing, eliminating, or slowing the progression of disease symptoms. Determination of a therapeutically effective amount of a compound of the disclosure is well within the capabilities of those skilled in the art, especially in light of the detailed disclosure herein.

Provided compositions can include a single agent or more than one agent. The compositions for administration will commonly include an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods and compounds of the disclosure. Adjustment and manipulation of established dosages (e.g., frequency and duration) are well within the ability of those skilled in the art.

For any composition described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure should be sufficient to affect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred "Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

In an aspect, there is provided a precipitate of formula (I):

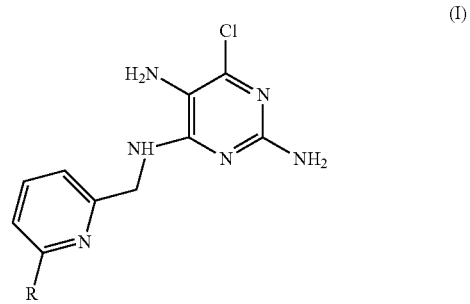

(I)

or a tautomer, stereoisomer, or pharmaceutically acceptable salt thereof, wherein:

R is —(CR$^a$R$^b$)—O—R$^2$;

R$^a$ is H or alkyl;

R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocylic ring comprising a ring member selected from O, N(R$^3$) and S;

R$^2$ is H, alkyl, cycloalkyl or heterocycloalkyl, wherein the alkyl or cycloalkyl may optionally be substituted with halo, alkoxy or heterocycloalkyl;

R$^3$ is H or alkyl;

wherein, heteroaryl is a 5 or 6 membered aromatic ring, comprising one or two ring members selected from N, N(R$^4$), S and O;

alkyl (or the alkyl group of the alkoxy group) is a linear or branched saturated hydrocarbon containing up to 10 carbon atoms;

alkoxy is a linear or branched saturated hydrocarbon containing up to 10 carbon atoms attached to the remainder of the molecule through an oxygen linker;

heterocycloalkyl is a C-linked or N-linked 3 to 10 membered non-aromatic, monocyclic ring, wherein said heterocycloalkyl ring comprises 1, 2 or 3 ring members independently selected from N, N(R$^4$), S(O)$_q$ and O;

R$^4$ is H or alkyl; and q is 0, 1 or 2.

In embodiments, the precipitate of formula (I) has the following structure:

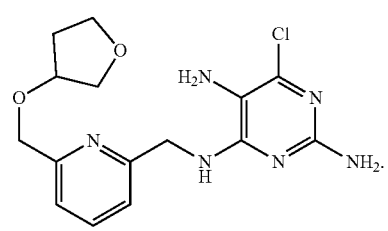 [SMILES: Nc1nc(Cl)c(N)c(NCc2cccc(COC3CCOC3)n2)n1]

In embodiments, the precipitate of formula (I) has the following structure:

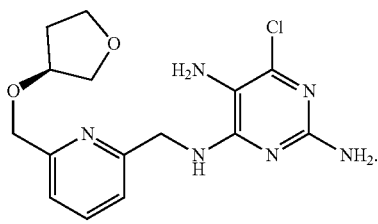 [SMILES: Nc1nc(Cl)c(N)c(NCc2cccc(CO[C@H]3CCOC3)n2)n1]

In another aspect, there is provided a precipitate of formula (II):

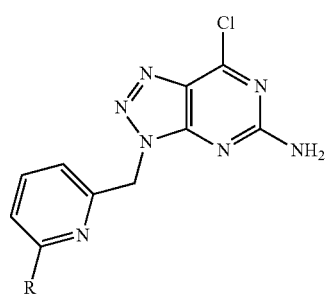

or a tautomer, stereoisomer, or pharmaceutically acceptable salt thereof, wherein:

R is —(CR$^a$R$^b$)—O—R$^2$;

R$^a$ is H or alkyl;

R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocylic ring comprising a ring member selected from O, N(R$^3$) and S;

R$^2$ is H, alkyl, cycloalkyl or heterocycloalkyl, wherein said alkyl or cycloalkyl may optionally be substituted with halo, alkoxy or heterocycloalkyl;

R$^3$ is H or alkyl;

wherein, heteroaryl is a 5 or 6 membered aromatic ring, comprising one or two ring members selected from N, N(R$^4$), S and O;

alkyl (or the alkyl group of the alkoxy group) is a linear or branched saturated hydrocarbon containing up to 10 carbon atoms;

alkoxy is a linear or branched saturated hydrocarbon containing up to 10 carbon atoms attached to the remainder of the molecule through an oxygen linker;

heterocycloalkyl is a C-linked or N-linked 3 to 10 membered non-aromatic, monocyclic ring, wherein said heterocycloalkyl ring comprises 1, 2 or 3 ring members independently selected from N, N(R$^4$), S(O)$_q$ and O;

R$^4$ is H or alkyl; and q is 0, 1 or 2.

In embodiments, the precipitate of formula (II) has the following structure:

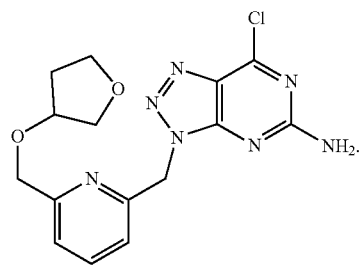 [SMILES: Nc1nc(Cl)c2nnn(Cc3cccc(COC4CCOC4)n3)c2n1]

In embodiments, the precipitate of formula (II) has the following structure:

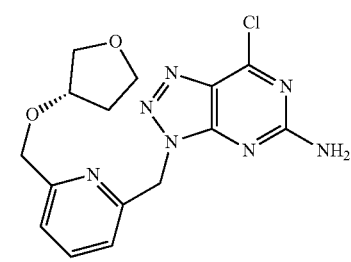 [SMILES: Nc1nc(Cl)c2nnn(Cc3cccc(CO[C@H]4CCOC4)n3)c2n1]

In embodiments, R$^a$ and R$^b$ are independently H and R$^2$ is tetrahydrofuranyl.

In embodiments, R$^a$ and R$^b$ are independently H.

In embodiments, R is

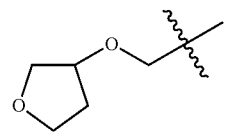

In embodiments, R is

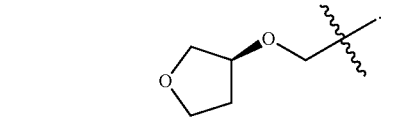

In embodiments, the precipitate is a salt.

In embodiments, the precipitate is a hydrochloric acid salt, a di-hydrochloride acid salt, a hydrobromide salt, dihydromide salt, an alkylsulfonate salt, an acetate salt or a formate salt.

In embodiments, the precipitate is a hydrochloric acid salt or a di-hydrochloride acid salt.

In embodiments, the precipitate is a free base.

In embodiments, the precipitate is crystalline.

In embodiments, the precipitate is of the formula (I):

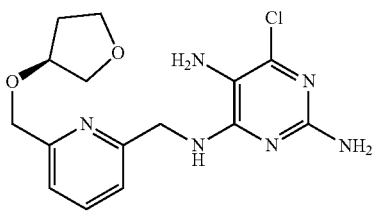 [SMILES: Nc1nc(Cl)c(N)c(NCc2cccc(CO[C@H]3CCOC3)n2)n1]

In embodiments, the precipitate is of the formula (II):

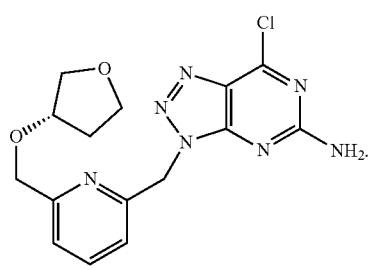

In another aspect, there is provided a method of isolating a precipitate of formula (I):

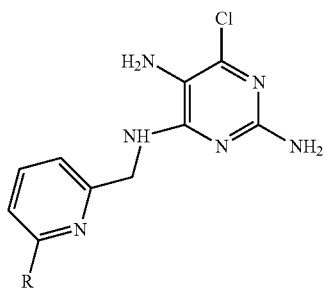
(I)

comprising the steps of:
(a) reacting a compound of the formula:

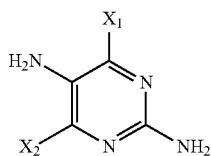

with a compound of the formula:

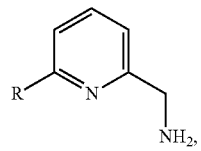

in the presence of a base;
wherein,
$X_1$ and $X_2$ are independently halo, and
wherein R is —$(CR^aR^b)$—O—$R^2$;
$R^a$ is H or alkyl;
$R^b$ is H or alkyl; or $R^a$ and $R^b$ together with the atom to which they are attached form a 3 to 8 membered saturated or partially saturated hydrocarbon ring or form a 4 to 8 membered saturated or partially saturated heterocylic ring comprising a ring member selected from O, $N(R^3)$ and S;
$R^2$ is H, alkyl, cycloalkyl or heterocycloalkyl, wherein said alkyl or cycloalkyl may optionally be substituted with halo, alkoxy or heterocycloalkyl;
$R^3$ is H or alkyl;
wherein, heteroaryl is a 5 or 6 membered aromatic ring, comprising one or two ring members selected from N, $N(R^4)$, S and O;
alkyl (or the alkyl group of the alkoxy group) is a linear or branched saturated hydrocarbon containing up to 10 carbon atoms;
alkoxy is a linear or branched saturated hydrocarbon containing up to 10 carbon atoms attached to the remainder of the molecule through an oxygen linker;
heterocycloalkyl is a C-linked or N-linked 3 to 10 membered non-aromatic, monocyclic ring, wherein said heterocycloalkyl ring comprises 1, 2 or 3 ring members independently selected from N, $N(R^4)$, $S(O)_q$ and O;
$R^4$ is H or alkyl; and
q is 0, 1 or 2; and
(b) isolating the precipitate of formula (I).
In embodiments, the precipitate of formula (I) is:

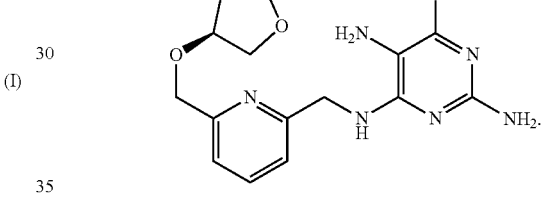

In embodiments, $X_1$ and $X_2$ are chloro, fluoro or bromo, iodo or alkylsulfonate.
In embodiments, $X_1$ and $X_2$ are chloro.
In embodiments, the base is N-methylmorpholine or triethanolamine.
In embodiments, the precipitate is crystalline.
In embodiments, the precipitate of formula (I) is isolated as a salt.
In embodiments, the salt is a hydrochloric acid salt, a di-hydrochloride acid salt, a hydrobromide salt, an alkylsulfonate salt, an acetate salt or a formate salt.
In embodiments, the salt is a hydrochloric acid salt, a di-hydrochloride acid salt, a hydrobromide salt, an alkylsulfonate salt, an acetate salt or a formate salt.
In embodiments, the precipitate of formula (I) is isolated as a hydrochloric acid salt or a dihydrochloride salt.
In embodiments, the precipitate of formula (I) is isolated as a free base.
In embodiments, the precipitate of formula (I) is isolated by re-crystallization from a polar solvent.
In embodiments, the polar solvent is a polar protic solvent or a polar aprotic solvent.
In embodiments, the polar solvent is a polar protic solvent.
In embodiments, the polar protic solvent is an alcohol.
In embodiments, the alcohol is 2-proponol, ethanol or methanol.
In embodiments, the precipitate of formula (I) is isolated by re-crystallization from methyl alcohol, trimethylsilyl chloride, hydrochloric acid, hydrogen chloride, or dimethylformamide.

In embodiments, the precipitate of formula (I) is isolated by re-crystallization from hydrogen choride in an alcohol solvent or a non-alcoholic solvent.

In embodiments, the precipitate of formula (I) is isolated by re-crystallization from hydrochloric acid.

In another aspect, the method comprises the step of forming a compound of formula (II):

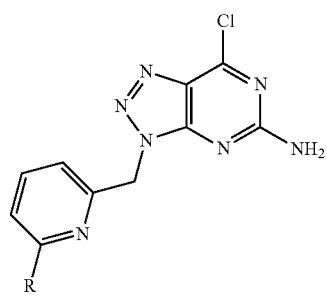

wherein R is as defined above, by:
(a) reacting the precipitate of formula (I) with a nitrite; and
(b) isolating the compound of formula (II).

In embodiments, the precipitate of formula (II) is

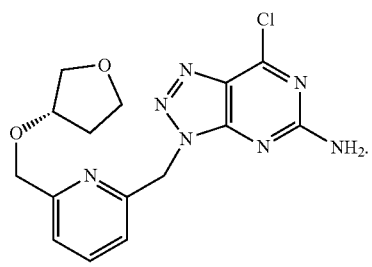

In embodiments, $R^a$ and $R^b$ are independently H.
In embodiments, $R^a$ and $R^b$ are independently H and $R^2$ is tetrahydrofuranyl.
In embodiments, R is

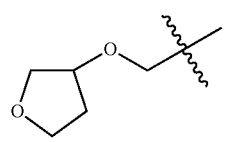 [SMILES: *COC1CCOC1]

In embodiments, R is

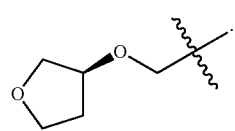

In embodiments, the nitrite is isoamyl nitrite or sodium nitrite.

In embodiments, the precipitate of formula (I) is reacted with a nitrite at a pH of about 1.0 to about 7.0.

In embodiments, the precipitate of formula (I) is reacted with a nitrite at a pH of about 1.0 to about 3.0.

In embodiments, the compound of formula (II) is isolated as a salt.

In embodiments, the compound of formula (II) is a hydrochloric acid salt, a di-hydrochloride acid salt, a hydrobromide salt, a di-hydrobromide salt, an alkylsulfonate salt, an acetate salt or a formate salt.

In embodiments, the compound of formula (II) is isolated as a hydrochloric acid salt.

In embodiments, the compound of formula (II) is isolated as a free base.

In embodiments, the step of isolating the compound of formula (II) is in the presence of a base.

In embodiments, the base is a carbonate or a hydroxide.

In embodiments, the base is a carbonate.

In embodiments, the carbonate is sodium carbonate, sodium bicarbonate, potassium carbonate or potassium bicarbonate.

In embodiments, the base is a hydroxide.

In embodiments, the base is sodium hydroxide or potassium hydroxide.

In embodiments, the compound is isolated as a precipitate.

In embodiments, the compound is crystalline.

In embodiments, the precipitate of formula (I) is of the formula:

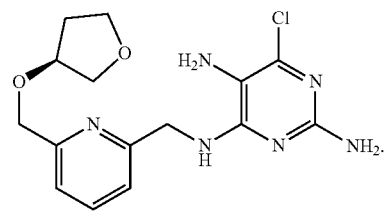 [SMILES: Nc1nc(Cl)c(N)c(NCc2cccc(CO[C@H]3CCOC3)n2)n1]

In embodiments, the compound of formula II is of the formula:

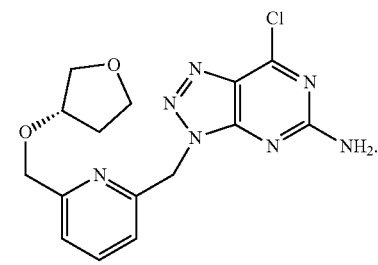 [SMILES: Nc1nc(Cl)c2nnn(Cc3cccc(CO[C@H]4CCOC4)n3)c2n1]

In another aspect, the method comprises the step of forming a compound of formula (III):

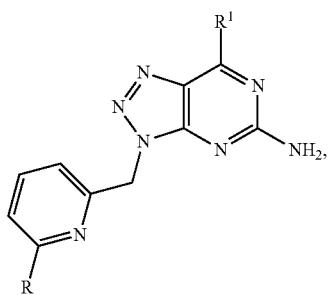

(III)

by:
(a) reacting a compound of formula (II) with a compound of the formula R$^1$—Y in the presence of a palladium catalyst and a base, wherein Y is a leaving group,
wherein, R is —(CR$^a$R$^b$)—O—R$^2$;
R$^a$ is H or alkyl;
R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocylic ring comprising a ring member selected from O, N(R$^3$) and S;
R$^1$ is phenyl or heteroaryl, wherein said phenyl or said heteroaryl group may be optionally substituted with alkyl, alkoxy, halo or —CN;
R$^2$ is H, alkyl, cycloalkyl or heterocycloalkyl, wherein said alkyl or cycloalkyl may optionally be substituted with halo, alkoxy or heterocycloalkyl;
R$^3$ is H or alkyl;
wherein, heteroaryl is a 5 or 6 membered aromatic ring, comprising one or two ring members selected from N, N(R$^4$), S and O;
alkyl (or the alkyl group of the alkoxy group) is a linear or branched saturated hydrocarbon containing up to 10 carbon atoms;
alkoxy is a linear or branched saturated hydrocarbon containing up to 10 carbon atoms attached to the remainder of the molecule through an oxygen linker;
heterocycloalkyl is a C-linked or N-linked 3 to 10 membered non-aromatic, monocyclic ring, wherein said heterocycloalkyl ring comprises 1, 2 or 3 ring members independently selected from N, N(R$^4$), S(O)$_q$ and O;
R$^4$ is H or alkyl; and
q is 0, 1 or 2; and
(b) isolating the compound of formula (III)

It is to be understood that, when performing step (a) for forming the compound of formula (III), various methods known in the art may be followed such as, for example, Suzuki reactions, Grignard reactions and Kumada reactions.

In embodiments, Y is an organometallic leaving group.

In embodiments, the organometallic leaving group is a boronate ester moiety or a boronic acid moiety.

In embodiments, the organometallic leaving group is a boronate ester moiety.

In embodiments, the compound of formula (III) is isolated by re-crystallization from an alcohol solvent, tetrahydrofuran, and water.

In embodiments, the compound of formula (III) is isolated by re-crystallization from an alcohol solvent, 2-methyltetrahydrofuran, and water.

In embodiments, the alcohol solvent is isopropanol.

In embodiments, the base is an inorganic base.

In embodiments, the inorganic base is potassium carbonate, potassium bicarbonate, sodium carbonate, sodium bicarbonate, cesium carbonate, sodium hydroxide, sodium ethoxide or sodium methoxide.

In embodiments, the palladium catalyst is a palladium complex.

In embodiments, the palladium catalyst is Pd(dtbpf)Cl$_2$, PdCl$_2$P(Ph$_3$)$_2$, PdP(Ph$_2$)$_4$, Pd(dppf)Cl$_2$, Pd(dippf)Cl$_2$ or Pd$_2$(dba)$_3$.

In embodiments, the boronate ester moiety is pinacolborane, boronic acid, 2-(5-methylfuran-2-yl) catecholborane, 2-(5-methylfuran-2-yl)-1,3,2-dioxaborinane, diisopropyl (5-methylfuran-2-yl)boronate, (1s,5s)-9-(5-methylfuran-2-yl)-9-borabicyclo[3.3.1]nonane or (5-methylfuran-2-yl)boronic acid.

In embodiments, the boronate ester moiety has the formula:

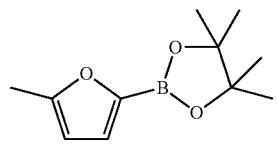

In embodiments, the compound of formula (III) is isolated as a precipitate.

In embodiments, the compound of formula (III) is crystalline.

In embodiments, the compound of formula (III) is of the formula:

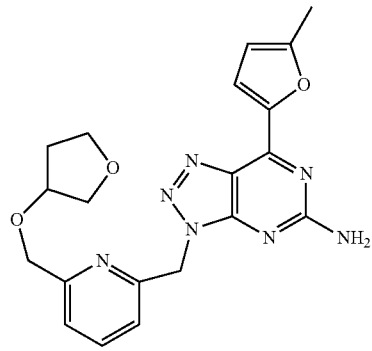 [SMILES: Cc1ccc(-c2nc(N)nc3c2nnn3Cc2cccc(COC3CCOC3)n2)o1]

In embodiments, the compound of formula (III) is of the formula:

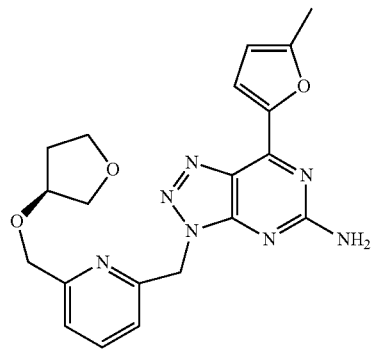 [SMILES: Cc1ccc(-c2nc(N)nc3c2nnn3Cc2cccc(CO[C@H]3CCOC3)n2)o1]

In embodiments, the method further comprises the step of contacting the palladium catalyst with a palladium scavenger.

In embodiments, the palladium scavenger is a charcoal particle, a polymer-bound charcoal particle, a thiol moiety, a polymer-bound thiol moiety, an amine moiety, or a polymer-bound amine moiety. It is to be understood that, for example, a polymer-bound thiol or a polymer-bound charcoal particle can include silica gel based and organic polymer (such as polyethylene ether).

In embodiments, the charcoal particle is less than about 200μ, or less than about 150μ, or less than about 100μ, or less than about 75μ, or less than about 50μ, or less than about 25μ.

In embodiments, the length of the longest dimension of the charcoal particle is less than about 200μ, or less than about 150μ, or less than about 100μ, or less than about 75μ, or less than about 50μ, or less than about 25.

In embodiments, the average length of the longest dimension of the charcoal particle is less than about 200μ, or less than about 150μ, or less than about 100μ, or less than about 75, or less than about 50μ, or less than about 25μ.

In embodiments, the thiol moiety is cysteine.

In embodiments, the polymer-bound thiol moiety is polymer-bound cysteine.

In embodiments, the palladium scavenger is contained in a preformed device. Various commercially available charcoal particles and devices can be used to remove residual palladium. For example, Darco KB-G activated charcoal (available from Sigma Aldrich, St. Louis, Mo., USA) and 3M Biocap filter cartridge containing charcoal particles (available from 3M, Minneapolis, Minn., USA). Polymer bound thiol (SiST) can also be used to remove residual palladium, such as a heterogeneous mixture of SiST or as a flow through using a filter cartridge.

In embodiments, the step of contacting the palladium catalyst with a palladium scavenger results in a reaction mixture comprising the compound of formula (III) having less than about 500 ppm residual palladium, or less than about 400 ppm residual palladium, or less than about 300 ppm residual palladium, or less than about 200 ppm residual palladium, or less than about 100 ppm residual palladium, or less than about 90 ppm residual palladium, or less than about 80 ppm residual palladium, or less than about 70 ppm residual palladium, or less than about 60 ppm residual palladium, or less than about 50 ppm residual palladium, or less than about 40 ppm residual palladium, or less than about 30 ppm residual palladium, or less than about 20 ppm residual palladium, or less than about 10 ppm residual palladium, or less than about 5 ppm residual palladium, or less than about 4 ppm residual palladium, or less than about 3 ppm residual palladium, or less than about 2 ppm residual palladium, or less than about 1 ppm residual palladium.

It is to be understood that the step of contacting the palladium catalyst with a palladium scavenger can be repeated one or more times. Additionally, when repeating the step of contacting the palladium catalyst with a palladium scavenger, the same or different palladium scavengers described herein may be utilized individually or sequentially in any order. For example, the reaction mixture may be first contacted with a charcoal particle, followed by one or more of a polymer-bound charcoal particle and/or a thiol moiety and/or a polymer-bound thiol moiety and/or an amine moiety and/or a polymer-bound amine moiety, in any order, and/or contained in a preformed device such as a cartridge.

In another aspect, there is provided a precipitate of formula (IV):

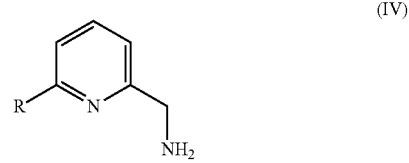

(IV)

or a hydrate, tautomer, stereoisomer, or pharmaceutically acceptable salt thereof, wherein:

R is —(CR$^a$R$^b$)—O—R$^2$;

R$^a$ is H or alkyl;

R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocylic ring comprising a ring member selected from O, N(R$^3$) and S;

R$^2$ is H, alkyl, cycloalkyl or heterocycloalkyl, wherein the alkyl or cycloalkyl may optionally be substituted with halo, alkoxy or heterocycloalkyl;

R$^3$ is H or alkyl;

wherein: heteroaryl is a 5 or 6 membered aromatic ring, comprising one or two ring members selected from N, N(R$^4$), S and O;

alkyl (or the alkyl group of the alkoxy group) is a linear or branched saturated hydrocarbon containing up to 10 carbon atoms;

heterocycloalkyl is a C-linked or N-linked 3 to 10 membered non-aromatic, monocyclic ring, wherein said heterocycloalkyl ring comprises 1, 2 or 3 ring members independently selected from N, N(R$^4$), S(O)$_q$ and O; and R$^4$ is H or alkyl.

In embodiments, R$^a$ and R$^b$ are independently H and R$^2$ is tetrahydrofuranyl.

In embodiments, R$^a$ and R$^b$ are independently H.

In embodiments, R is

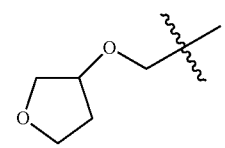 [SMILES: *COC1CCOC1]

In embodiments, R is

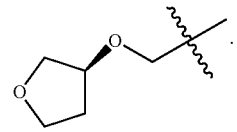

In embodiments, the precipitate is a free base.

In embodiments, the precipitate is crystalline.

In embodiments, the precipitate is of the formula:

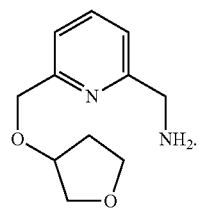 [SMILES: NCc1cccc(COC2CCOC2)n1]

In embodiments, the precipitate is of the formula

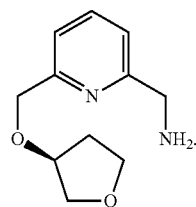 [SMILES: NCc1cccc(CO[C@H]2CCOC2)n1]

In another aspect, provided is a compound of formula (V):

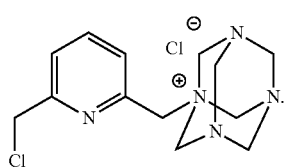 (V)

In embodiments, the compound of formula (V) is crystalline.

In embodiments, the compound of formula (V) is isolated as a free base.

In embodiments, the compound of formula (V) is isolated by filtration.

In another aspect, provided is a method of forming a compound of formula (V):

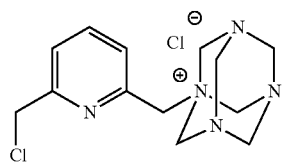 [SMILES: ClCc1cccc(C[N+]23CN4CN(CN(C4)C2)C3)n1 ; [Cl-]]

comprising the step of reacting the compound of formula:

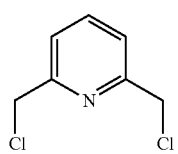

with hexamethylenetetraamine (HMTA) of formula:

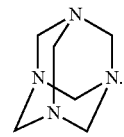

In another aspect, provided is a method of forming the compound of formula:

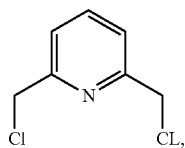

comprising the step of reacting the compound of formula

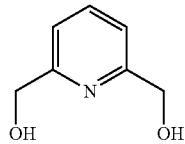

with a chlorinating agent in the presence of organic solvent.

In embodiments, the chlorinating agent is thionyl chloride.

In embodiments, the organic solvent is dichloromethane.

In another aspect, provided is a method of forming the compound of formula:

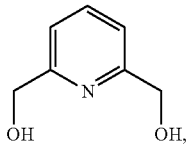

comprising:
(a) a step of reacting the compound of formula

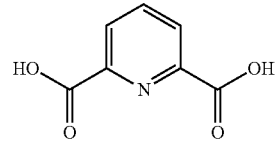 [SMILES: O=C(O)c1cccc(C(=O)O)n1]

with inorganic acid in the presence of alcohol to achieve the compound of formula

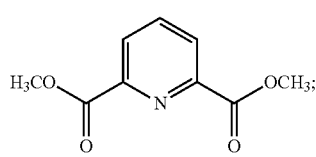

and
(b) a step of reacting the compound of formula

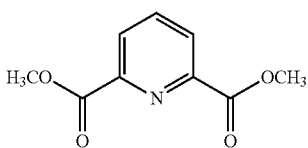 [SMILES: COC(=O)c1cccc(C(=O)OC)n1]

with a reducing agent in the presence of alcohol and a catalyst.

In embodiments, the inorganic acid is sulfuric acid.

In embodiments, the reducing agent is sodium borohydride.

In embodiments, the alcohol is isopropanol, ethanol or methanol. In embodiments, the alcohol is ethanol.

In embodiments, the catalyst is lithium aluminium hydride.

In another aspect, provided is a method of forming the compound of formula:

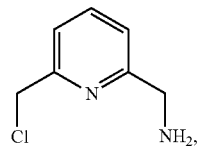

comprising the step of reacting the compound of formula (V):

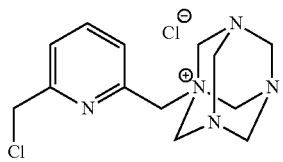 [SMILES: ClCc1cccc(C[N+]23CN4CN(CN(C4)C2)C3)n1 ; [Cl-]]

with alcohol in the presence of inorganic acid.

In embodiments, the inorganic acid is hydrochloric acid.

In embodiments, the alcohol is isopropanol, ethanol or methanol. In embodiments, the alcohol is ethanol.

In another aspect, provided is a method of forming the compound of formula:

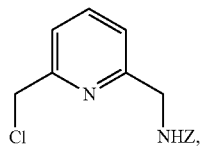

wherein Z is butyloxycarbonyl (Boc) or cabroxybenzyl (Cbz);
comprising the step of reacting the compound of formula

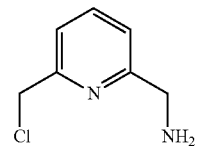

with Boc$_2$O or CbzCl in the presence of organic solvent.

In embodiments, the organic solvent is dichloromethane.

In another aspect, provided is a method of forming the compound of formula:

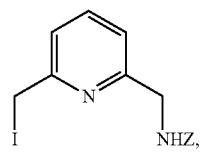

wherein Z is Boc or Cbz;
comprising the step of reacting the compound of formula

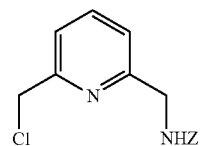

with an ionic compound in the presence of organic solvent.

In embodiment, the ionic compound is sodium iodide

In embodiments, the organic solvent is tetrahydrofuran.

In another aspect, provided is a method of forming the compound of formula:

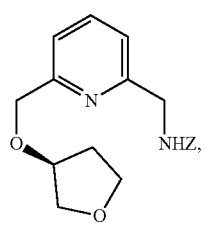

wherein Z is Boc or Cbz;
comprising the step of reacting the compound of formula

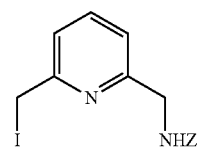

with the compound of formula

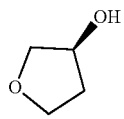

in the presence of organic solvent and catalyst.

In embodiments, the organic solvent is tetrahydrofuran or toluene.

In embodiments, the catalyst is potassium t-butoxide.

In another aspect, provided is a method of forming the compound of formula:

comprising the step of reacting the compound of formula

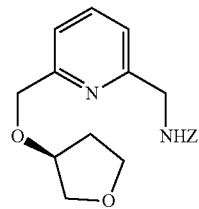

with an organic acid in the presence of organic solvent.

In embodiments, the organic acid is methanesulfonic acid.
In embodiments, the organic solvent is dichloromethane.
In another aspect, provided is a compound of formula (VI):

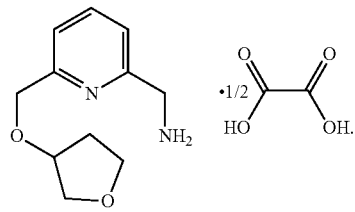 [SMILES: NCc1cccc(COC2CCOC2)n1 ; O=C(O)C(=O)O]

In embodiments, the compound of formula (VI) is of the structure:

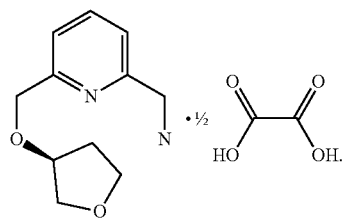 [SMILES: NCc1cccc(CO[C@H]2CCOC2)n1 ; O=C(O)C(=O)O]

In another aspect, provided is a method of forming the compound of formula (VI):

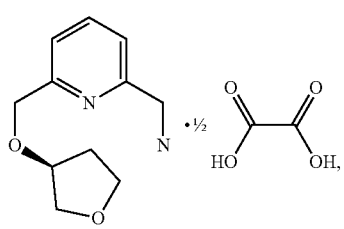

comprising the step of reacting the compound of formula

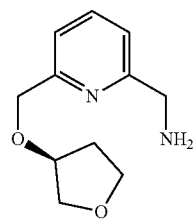 [SMILES: NCc1cccc(CO[C@H]2CCOC2)n1]

with an organic acid in the presence of organic solvent.

In embodiments, the compound of formula (VI) is crystalline.

In embodiments, the compound of formula (VI) is isolated by filtration with the organic solvent.

In embodiments, the organic solvent is alcohol.

In embodiments, the alcohol is isopropanol, ethanol or methanol. In embodiments, the alcohol is isopropanol.

In embodiments, the organic acid is oxalic acid.

In another aspect, provided is a compound of formula (VII):

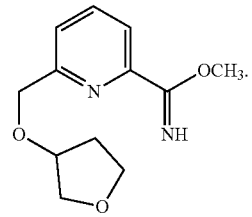 [SMILES: COC(=N)c1cccc(COC2CCOC2)n1]

In embodiments, the compound of formula (VII) is of the structure:

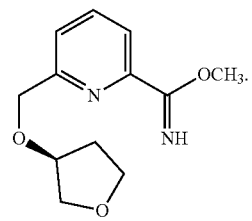 [SMILES: COC(=N)c1cccc(CO[C@H]2CCOC2)n1]

In another aspect, provided is a method of forming the compound of formula (VII):

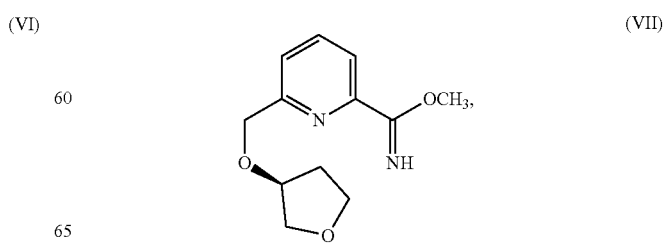

comprising the step of reacting the compound of formula

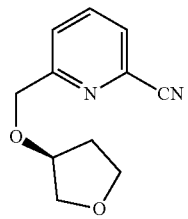 [SMILES: N#Cc1cccc(CO[C@H]2CCOC2)n1]

with a basic reagent.

In embodiments, the basic reagent is sodium methoxide.

In another aspect, provided is a method of forming the compound of formula:

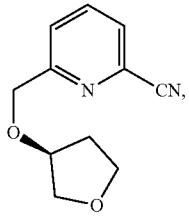 [SMILES: N#Cc1cccc(CO[C@H]2CCOC2)n1]

comprising the step of reacting the compound of formula

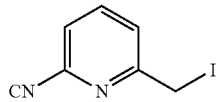

with the compound of formula

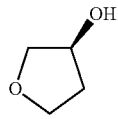

in the presence of a base.

In another aspect, provided is a method of forming the compound of formula:

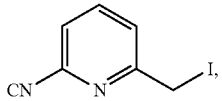

comprising the step of reacting the compound of formula

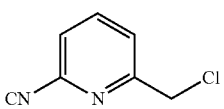

with an ionic compound in the presence of organic solvent.

In embodiment, the ionic compound is sodium iodide

In embodiments, the organic solvent is tetrahydrofuran.

In another aspect, provided is a method of forming the compound of formula:

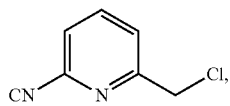

comprising the step of reacting the compound of formula

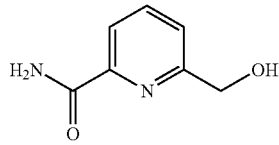 [SMILES: NC(=O)c1cccc(CO)n1]

in the presence of catalyst.

In embodiments, the catalyst is phosphoryl chloride.

In another aspect, provided is a method of forming the compound of formula:

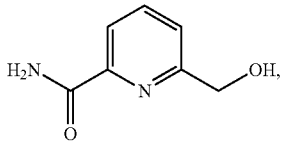

comprising the step of reacting the compound of formula

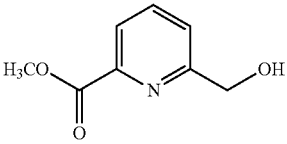 [SMILES: COC(=O)c1cccc(CO)n1]

with a base.

In embodiments, the base is ammonium hydroxide.

In another aspect, provided is a method of forming the compound of formula:

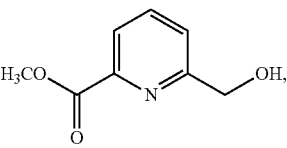 [SMILES: COC(=O)c1cccc(CO)n1]

comprising the step of reacting the compound of formula

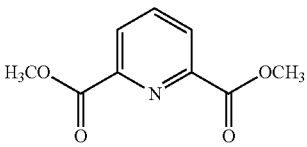 [SMILES: COC(=O)c1cccc(C(=O)OC)n1]

with a reducing agent.

In embodiments, the reducing agent is sodium borohydride.

In another aspect, provided is a method of forming the compound of formula:

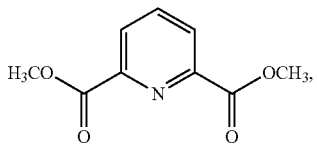 [SMILES: COC(=O)c1cccc(C(=O)OC)n1]

comprising the step of reacting the compound of formula

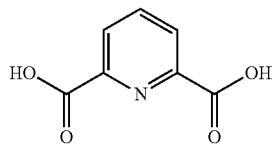

with a proton donating compound in the presence of organic solvent.

In embodiments, the organic solvent is alcohol.
In embodiments, the alcohol is isopropanol, ethanol or methanol. In embodiments, the alcohol is methanol.
In embodiments, the proton donating compound is diacid.
In another aspect, provided is a method of forming the compound of formula:

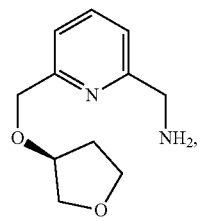 [SMILES: NCc1cccc(CO[C@H]2CCOC2)n1]

comprising the step of reacting the compound of formula (VII):

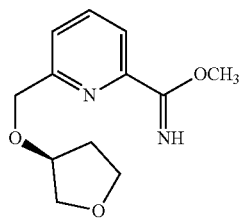 [SMILES: COC(=N)c1cccc(CO[C@H]2CCOC2)n1]

with a transition metal.
In embodiments, the compound of formula

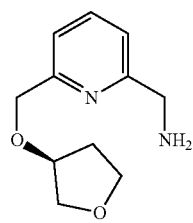 [SMILES: NCc1cccc(CO[C@H]2CCOC2)n1]

is a free base.

In embodiments, the transition metal is iron, cobalt, copper, zinc, or nickel. In embodiments, the transition metal is nickel.

In another aspect, provided is a method of forming the compound of formula (VI):

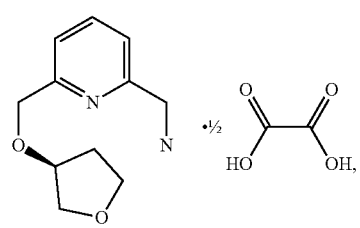

(VI)

comprising the step of reacting the compound of formula

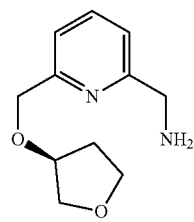 [SMILES: NCc1cccc(CO[C@H]2CCOC2)n1]

with an organic acid in the presence of organic solvent.

In embodiments, the compound of formula (VI) is crystalline.
In embodiments, the compound formula (VI) is isolated by filtration from the organic solvent.
In embodiments, the organic solvent is alcohol.
In embodiments, the alcohol is isopropanol, ethanol or methanol. In embodiments, the alcohol is isopropanol.
In embodiments, the organic acid is oxalic acid.

P EMBODIMENTS

Embodiment P1

A precipitate of the formula (I):

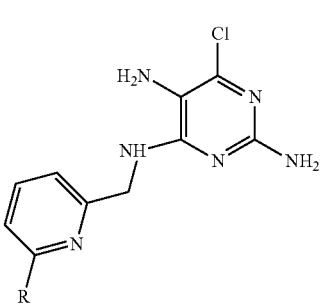

(I)

or a tautomer, stereoisomer or pharmaceutically acceptable salt thereof, wherein:
R is —(CR$^a$R$^b$)—O—R$^2$;
R$^a$ is H or alkyl;
R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocylic ring comprising a ring member selected from O, N(R$^3$) and S;

R$^2$ is H, alkyl, cycloalkyl or heterocycloalkyl, wherein the alkyl or cycloalkyl may optionally be substituted with halo, alkoxy or heterocycloalkyl;

R$^3$ is H or alkyl;

wherein, heteroaryl is a 5 or 6 membered aromatic ring, comprising one or two ring members selected from N, N(R$^4$), S and O;

alkyl (or the alkyl group of the alkoxy group) is a linear or branched saturated hydrocarbon containing up to 10 carbon atoms;

alkoxy is a linear or branched saturated hydrocarbon containing up to 10 carbon atoms attached to the remainder of the molecule through an oxygen linker;

heterocycloalkyl is a C-linked or N-linked 3 to 10 membered non-aromatic, monocyclic ring, wherein said heterocycloalkyl ring comprises 1, 2 or 3 ring members independently selected from N, N(R$^4$), S(O)$_q$ and O;

R$^4$ is H or alkyl; and q is 0, 1 or 2.

Embodiment P2

A precipitate of the formula (II):

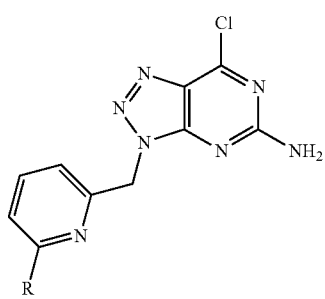

(II)

or a tautomer, stereoisomer, or pharmaceutically acceptable salt thereof, wherein:

R is —(CR$^a$R$^b$)—O—R$^2$;

R$^a$ is H or alkyl;

R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocyclic ring comprising a ring member selected from O, N(R$^3$) and S;

R$^2$ is H, alkyl, cycloalkyl or heterocycloalkyl, wherein said alkyl or cycloalkyl may optionally be substituted with halo, alkoxy or heterocycloalkyl;

R$^3$ is H or alkyl;

wherein, heteroaryl is a 5 or 6 membered aromatic ring, comprising one or two ring members selected from N, N(R$^4$), S and O;

alkyl (or the alkyl group of the alkoxy group) is a linear or branched saturated hydrocarbon containing up to 10 carbon atoms;

alkoxy is a linear or branched saturated hydrocarbon containing up to 10 carbon atoms attached to the remainder of the molecule through an oxygen linker;

heterocycloalkyl is a C-linked or N-linked 3 to 10 membered non-aromatic, monocyclic ring, wherein said heterocycloalkyl ring comprises 1, 2 or 3 ring members independently selected from N, N(R$^4$), S(O)$_q$ and O;

R$^4$ is H or alkyl; and q is 0, 1 or 2.

Embodiment P3

The precipitate of embodiment P1 or P2, wherein R$^a$ and R$^b$ are independently H; and R$^2$ is tetrahydrofuranyl.

Embodiment P4

The precipitate of embodiment P1 or P2, wherein R$^a$ and R$^b$ are independently H.

Embodiment P5

The precipitate of embodiment P1 or P2, wherein R is

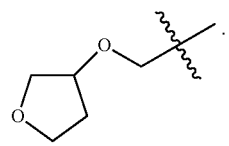 [SMILES: *COC1CCOC1]

Embodiment P6

The precipitate of embodiment P1 or P2, which is a salt.

Embodiment P7

The precipitate of embodiment P6, wherein said precipitate is a hydrochloric acid salt, a di-hydrochloride acid salt, a hydrobromide salt, dihydromide salt, an alkylsulfonate salt, an acetate salt or a formate salt.

Embodiment P8

The precipitate of embodiment P7 wherein said precipitate is a hydrochloric acid salt or a dihydrochloride salt.

Embodiment P9

The precipitate of embodiment P1 or P2, wherein said precipitate is a free base.

Embodiment P10

The precipitate of embodiment P1 or P2, which is crystalline.

Embodiment P11

The precipitate of embodiment P1 of the formula:

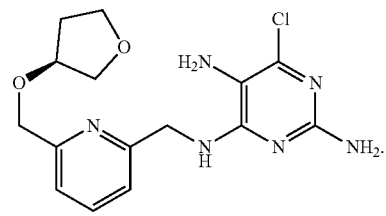 [SMILES: Nc1nc(Cl)c(N)c(NCc2cccc(CO[C@H]3CCOC3)n2)n1]

Embodiment P12

The precipitate of embodiment P1 of the formula:

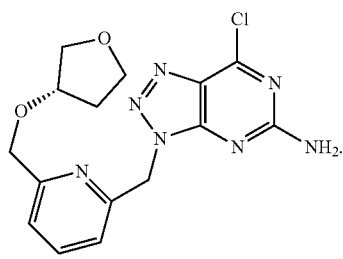 [SMILES: Nc1nc(Cl)c2nnn(Cc3cccc(CO[C@H]4CCOC4)n3)c2n1]

Embodiment P13

A method of isolating a precipitate of the formula (I):
comprising the steps of:

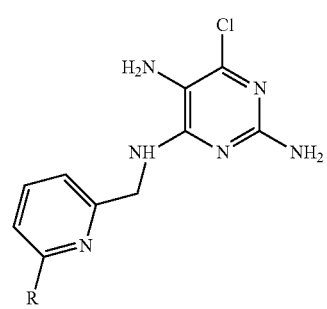

(a) reacting a compound of the formula:

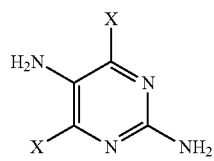

with a compound of the formula:

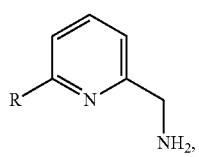

in the presence of a base;
wherein,
X is halo, and
wherein R is —$(CR^aR^b)$—O—$R^2$;
$R^a$ is H or alkyl;
$R^b$ is H or alkyl; or $R^a$ and $R^b$ together with the atom to which they are attached form a 3 to 8 membered saturated or partially saturated hydrocarbon ring or form a 4 to 8 membered saturated or partially saturated heterocylic ring comprising a ring member selected from O, $N(R^3)$ and S;

$R^2$ is H, alkyl, cycloalkyl or heterocycloalkyl, wherein said alkyl or cycloalkyl may optionally be substituted with halo, alkoxy or heterocycloalkyl;
$R^3$ is H or alkyl;
wherein, heteroaryl is a 5 or 6 membered aromatic ring, comprising one or two ring members selected from N, $N(R^4)$, S and O;
alkyl (or the alkyl group of the alkoxy group) is a linear or branched saturated hydrocarbon containing up to 10 carbon atoms;
alkoxy is a linear or branched saturated hydrocarbon containing up to 10 carbon atoms attached to the remainder of the molecule through an oxygen linker;
heterocycloalkyl is a C-linked or N-linked 3 to 10 membered non-aromatic, monocyclic ring, wherein said heterocycloalkyl ring comprises 1, 2 or 3 ring members independently selected from N, $N(R^4)$, $S(O)_q$ and O;
$R^4$ is H or alkyl; and
q is 0, 1 or 2; and
(b) isolating the precipitate of formula (I).

Embodiment P14

The method of embodiment P13, wherein X is chloro, fluoro or bromo, iodo or alkylsulfonate.

Embodiment P15

The method of embodiment P13, wherein X is chloro.

Embodiment P16

The method of embodiment P13, wherein said base is N-methylmorpholine or triethanolamine.

Embodiment P17

The method of embodiment P13 wherein said precipitate is crystalline.

Embodiment P18

The method of embodiment P13, wherein the precipitate of formula (I) is isolated as a salt.

Embodiment P19

The method of embodiment P18, wherein said salt is a hydrochloric acid salt, a di-hydrochloride acid salt, a hydrobromide salt, an alkylsulfonate salt, an acetate salt or a formate salt.

Embodiment P20

The method of embodiment P13, wherein the precipitate of formula (I) is isolated as a hydrochloric acid salt or a dihydrochloride salt.

Embodiment P21

The method of embodiment P13, wherein the precipitate of formula (I) is isolated as a free base.

Embodiment P22

The method of embodiment P19, wherein the precipitate of formula (I) is isolated by re-crystallization from a polar solvent.

Embodiment P23

The method of embodiment P22, wherein the polar solvent is a polar protic solvent or a polar aprotic solvent.

Embodiment P24

The method of embodiment P23, wherein said polar solvent is a polar protic solvent.

Embodiment P25

The method of embodiment P24, wherein said polar protic solvent is an alcohol.

Embodiment P26

The method of embodiment P25, wherein said alcohol is 2-proponol, ethanol or methanol.

Embodiment P27

The method of embodiment P21, wherein the precipitate of formula (I) is isolated by re-crystallization from methyl alcohol, trimethylsilyl chloride, hydrochloric acid, hydrogen chloride, or dimethylformamide.

Embodiment P28

The method of embodiment P23, wherein the precipitate of formula (I) is isolated by re-crystallization from hydrogen choride in an alcohol solvent or a non-alcoholic solvent.

Embodiment P29

The method of embodiment P23 wherein the precipitate of formula (I) is isolated by re-crystallization from hydrochloric acid.

Embodiment P30

The method of embodiment P13, wherein the method comprises the step of forming a compound of the formula (II):

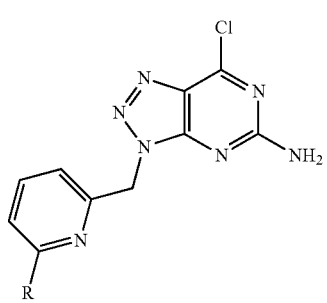

wherein R is as defined above, by:
(a) reacting the precipitate of formula (I) with a nitrite; and
(a) isolating the compound of formula (II).

Embodiment P31

The method of embodiment P30 wherein said nitrite is isoamyl nitrite or sodium nitrite.

Embodiment P32

The method of embodiment P30, wherein the precipitate of formula (I) is reacted with said nitrite at a pH of about 1.0 to about 7.0.

Embodiment P33

The method of embodiment P32 wherein the precipitate of formula (I) is reacted with said nitrite at a pH of about 1.0 to about 3.0.

Embodiment P34

The method of embodiment P30, wherein the compound of formula (II) is isolated as a salt.

Embodiment P35

The method of embodiment P34, wherein the compound of formula (II) is a hydrochloric acid salt, a di-hydrochloride acid salt, a hydrobromide salt, a di-hydrobromide salt, an alkylsulfonate salt, an acetate salt or a formate salt.

Embodiment P36

The method of embodiment P34, wherein the compound of formula (II) is isolated as a hydrochloric acid salt

Embodiment P37

The method of embodiment P30, wherein the compound of formula (II) is isolated as a free base.

Embodiment P38

The method of embodiment P37, wherein the step of isolating the compound of formula (II) is in the presence of a base.

Embodiment P39

The method of embodiment P38 wherein said base is a carbonate or a hydroxide.

Embodiment P40

The method of embodiment P39 wherein said base is a carbonate.

Embodiment P41

The method of embodiment P40 wherein said carbonate is sodium carbonate, sodium bicarbonate, potassium carbonate or potassium bicarbonate.

Embodiment P42

The method of embodiment P39 wherein said base is a hydroxide.

Embodiment P43

The method of embodiment P42 wherein said hydroxide is sodium hydroxide or potassium hydroxide.

Embodiment P44

The method of any one of embodiments P13-P38, wherein
$R^a$ and $R^b$ are independently H; and
$R^2$ is tetrahydrofuranyl.

Embodiment P45

The method of any one of embodiments P13-P38, wherein $R^a$ and $R^b$ are independently H.

Embodiment P46

The method of any of embodiments P13-P45, wherein R is

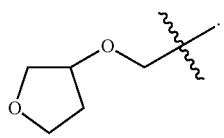

Embodiment P47

The method of embodiment P30, wherein said compound is isolated as a precipitate.

Embodiment P48

The method of embodiment P47, wherein said compound is crystalline.

Embodiment P49

The method of embodiment P13, wherein the precipitate of formula (I) is of the formula:

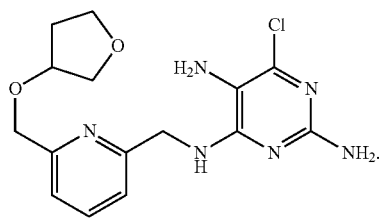 [SMILES: Nc1nc(Cl)c(N)c(NCc2cccc(COC3CCOC3)n2)n1]

Embodiment P50

The method of embodiment P30, wherein the compound of formula II is of the formula

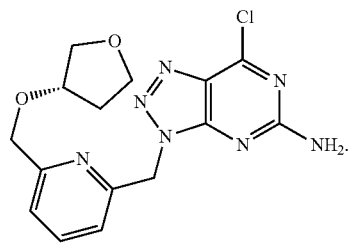 [SMILES: Nc1nc(Cl)c2nnn(Cc3cccc(CO[C@H]4CCOC4)n3)c2n1]

Embodiment P51

The method of embodiment P30, wherein the method comprises the step of forming a compound of formula (III):

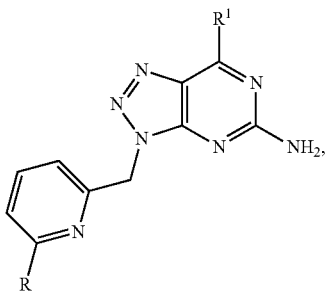

(III)

by:
(a) reacting a compound of formula (II) with a compound of the formula $R^1$—Y in the presence of a palladium catalyst and a base, wherein Y is a leaving group,
wherein, R is —$(CR^aR^b)$—O—$R^2$;
$R^a$ is H or alkyl;
$R^b$ is H or alkyl; or $R^a$ and $R^b$ together with the atom to which they are attached form a 3 to 8 membered saturated or partially saturated hydrocarbon ring or form a 4 to 8 membered saturated or partially saturated heterocylic ring comprising a ring member selected from O, N($R^3$) and S;
$R^1$ is phenyl or heteroaryl, wherein said phenyl or said heteroaryl group may be optionally substituted with alkyl, alkoxy, halo or —CN;
$R^2$ is H, alkyl, cycloalkyl or heterocycloalkyl, wherein said alkyl or cycloalkyl may optionally be substituted with halo, alkoxy or heterocycloalkyl;
$R^3$ is H or alkyl;
wherein, heteroaryl is a 5 or 6 membered aromatic ring, comprising one or two ring members selected from N, N($R^4$), S and O;
alkyl (or the alkyl group of the alkoxy group) is a linear or branched saturated hydrocarbon containing up to 10 carbon atoms;
alkoxy is a linear or branched saturated hydrocarbon containing up to 10 carbon atoms attached to the remainder of the molecule through an oxygen linker;
heterocycloalkyl is a C-linked or N-linked 3 to 10 membered non-aromatic, monocyclic ring, wherein said heterocycloalkyl ring comprises 1, 2 or 3 ring members independently selected from N, N($R^4$), S(O)$_q$ and O;
$R^4$ is H or alkyl; and
q is 0, 1 or 2; and
(b) isolating the compound of formula (III).

Embodiment P52

The method of embodiment P51, wherein Y is an organometallic leaving group.

Embodiment P53

The method of embodiment P52 wherein said organometallic leaving group is a boronate ester moiety or a boronic acid moiety.

Embodiment P54

The method of embodiment P53 wherein said organometallic leaving group is a boronate ester moiety.

Embodiment P55

The method of embodiment P51 wherein the compound of formula (III) is isolated by re-crystallization from an alcohol solvent, tetrahydrofuran, and water.

Embodiment P56

The method of embodiment P51, wherein the compound of formula (III) is isolated by re-crystallization from an alcohol solvent, 2-methyltetrahydrofuran, and water.

Embodiment P57

The method of embodiment P54 or P55, wherein said alcohol solvent is isopropanol.

Embodiment P58

The method of embodiment P51, wherein the base is an inorganic base.

Embodiment P59

The method of embodiment P58, wherein the inorganic base is potassium carbonate, potassium bicarbonate, sodium carbonate, sodium bicarbonate, cesium carbonate, sodium hydroxide, sodium ethoxide or sodium methoxide.

Embodiment P60

The method of embodiment P51, wherein the palladium catalyst is a palladium complex.

Embodiment P61

The method of embodiment P51, wherein the palladium catalyst is Pd(dtbpf)Cl$_2$, PdCl$_2$P(Ph$_3$)$_2$, PdP(Ph$_2$)$_4$, Pd(dppf)Cl$_2$, Pd(dippf)Cl$_2$ or Pd$_2$(dba)$_3$.

Embodiment P62

The method of embodiment P54, wherein the boronate ester moiety is pinacolborane, boronic acid, 2-(5-methylfuran-2-yl) catecholborane, 2-(5-methylfuran-2-yl)-1,3,2-dioxaborinane, diisopropyl (5-methylfuran-2-yl)boronate, (1s,5s)-9-(5-methylfuran-2-yl)-9-borabicyclo[3.3.1]nonane or (5-methylfuran-2-yl)boronic acid.

Embodiment P63

The method of embodiment P54, wherein the boronate ester moiety has the formula:

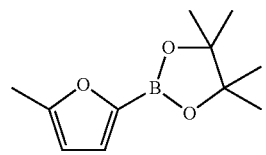

Embodiment P64

The method of embodiment P51, further comprising the step of contacting the palladium catalyst with a palladium scavenger.

Embodiment P65

The method of embodiment P64, wherein said palladium scavenger is a charcoal particle, a polymer-bound charcoal particle, a thiol moiety, a polymer-bound thiol moiety, an amine moiety, or a polymer-bound amine moiety.

Embodiment P66

The method of embodiment P65, wherein the charcoal particle is less than about 200μ, or less than about 150μ, or less than about 100μ, or less than about 75μ, or less than about 50μ, or less than about 25μ.

Embodiment P67

The method of embodiment P65 wherein said thiol moiety is cysteine.

Embodiment P68

The method of embodiment P65 wherein said polymer-bound thiol moiety is polymer-bound cysteine.

Embodiment P69

The method of embodiment P64, wherein the palladium scavenger is contained in a preformed device.

Embodiment P70

The method of embodiment P64 wherein the step of contacting the palladium catalyst with a palladium scavenger results in a reaction mixture comprising the compound of formula (III) having less than about 500 ppm residual palladium, or less than about 400 ppm residual palladium, or less than about 300 ppm residual palladium, or less than about 200 ppm residual palladium, or less than about 100 ppm residual palladium, or less than about 90 ppm residual palladium, or less than about 80 ppm residual palladium, or less than about 70 ppm residual palladium, or less than about 60 ppm residual palladium, or less than about 50 ppm residual palladium, or less than about 40 ppm residual palladium, or less than about 30 ppm residual palladium, or less than about 20 ppm residual palladium, or less than about 10 ppm residual palladium, or less than about 5 ppm residual palladium, or less than about 4 ppm residual palladium, or less than about 3 ppm residual palladium, or less than about 2 ppm residual palladium, or less than about 1 ppm residual palladium.

Embodiment P71

The method of embodiment P51 wherein said compound is isolated as a precipitate.

Embodiment P72

The method of embodiment P51 wherein the compound is crystalline.

Embodiment P73

The method of embodiment P51, wherein the compound of formula (III) is of the formula:

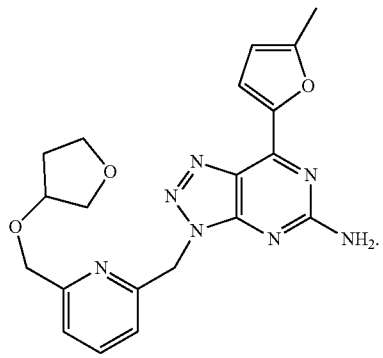 [SMILES: Cc1ccc(-c2nc(N)nc3c2nnn3Cc2cccc(COC3CCOC3)n2)o1]

FURTHER EMBODIMENTS

Embodiment 1

A precipitate of the formula (I):

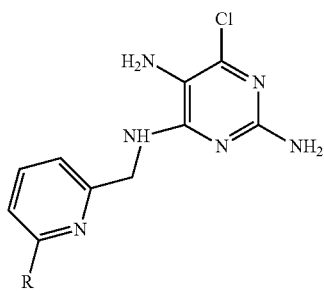

or a tautomer, stereoisomer, or pharmaceutically acceptable salt thereof, wherein:
R is —(CR$^a$R$^b$)—O—R$^2$;
R$^a$ is H or alkyl;
R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocylic ring comprising a ring member selected from O, N(R$^3$) and S;

R$^2$ is H, alkyl, cycloalkyl or heterocycloalkyl, wherein the alkyl or cycloalkyl may optionally be substituted with halo, alkoxy or heterocycloalkyl;
R$^3$ is H or alkyl;
wherein, heteroaryl is a 5 or 6 membered aromatic ring, comprising one or two ring members selected from N, N(R$^4$), S and O;
alkyl (or the alkyl group of the alkoxy group) is a linear or branched saturated hydrocarbon containing up to 10 carbon atoms;
alkoxy is a linear or branched saturated hydrocarbon containing up to 10 carbon atoms attached to the remainder of the molecule through an oxygen linker;
heterocycloalkyl is a C-linked or N-linked 3 to 10 membered non-aromatic, monocyclic ring, wherein said heterocycloalkyl ring comprises 1, 2 or 3 ring members independently selected from N, N(R$^4$), S(O)$_q$ and O;
R$^4$ is H or alkyl; and
q is 0, 1 or 2.

Embodiment 2

A precipitate of the formula (II):

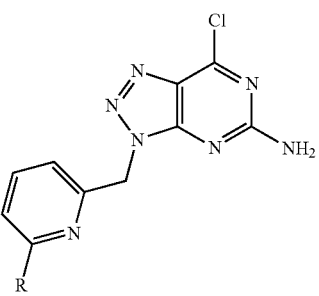

or a tautomer, stereoisomer, or pharmaceutically acceptable salt thereof, wherein:
R is —(CR$^a$R$^b$)—O—R$^2$;
R$^a$ is H or alkyl;
R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocylic ring comprising a ring member selected from O, N(R$^3$) and S;
R$^2$ is H, alkyl, cycloalkyl or heterocycloalkyl, wherein said alkyl or cycloalkyl may optionally be substituted with halo, alkoxy or heterocycloalkyl;
R$^3$ is H or alkyl;
wherein, heteroaryl is a 5 or 6 membered aromatic ring, comprising one or two ring members selected from N, N(R$^4$), S and O;
alkyl (or the alkyl group of the alkoxy group) is a linear or branched saturated hydrocarbon containing up to 10 carbon atoms;
alkoxy is a linear or branched saturated hydrocarbon containing up to 10 carbon atoms attached to the remainder of the molecule through an oxygen linker;
heterocycloalkyl is a C-linked or N-linked 3 to 10 membered non-aromatic, monocyclic ring, wherein said heterocycloalkyl ring comprises 1, 2 or 3 ring members independently selected from N, N(R$^4$), S(O)$_q$ and O;
R$^4$ is H or alkyl; and
q is 0, 1 or 2.

Embodiment 3

The precipitate of embodiment 1 or 2, wherein $R^a$ and $R^b$ are independently H; and $R^2$ is tetrahydrofuranyl.

Embodiment 4

The precipitate of embodiment 1 or 2, wherein $R^a$ and $R^b$ are independently H.

Embodiment 5

The precipitate of embodiment 1 or 2, wherein R is

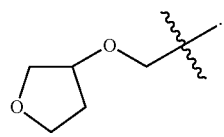

Embodiment 6

The precipitate of embodiment 1 or 2, which is a salt.

Embodiment 7

The precipitate of embodiment 6, wherein said precipitate is a hydrochloric acid salt, a di-hydrochloride acid salt, a hydrobromide salt, dihydromide salt, an alkylsulfonate salt, an acetate salt or a formate salt.

Embodiment 8

The precipitate of embodiment 7 wherein said precipitate is a hydrochloric acid salt or a dihydrochloride salt.

Embodiment 9

The precipitate of embodiment 1 or 2, wherein said precipitate is a free base.

Embodiment 10

The precipitate of embodiment 1 or 2, which is crystalline.

Embodiment 11

The precipitate of embodiment 1 of the formula:

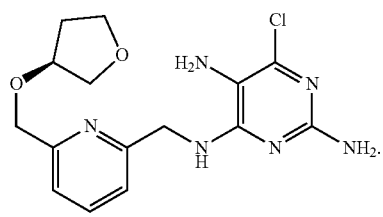 [SMILES: Nc1nc(Cl)c(N)c(NCc2cccc(CO[C@H]3CCOC3)n2)n1]

Embodiment 12

The precipitate of embodiment 1 of the formula:

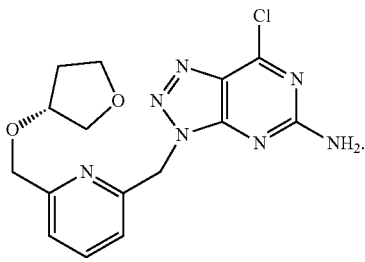 [SMILES: Nc1nc(Cl)c2nnn(Cc3cccc(CO[C@@H]4CCOC4)n3)c2n1]

Embodiment 13

A method of isolating a precipitate of the formula (I):

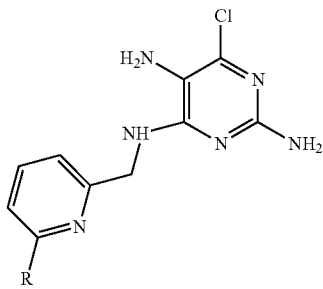

(I)

comprising the steps of:
(c) reacting a compound of the formula:

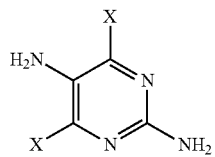

with a compound of the formula:

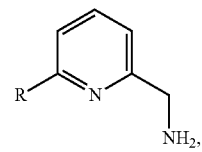

in the presence of a base;
wherein,
X is halo, and
wherein R is —(CR$^a$R$^b$)—O—R$^2$;
R$^a$ is H or alkyl;
R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocylic ring comprising a ring member selected from O, N(R$^3$) and S;

$R^2$ is H, alkyl, cycloalkyl or heterocycloalkyl, wherein said alkyl or cycloalkyl may optionally be substituted with halo, alkoxy or heterocycloalkyl;

$R^3$ is H or alkyl;

wherein, heteroaryl is a 5 or 6 membered aromatic ring, comprising one or two ring members selected from N, $N(R^4)$, S and O;

alkyl (or the alkyl group of the alkoxy group) is a linear or branched saturated hydrocarbon containing up to 10 carbon atoms;

alkoxy is a linear or branched saturated hydrocarbon containing up to 10 carbon atoms attached to the remainder of the molecule through an oxygen linker;

heterocycloalkyl is a C-linked or N-linked 3 to 10 membered non-aromatic, monocyclic ring, wherein said heterocycloalkyl ring comprises 1, 2 or 3 ring members independently selected from N, $N(R^4)$, $S(O)_q$ and O;

$R^4$ is H or alkyl; and q is 0, 1 or 2; and (d) isolating the precipitate of formula (I).

Embodiment 14

The method of embodiment 13, wherein X is chloro, fluoro or bromo, iodo or alkylsulfonate.

Embodiment 15

The method of embodiment 13, wherein X is chloro.

Embodiment 16

The method of embodiment 13, wherein said base is N-methylmorpholine or triethanolamine.

Embodiment 17

The method of embodiment 13 wherein said precipitate is crystalline.

Embodiment 18

The method of embodiment 13, wherein the precipitate of formula (I) is isolated as a salt.

Embodiment 19

The method of embodiment 18, wherein said salt is a hydrochloric acid salt, a di-hydrochloride acid salt, a hydrobromide salt, an alkylsulfonate salt, an acetate salt or a formate salt.

Embodiment 20

The method of embodiment 13, wherein the precipitate of formula (I) is isolated as a hydrochloric acid salt or a dihydrochloride salt.

Embodiment 21

The method of embodiment 13, wherein the precipitate of formula (I) is isolated as a free base.

Embodiment 22

The method of embodiment 19, wherein the precipitate of formula (I) is isolated by re-crystallization from a polar solvent.

Embodiment 23

The method of embodiment 22, wherein the polar solvent is a polar protic solvent or a polar aprotic solvent.

Embodiment 24

The method of embodiment 23, wherein said polar solvent is a polar protic solvent.

Embodiment 25

The method of embodiment 24, wherein said polar protic solvent is an alcohol.

Embodiment 26

The method of embodiment 25, wherein said alcohol is 2-proponol, ethanol or methanol.

Embodiment 27

The method of embodiment 21, wherein the precipitate of formula (I) is isolated by re-crystallization from methyl alcohol, trimethylsilyl chloride, hydrochloric acid, hydrogen chloride, or dimethylformamide.

Embodiment 28

The method of embodiment 23, wherein the precipitate of formula (I) is isolated by re-crystallization from hydrogen choride in an alcohol solvent or a non-alcoholic solvent.

Embodiment 29

The method of embodiment 23 wherein the precipitate of formula (I) is isolated by re-crystallization from hydrochloric acid.

Embodiment 30

The method of embodiment 13, wherein the method comprises the step of forming a compound of the formula (II):

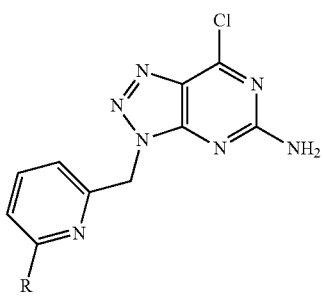

wherein R is as defined above, by:
 (a) reacting the precipitate of formula (I) with a nitrite; and
 (b) isolating the compound of formula (II).

Embodiment 31

The method of embodiment 30 wherein said nitrite is isoamyl nitrite or sodium nitrite.

Embodiment 32

The method of embodiment 30, wherein the precipitate of formula (I) is reacted with said nitrite at a pH of about 1.0 to about 7.0.

Embodiment 33

The method of embodiment 32 wherein the precipitate of formula (I) is reacted with said nitrite at a pH of about 1.0 to about 3.0.

Embodiment 34

The method of embodiment 30, wherein the compound of formula (II) is isolated as a salt.

Embodiment 35

The method of embodiment 34, wherein the compound of formula (II) is a hydrochloric acid salt, a di-hydrochloride acid salt, a hydrobromide salt, a di-hydrobromide salt, an alkylsulfonate salt, an acetate salt or a formate salt.

Embodiment 36

The method of embodiment 34, wherein the compound of formula (II) is isolated as a hydrochloric acid salt Embodiment 37

The method of embodiment 30, wherein the compound of formula (II) is isolated as a free base.

Embodiment 38

The method of embodiment 37, wherein the step of isolating the compound of formula (II) is in the presence of a base.

Embodiment 39

The method of embodiment 38 wherein said base is a carbonate or a hydroxide.

Embodiment 40

The method of embodiment 39 wherein said base is a carbonate.

Embodiment 41

The method of embodiment 40 wherein said carbonate is sodium carbonate, sodium bicarbonate, potassium carbonate or potassium bicarbonate.

Embodiment 42

The method of embodiment 39 wherein said base is a hydroxide.

Embodiment 43

The method of embodiment 42 wherein said hydroxide is sodium hydroxide or potassium hydroxide.

Embodiment 44

The method of any one of embodiments 13-38, wherein $R^a$ and $R^b$ are independently H; and
$R^2$ is tetrahydrofuranyl.

Embodiment 45

The method of any one of embodiments 13-38, wherein $R^a$ and $R^b$ are independently H.

Embodiment 46

The method of any of embodiments 13-45, wherein R is

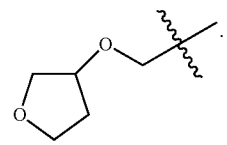

Embodiment 47

The method of embodiment 30, wherein said compound is isolated as a precipitate.

Embodiment 48

The method of embodiment 47, wherein said compound is crystalline.

Embodiment 49

The method of embodiment 13, wherein the precipitate of formula (I) is of the formula:

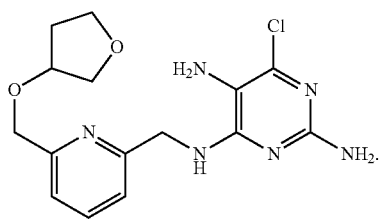 [SMILES: Nc1nc(Cl)c(N)c(NCc2cccc(COC3CCOC3)n2)n1]

Embodiment 50

The method of embodiment 30, wherein the compound of formula II is of the formula:

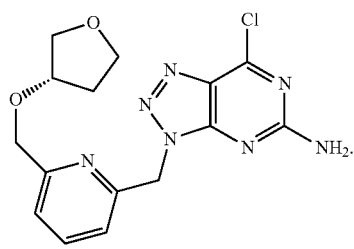 [SMILES: Nc1nc(Cl)c2nnn(Cc3cccc(CO[C@H]4CCOC4)n3)c2n1]

Embodiment 51

The method of embodiment 30, wherein the method comprises the step of forming a compound of formula (III):

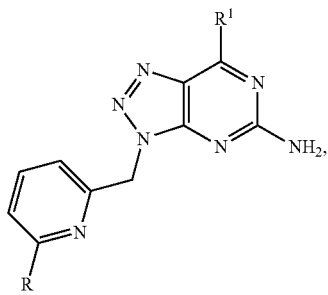

(III)

by:
(b) reacting a compound of formula (II) with a compound of the formula $R^1$—Y in the presence of
  a palladium catalyst and a base, wherein Y is a leaving group,
wherein, R is —$(CR^aR^b)$—O—$R^2$;
$R^a$ is H or alkyl;
$R^b$ is H or alkyl; or $R^a$ and $R^b$ together with the atom to which they are attached form a 3 to 8 membered saturated or partially saturated hydrocarbon ring or form a 4 to 8 membered saturated or partially saturated heterocylic ring comprising a ring member selected from O, $N(R^3)$ and S;
$R^1$ is phenyl or heteroaryl, wherein said phenyl or said heteroaryl group may be optionally substituted with alkyl, alkoxy, halo or —CN;
$R^2$ is H, alkyl, cycloalkyl or heterocycloalkyl, wherein said alkyl or cycloalkyl may optionally be substituted with halo, alkoxy or heterocycloalkyl;
$R^3$ is H or alkyl;
wherein, heteroaryl is a 5 or 6 membered aromatic ring, comprising one or two ring members selected from N, $N(R^4)$, S and O;
alkyl (or the alkyl group of the alkoxy group) is a linear or branched saturated hydrocarbon containing up to 10 carbon atoms;
alkoxy is a linear or branched saturated hydrocarbon containing up to 10 carbon atoms attached to the remainder of the molecule through an oxygen linker;
heterocycloalkyl is a C-linked or N-linked 3 to 10 membered non-aromatic, monocyclic ring, wherein said heterocycloalkyl ring comprises 1, 2 or 3 ring members independently selected from N, $N(R^4)$, $S(O)_q$ and O;
$R^4$ is H or alkyl; and
q is 0, 1 or 2; and
(b) isolating the compound of formula (III).

Embodiment 52

The method of embodiment 51, wherein Y is an organometallic leaving group.

Embodiment 53

The method of embodiment 52 wherein said organometallic leaving group is a boronate ester moiety or a boronic acid moiety.

Embodiment 54

The method of embodiment 53 wherein said organometallic leaving group is a boronate ester moiety.

Embodiment 55

The method of embodiment 51 wherein the compound of formula (III) is isolated by re-crystallization from an alcohol solvent, tetrahydrofuran, and water.

Embodiment P6

The method of embodiment 51, wherein the compound of formula (III) is isolated by re-crystallization from an alcohol solvent, 2-methyltetrahydrofuran, and water.

Embodiment 57

The method of embodiment 54 or 55, wherein said alcohol solvent is isopropanol.

Embodiment 58

The method of embodiment 51, wherein the base is an inorganic base.

Embodiment 59

The method of embodiment 58, wherein the inorganic base is potassium carbonate, potassium bicarbonate, sodium carbonate, sodium bicarbonate, cesium carbonate, sodium hydroxide, sodium ethoxide or sodium methoxide.

Embodiment 60

The method of embodiment 51, wherein the palladium catalyst is a palladium complex.

Embodiment 61

The method of embodiment 51, wherein the palladium catalyst is $Pd(dtbpf)Cl_2$, $PdCl_2P(Ph_3)_2$, $PdP(Ph_2)_4$, $Pd(dppf)Cl_2$, $Pd(dippf)Cl_2$ or $Pd_2(dba)_3$.

Embodiment 62

The method of embodiment 54, wherein the boronate ester moiety is pinacolborane, boronic acid, 2-(5-methylfuran-2-yl) catecholborane, 2-(5-methylfuran-2-yl)-1,3,2-dioxaborinane, diisopropyl (5-methylfuran-2-yl)boronate, (1s,5s)-9-(5-methylfuran-2-yl)-9-borabicyclo[3.3.1]nonane or (5-methylfuran-2-yl)boronic acid.

Embodiment 63

The method of embodiment 54, wherein the boronate ester moiety has the formula:

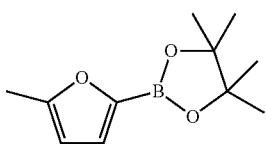

Embodiment 64

The method of embodiment 51, further comprising the step of contacting the palladium catalyst with a palladium scavenger.

Embodiment 65

The method of embodiment 64, wherein said palladium scavenger is a charcoal particle, a polymer-bound charcoal particle, a thiol moiety, a polymer-bound thiol moiety, an amine moiety, or a polymer-bound amine moiety.

Embodiment 66

The method of embodiment 65, wherein the charcoal particle is less than about 200μ, or less than about 150μ, or less than about 100μ, or less than about 75μ, or less than about 50μ, or less than about 25μ.

Embodiment 67

The method of embodiment 65 wherein said thiol moiety is cysteine.

Embodiment 68

The method of embodiment 65 wherein said polymer-bound thiol moiety is polymer-bound cysteine.

Embodiment 69

The method of embodiment 64, wherein the palladium scavenger is contained in a preformed device.

Embodiment 70

The method of embodiment 64 wherein the step of contacting the palladium catalyst with a palladium scavenger results in a reaction mixture comprising the compound of formula (III) having less than about 500 ppm residual palladium, or less than about 400 ppm residual palladium, or less than about 300 ppm residual palladium, or less than about 200 ppm residual palladium, or less than about 100 ppm residual palladium, or less than about 90 ppm residual palladium, or less than about 80 ppm residual palladium, or less than about 70 ppm residual palladium, or less than about 60 ppm residual palladium, or less than about 50 ppm residual palladium, or less than about 40 ppm residual palladium, or less than about 30 ppm residual palladium, or less than about 20 ppm residual palladium, or less than about 10 ppm residual palladium, or less than about 5 ppm residual palladium, or less than about 4 ppm residual palladium, or less than about 3 ppm residual palladium, or less than about 2 ppm residual palladium, or less than about 1 ppm residual palladium.

Embodiment 71

The method of embodiment 51 wherein said compound is isolated as a precipitate.

Embodiment 72

The method of embodiment 51 wherein the compound is crystalline.

Embodiment 73

The method of embodiment 51, wherein the compound of formula (III) is of the formula:

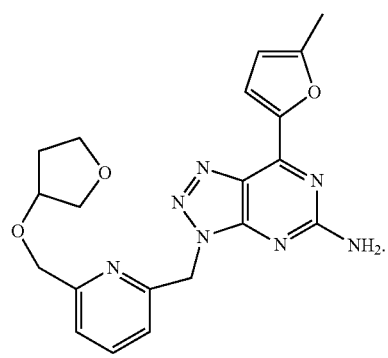 [SMILES: Cc1ccc(-c2nc(N)nc3c2nnn3Cc2cccc(COC3CCOC3)n2)o1]

Embodiment 74

A compound of formula (V):

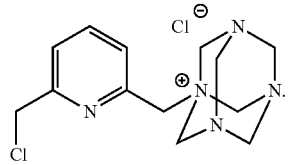 [SMILES: ClCc1cccc(C[N+]23CN4CN(CN(C4)C2)C3)n1 ; [Cl-]]

(V)

Embodiment 75

A method of synthesis of the compound of formula (V):

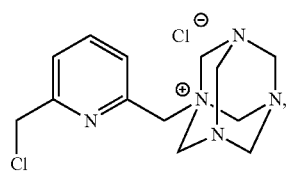

comprising reacting a compound of formula:

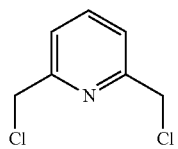

with hexamethylenetetraamine (HMTA) of formula

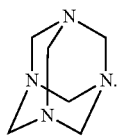

Embodiment 76

The embodiment of claim 76, further comprising forming the compound of formula:

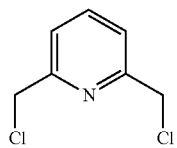

by reacting the compound of formula

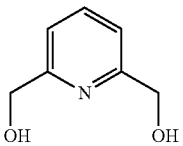

with a chlorinating agent in the presence of organic solvent.

Embodiment 77

The method of embodiment 76, wherein the chlorinating agent is thionyl chloride.

Embodiment 78

The method of embodiment 76, wherein the organic solvent is dichloromethane.

Embodiment 79

The method of embodiment 76, further comprising forming the compound of formula

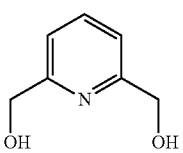

by:
(a) reacting a compound of formula

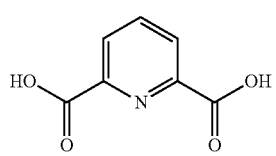

with inorganic acid in the presence of alcohol thereby providing a compound of formula

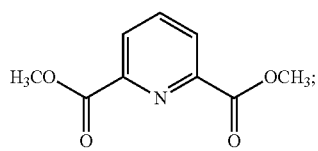 [SMILES: COC(=O)c1cccc(C(=O)OC)n1]

and
(b) reacting the compound of formula

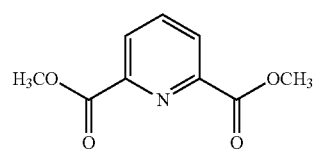 [SMILES: COC(=O)c1cccc(C(=O)OC)n1]

with a reducing agent in the presence of alcohol and a catalyst thereby forming the compound of formula

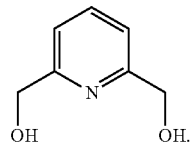

Embodiment 80

The method of embodiment 79, wherein the inorganic acid is sulfuric acid.

Embodiment 81

The method of embodiment 79, wherein the reducing agent is sodium borohydride.

Embodiment 82

The method of embodiment 79, wherein the alcohol is isopropanol, ethanol or methanol.

Embodiment 83

The method of embodiment 79, wherein the catalyst is lithium aluminium hydride.

Embodiment 84

The method of embodiment 79, further comprising the step of forming a compound of formula:

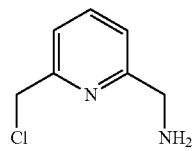

by reacting the compound of formula (V):

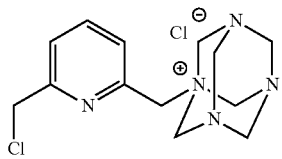 [SMILES: ClCc1cccc(C[N+]23CN4CN(CN(C4)C2)C3)n1 ; [Cl-]]

with alcohol in the presence of inorganic acid thereby forming a compound of formula

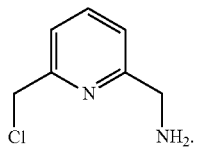

Embodiment 85

The method of embodiment 84, wherein the inorganic acid is hydrochloric acid.

Embodiment 86

The method of embodiment 84, wherein the alcohol is isopropanol, ethanol or methanol.

Embodiment 87

The method of embodiment 84, further comprising the step of forming a compound of formula:

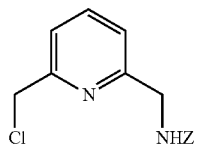

by reacting the compound of formula

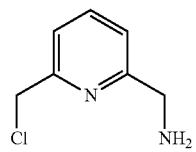

with
Boc$_2$O or CbzCl in the presence of organic solvent;
wherein Z is butyloxycarbonyl (Boc) or cabroxybenzyl (Cbz), thereby forming the compound formula

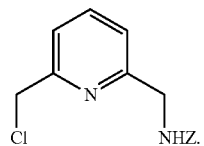

Embodiment 88

The method of embodiment 87, wherein the organic solvent is dichloromethane.

Embodiment 89

The method of embodiment 87, further comprising the step of forming a compound of formula:

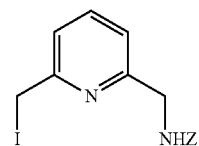

by reacting the compound of formula

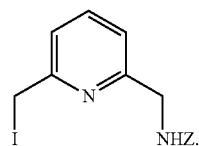

with an ionic compound in the presence of organic solvent;
wherein Z is butyloxycarbonyl (Boc) or cabroxybenzyl (Cbz), thereby forming the compound of formula

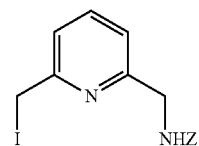

Embodiment 90

The method of embodiment 89, wherein the ionic compound is sodium iodide.

Embodiment 91

The method of embodiment 89, wherein the organic solvent is tetrahydrofuran.

Embodiment 92

The method of embodiment 89, further comprising the step of forming a compound of formula:

by reacting the compound of formula

[structure: pyridine with CH2-O-tetrahydrofuran-3-yl and CH2-NHZ]

with a compound of formula

[structure: 2,6-bis(CH2) pyridine with I and NHZ]

with a compound of formula

[structure: 3-hydroxytetrahydrofuran with OH]

in the presence of an organic solvent and catalyst, thereby forming the compound of formula

[structure: pyridine with CH2-O-tetrahydrofuran-3-yl and CH2-NHZ]

wherein Z is butyloxycarbonyl (Boc) or cabroxybenzyl (Cbz).

Embodiment 93

The method of embodiment 92, wherein the organic solvent is tetrahydrofuran or toluene.

Embodiment 94

The method of embodiment 92, wherein the catalyst is potassium t-butoxide.

Embodiment 95

The method of embodiment 92, further comprising the step of forming a compound of formula:

by reacting the compound of formula

[structure: pyridine with CH2-O-tetrahydrofuran-3-yl and CH2-NH2]

by reacting the compound of formula

[structure: pyridine with CH2-O-tetrahydrofuran-3-yl and CH2-NHZ]

with an organic acid in the presence of organic solvent, thereby forming the compound of formula

[structure: pyridine with CH2-O-tetrahydrofuran-3-yl and CH2-NH2]

Embodiment 96

The method of embodiment 95, wherein the organic acid is methanesulfonic acid.

Embodiment 97

The method of embodiment 95, the organic solvent is dichloromethane.

Embodiment 98

The method of embodiment 95, further comprising the step of forming a compound of formula (VI):

[structure: pyridine with CH2-O-tetrahydrofuran-3-yl and CH2-NH2 · 1/2 oxalic acid]

by reacting the compound of formula

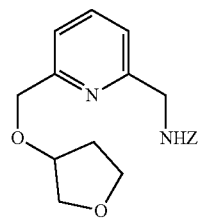

with an oxalic acid in the presence of organic solvent, thereby forming the compound of formula (VI):

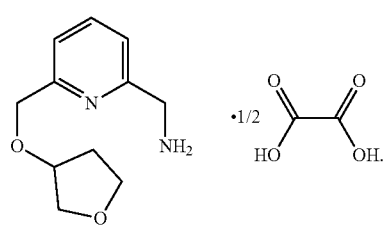 [SMILES: NCc1cccc(COC2CCOC2)n1 ; O=C(O)C(=O)O]

Embodiment 99

The method of embodiment 98, wherein the organic solvent is alcohol.

Embodiment 100

The method of embodiment 98, wherein the alcohol is isopropanol, ethanol or methanol.

Embodiment 101

A compound of formula (VII):

(VII)

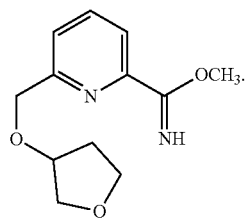 [SMILES: COC(=N)c1cccc(COC2CCOC2)n1]

Embodiment 102

A method of synthesis of the compound of formula (VII):

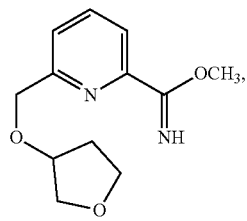

comprising the step of reacting a compound of formula

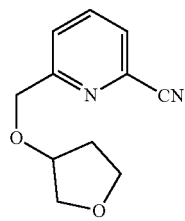 [SMILES: N#Cc1cccc(COC2CCOC2)n1]

with a methoxide, thereby forming a compound of formula

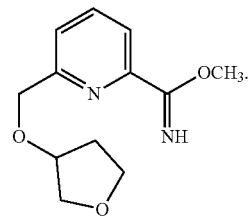 [SMILES: COC(=N)c1cccc(COC2CCOC2)n1]

Embodiment 103

The method of embodiment 102, wherein the basic reagent is sodium methoxide.

Embodiment 104

The method of embodiment 102, further comprising the step of forming of the compound of formula

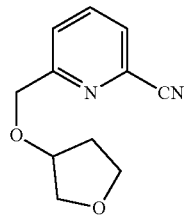 [SMILES: N#Cc1cccc(COC2CCOC2)n1]

by reacting a compound of formula

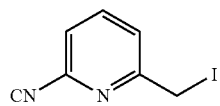

with a compound of formula

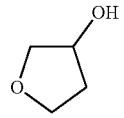

in the presence of a base thereby forming the compound of formula

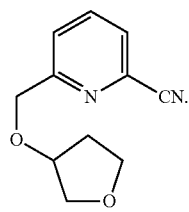 [SMILES: N#Cc1cccc(COC2CCOC2)n1]

Embodiment 105

The method of embodiment 104, further comprising the step of forming the compound of formula

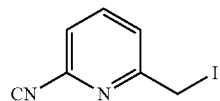

by reacting a compound of formula

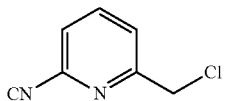

with a iodine salt in the presence of an organic solvent, thereby forming the compound of formula

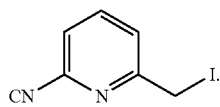

Embodiment 106

The method of embodiment 105, wherein the ionic compound is sodium iodide.

Embodiment 107

The method of embodiment 105, wherein the organic solvent is tetrahydrofuran.

Embodiment 108

The method of embodiment 105, further comprising the step of forming the compound of formula

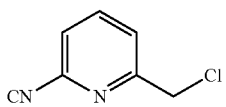

by reacting a compound of formula

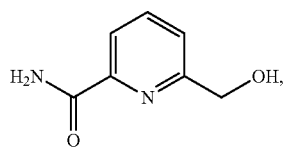

thereby forming the compound of formula

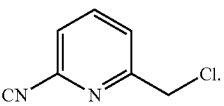

Embodiment 109

The method of embodiment 108, wherein the forming of the compound of formula

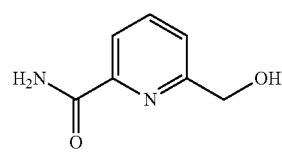 [SMILES: NC(=O)c1cccc(CO)n1]

is performed in the presence of phosphoryl chloride.

Embodiment 110

The method of embodiment 108, further comprising the step of forming the compound of formula

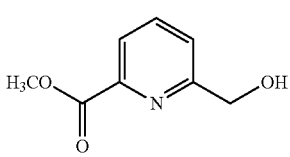 [SMILES: COC(=O)c1cccc(CO)n1]

by reacting a compound of formula

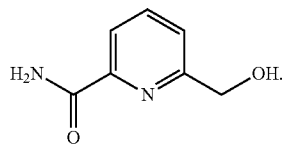

with an ammonium base, thereby forming the compound of formula

Embodiment 111

The method of embodiment 110, wherein the base is ammonium hydroxide

Embodiment 112

The method of embodiment 110, further comprising the step of forming the compound of formula

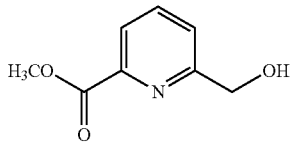 [SMILES: COC(=O)c1cccc(CO)n1]

by reacting a compound of formula

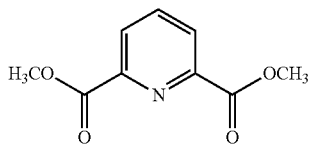 [SMILES: COC(=O)c1cccc(C(=O)OC)n1]

with a reducing agent, thereby forming the compound of formula

Embodiment 113

The method of embodiment 112, wherein the reducing agent is sodium borohydride.

Embodiment 114

The method of embodiment 112, further comprising the step of forming the compound of formula:

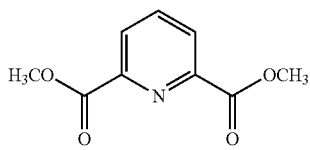 [SMILES: COC(=O)c1cccc(C(=O)OC)n1]

by reacting a compound of formula

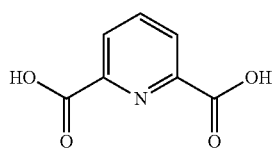

with a methylating agent, thereby forming the compound of formula

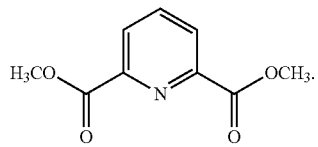 [SMILES: COC(=O)c1cccc(C(=O)OC)n1]

Embodiment 115

The method of embodiment 114, wherein the methylating agent is alcohol.

Embodiment 116

The method of embodiment 114, wherein the alcohol is methanol.

Embodiment 117

The method of embodiment 114, further comprising the step of forming the compound of formula:

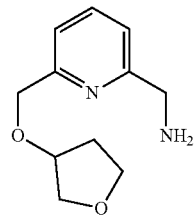 [SMILES: NCc1cccc(COC2CCOC2)n1]

by reacting the compound of formula (VII)

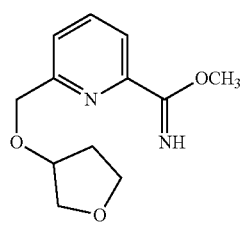 [SMILES: COC(=N)c1cccc(COC2CCOC2)n1]

with a transition metal.

Embodiment 118

The method of embodiment 117, wherein the transition metal is iron, cobalt, copper, zinc, or nickel.

Embodiment 119

The method of embodiment 117, further comprising the step of forming the compound of formula (VI):

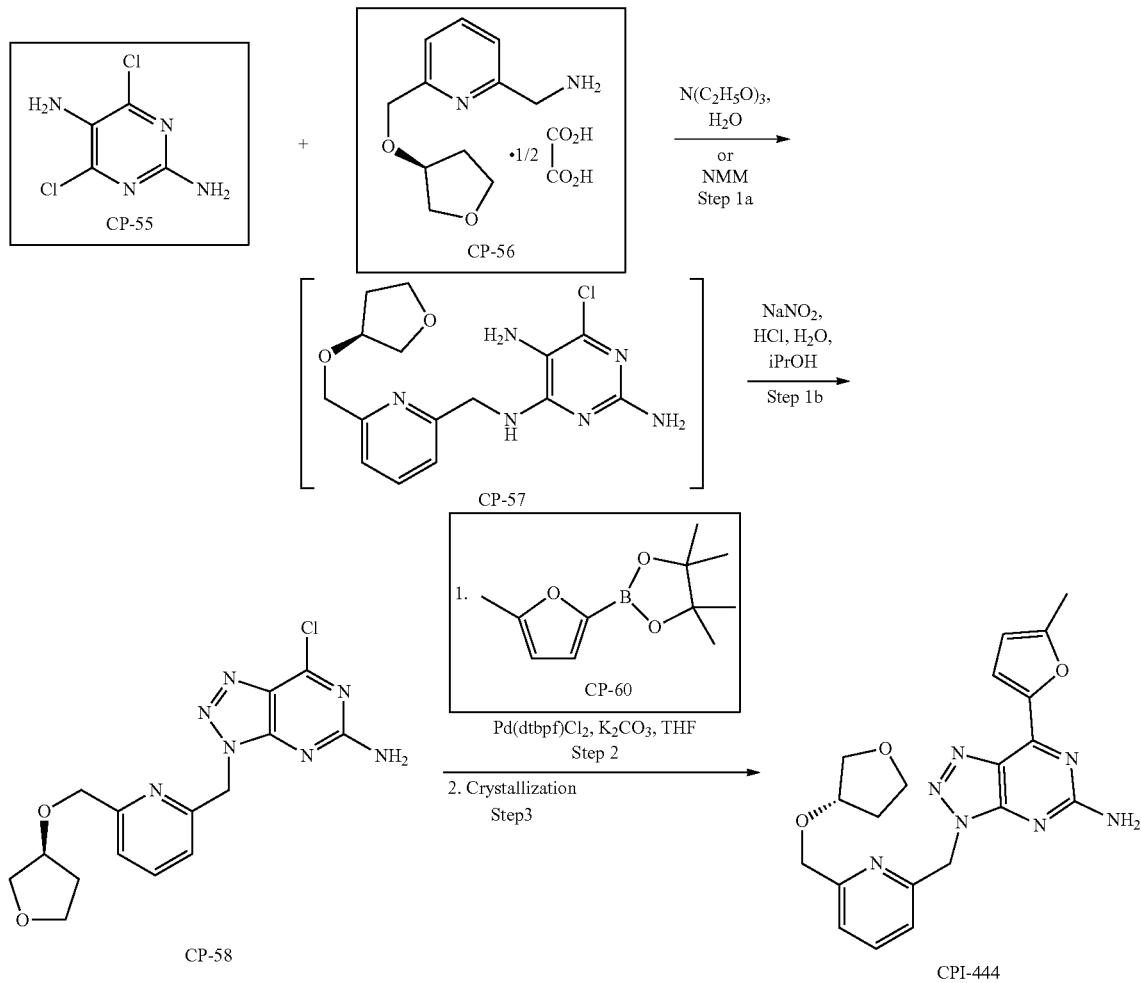

by reacting the compound of formula

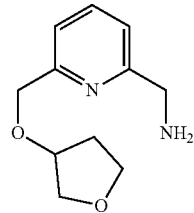 [SMILES: NCc1cccc(COC2CCOC2)n1]

with oxalic acid in the presence of organic solvent.

Embodiment 120

The method of embodiment 119, wherein the organic solvent is alcohol.

Embodiment 121

The method of embodiment 120, wherein the alcohol is isopropanol, ethanol or methanol.

Embodiment 122

The method of embodiment 51, further comprising 1,3-diaminopropane or ethylenediamine.

EXAMPLES

85

Referring to Reaction Scheme 1, the process to manufacture triazolo[4,5]pyramidine derivatives and intermediates thereof in accordance with the present disclosure, such as the compound known as CPI-444, consists of three chemical steps and uses starting materials known as CP-55, CP-56 and CP-60. The intermediate known as CP-57 is formed at step 1a without isolation (telescoped) and taken to the next step to form the compound known as CP-58 at step 1b. Suzuki coupling using CP-60 during step 2 generates crude CPI-444 which undergoes crystallization during step 3 to form CPI-444.

Previously described processes for making triazolo[4,5]pyramidine derivatives and intermediates thereof utilized a compound known as CP-59:

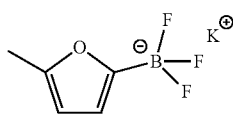

CP-59

Moreover, such previously described process utilize triethylamine which takes a longer time for the layers to separate where excessive rag layer is observed during phase separation.

86

The present inventors unexpectedly and surprisingly found that the replacement of CP-59 with CP-60 improved ease of handling and improved process efficiency. In addition, the present inventors unexpectedly and surprisingly found that the use of potassium carbonate ($K_2CO_3$) during step 2 improves the phase separation and minimizes rag layer formation upon reaction completion. Finally, Step 3 employs the use of thermocycler in order to facilitate the removal of residual solvents such as isopropyl alcohol.

Accordingly, the processes in accordance with the teachings of the present disclosure are an improvement over, and are more suitable for commercial scale-up, than processes previously described.

Starting material (C-55) is commercially available through Astatech, Inc., Keystone Business Park, 2525 Pearl Buck Road, Bristol, Pa., 19007, USA; or Suven, SDE Serene Chambers, Road No. 5, Avenue 7 Banjara Hills, Hyderabad, 500034, India.

CP-60 is commercially available through ARK Pharma, Inc., 3860 North Ventura Drive, Arlington Heights, Ill., 60004, USA; or Boron Technology Institute, Road No. 2, Building No. 10, room No. 259, Haidian District, Beijing, China.

Example 1. Preparation of CP-56

Reaction Scheme 1

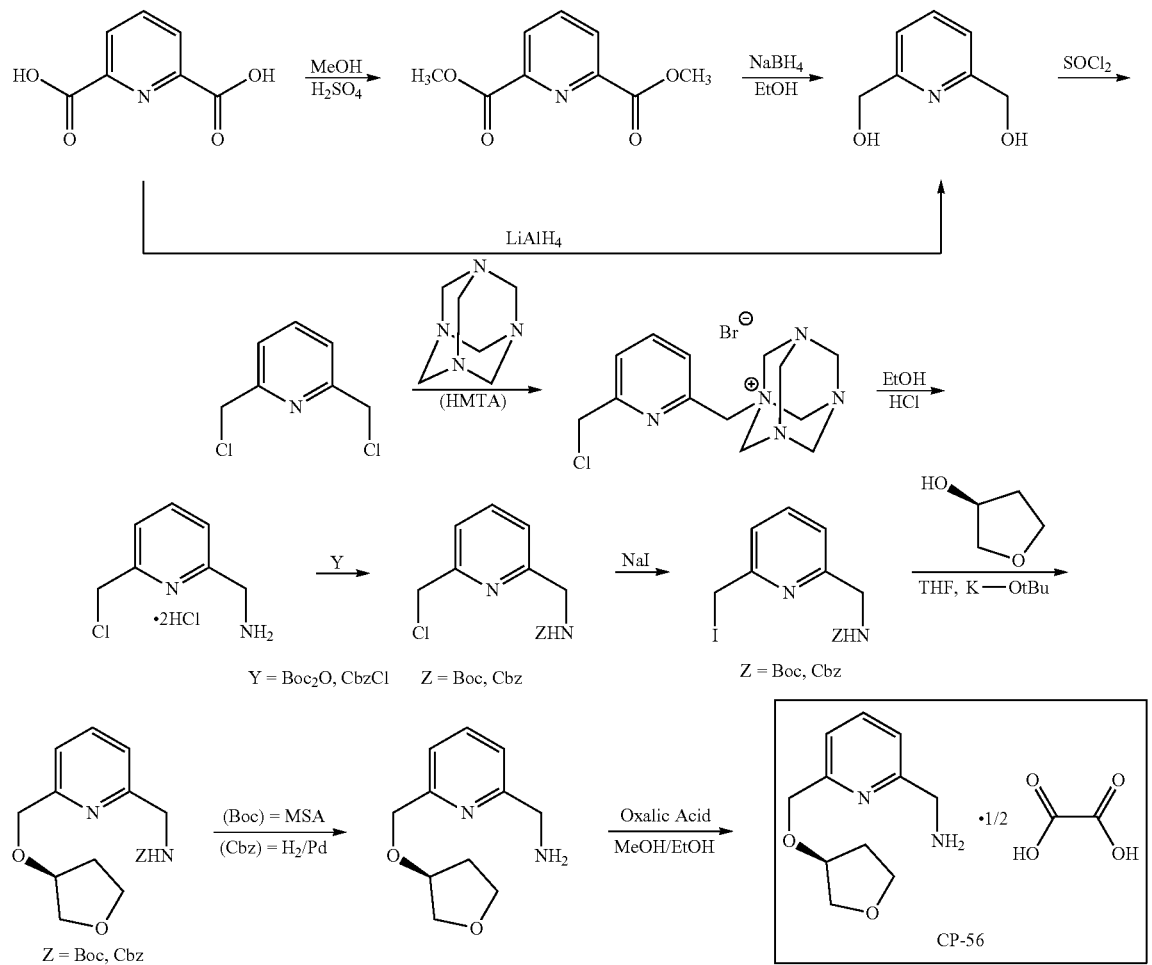

Preparation of Dimethyl pyridine-2,6-dicarboxylate

Pyridine-2,6-dicarboxylic acid (900 g, 1 eq) is suspended in methanol (5 volume) and added $H_2SO_4$. (19 g). The mixture is heated to reflux for approximately 4 hr. After reaction completion, the mixture is cooled to 5-10° C. to allow the solids to precipitate. The solids are stirred for an additional hour. The solids are collected by filtration. The wet-cake is re-dissolved in DCM (3 volume) and extract in sequence with an aqueous saturated solution of $NaHCO_3$ (2 Volume) followed by with a 5% brine solution (2 Volume). The organic layer is concentrated to dryness to obtain dimethyl pyridine-2,6-dicarboxylate; 914.85 g, purity 100%, yield 87.%.

Preparation of pyridine-2,6-diyldimethanol

Dimethyl pyridine-2,6-dicarboxylate (885 g, 1 eq) is dissolved in EtOH (4425 g, 5 Volume) at room temperature. The $NaBH_4$ (341 g, 2 eq) is added slowly to the reaction while keeping the internal temperature below 30° C. using an ice bath. The reaction is heated to 35° C. for approximately 2 hrs. After reaction completion, the mixture is cooled to room temperature and adjusted with 32% HCl solution to pH value of approximately 2.5. The mixture is stirred for 2 hrs to allow the solids to precipitate. The mixture is then adjusted pH value of approximately 9 using 30% NaOH solution while maintaining an internal temperature below 30° C. and stirred at room temperature for about 30 min. The solids are removed by filtration. The filtrate is concentrated at 50° C. The concentrated residual is suspended with isopropanol (4160 g, 8 vol)/water (416 g, 0.8 vol) and heated to 70° C. for about 1 hr. The solution is then cooled to room temperature and stirred for 2 hr before cooling to 5-10° C. for 30 min. The un-dissolved solids are removed by filtration. The filtrate is concentrated at 50° C. The concentrated residue is charged with dichloromethane (2700 g, 5 vol) and heated to 40° C. for 30 min. The suspension is cooled to 5-10° C. and stirred for 30 mins. The solid is collected by filtration and dried under vacuum at 40° C. to obtain pyridine-2,6-diyldimethanol; 540.77 g, purity 100%, yield 85.86%.

Preparation of 2,6-bis(chloromethyl)pyridine 2,6-bis(chloromethyl)pyridine (400 g, 1 eq) is suspended in DCM (2000 g) and then cooled to 10-15° C. Thionyl chloride ($SOCl_2$; 775 g, 3 eq) is charged with $CH_2Cl_2$ (775 g) and then added drop-wised into the reaction vessel while maintaining the internal temperature below 20° C. The reaction is then warmed to room temperature and held for approximately 2 hrs. After reaction completion, the 15% aqueous solution of $Na_2CO_3$ (9038 g) is pre-cooled to 10-15° C. before charging the reaction mixture into the carbonate solution while maintaining internal temperature below 20° C. The mixture is stirred until gas-evolution is no longer observed. The organic layer is extracted with water (2×3200 g) and then concentrated at 50° C. to a crude product. The concentrated crude is purified by recrystallization using heptane (946 g). The mixture is cooled to 5-10° C. for 30 min. The solid is collected by filtration and wet-cake is washed with heptane and dried at 40° C. under vacuum to obtain 2,6-bis(chloromethyl)pyridine; 442.6 g, purity 100%, yield 87.0%.

Preparation of (3r,5r,7r)-1-((6-(chloromethyl)pyridin-2-yl)methyl)-1,3,5,7-tetraazaadamantan-1-ium 2,6-bis(chloromethyl)pyridine (420 g, 1 eq) is dissolved in $CH_2Cl_2$ (8400 g), HMTA (336 g, 1 eq) is added into the reaction vessel. The reaction is heated to approximately 40° C. for about 3 hrs. Additional HMTA (168 g, 0.5 eq) is added into the reaction mixture and stirred overnight at room temperature. The product is collected by filtration. The wet-cake is washed with $CH_2Cl_2$ and dried under vacuum at 50° C. to obtain (3r,5r,7r)-1-((6-(chloromethyl)pyridin-2-yl)methyl)-1,3,5,7-tetraazaadamantan-1-ium; 730 g, purity 97.01%, yield 96.58%.

Preparation of (6-(chloromethyl)pyridin-2-yl)methanamine Dihydrochloride (3r,5r,7r)-1-((6-(chloromethyl)pyridin-2-yl)methyl)-1,3,5,7-tetraazaadamantan-1-ium (730 g, 1 eq) is suspended in EtOH (4380 g) before charging 37% HCl (159 g). The mixture is heated to approximately 60° C. for about 1 hr. After reaction completion, it is cooled to 25° C. MTBE (1200 g) is charged into the suspension. The suspension is then stirred for about 30 min and cooled to 5-10° C. for about 1 hr. The solids are collected by filtration and washed with MTBE and dried at 50° C. under vacuum to obtain (6-(chloromethyl)pyridin-2-yl)methanamine dihydrochloride; 449.56 g (after assay correction), purity 98.15%, yield 85.23%.

Preparation of tert-butyl ((6-(chloromethyl)pyridin-2-yl)methyl)carbamate (6-(chloromethyl)pyridin-2-yl)methanamine dihydrochloride [422.56 g (after assay correction), 1 eq] is dissolved in $CH_2Cl_2$ (5600 g) and pre-cooled to 10-15° C. $K_2CO_3$ (1632 g) pre-dissolved in water (4000 g) is charged into the reaction solution. The mixture is stirred for about 10 min and then cooled to 10-15° C. Boc-anhydride (603 g) is pre-dissolved in $CH_2Cl_2$ (1808 g) before charging into the reactor. The mixture is warmed to room temperature and held for about an hour. After reaction completion, the organic layer is extracted with water (4000 g), The organic layer is concentrated to dryness at 50° C. to obtain tert-butyl ((6-(chloromethyl)pyridin-2-yl)methyl)carbamate; 382.93 g [after assay correction); purity 99.01%; yield 81%].

Preparation of tert-butyl ((6-(iodomethyl)pyridin-2-yl)methyl)carbamate tert-butyl ((6-(chloromethyl)pyridin-2-yl)methyl)carbamat [382.93 g (after assay correction), 1 eq] is dissolved in THF (1150) and NaI (720 g) is added, the reaction is at room temperature for approximately 4 hr. After reaction completion, excess NaI and NaCl are filtered off and the filtrate is concentrated at 40° C. The concentrated residue is re-dissolved in ethyl acetate (2300 g) and extracted with water (2900 g), the organic layer is washed with 10% aqueous solution of $Na_2S_2O_3$ (2600 g) followed by 5% brine solution (2900 g). The organic layer is concentrated to a residue. The residue is re-dissolved in ethyl acetate (4200 g), and then filtered. The filtrate is concentrated and taken up in ethyl acetate (765 g) and stirred at room temperature for about 2 hr before slowly adding heptane (380 g). The solids are filtered and dried at 50° C. under vacuum to obtain tert-butyl ((6-(iodomethyl)pyridin-2-yl)methyl)carbamate; 440 g; purity 100%, Yield 85%.

Preparation of tert-butyl (S)-((6-(((tetrahydrofuran-3-yl)oxy)methyl)pyridin-2-yl)methyl)carbamate A solution of t-BuOK (113 g in THF (1.1 kg) is pre-cooled to 5-10° C., before charging a solution of (S)-tetrahydrofuran-3-ol (166 g) in THF (220 g). The mixture is stirred at room temperature for about 1 hr. A solution of tert-butyl ((6-(iodomethyl)pyridin-2-yl)methyl)carbamate (440 g, 1 eq) in THF (880 g) is pre-cooled to 10-15° C. before. The tetrahydrofuranyl solution is slowly charged into reaction solution while maintaining an internal temperature below 15° C. After about 1 hour another solution of pre-cooled solution of t-BuOK (50 g) and (S)-tetrahydrofuran-3-ol (66 g) in THF (405 g) kg) is slowly added into reaction mixture while maintaining internal temperature below 10° C. The mixture is stirred at about 10° C. for approximately 1 hour. After reaction completion, the mixture is quenched with water (2200 g) and extracted with toluene (4400 g). The organic layer is washed with 5% brine (2×2200 g). The organic layer is concentrated to dryness at 50° C. under vacuum to obtain tert-butyl (S)-((6-(((tetrahydrofuran-3-yl)oxy)methyl)pyridin-2-yl)methyl)carbamate; 389 g, purity 89.63%, yield 105%.

Preparation of CP-56 Free Base tert-butyl (S)-((6-(((tetrahydrofuran-3-yl)oxy)methyl)pyridin-2-yl)methyl)carbamate (389 g, 1 eq) is dissolved in CH$_2$Cl$_2$ (1556 g) and pre-cooled to 0-5° C. before charging drop-wise methanesulfonic acid (MSA; 600 g) into the reaction solution while maintaining internal temperature below 20° C. The mixture is warmed to room temperature and hold for about 1 hr. After reaction completion, water (389 g) is added and cooled to 5-10° C. 30% NaOH is charged to adjust the reactor pH to approximately 12.5. The mixture is stirred for about 30 min before extracting with CH$_2$Cl$_2$ (1556 g). The organic layer is collected and extracted with an aqueous saturated solution of brine (584 g). The organic layer is concentrated under vacuum. The residue is re-dissolved in toluene (1560 g and then concentrated. The concentrated residue is re-dissolved in toluene (1560 g) and then filtered. The filtrate is concentrated to dryness at 50° C. under vacuum to obtain CP-56 free base; 221 g (after assay correction), purity 91%, yield 84.23%.

Preparation of CP-56

CP-56 free base (221 g (after assay correction), 1 eq) is dissolved in MeOH (260 g) and EtOH (1300 g) and then cooled about 15° C. Oxalic acid (47), pre-dissolved in MeOH (110 g is charged into reaction mixture. The reaction is at 15-20° C. for 3 hr. The mixture is cooled to 0-5° C. and stirred for about an 1 hr. The solid is collected by filtration and the wet-cake is washed with EtOH (390 g). The solid is dried under vacuum at 50° C. to obtain CP-56 crude. Crude CP-56 is recrystallized from isopropanol (865 g) and H$_2$O (100 g). The mixture is heated to about 70° C. to obtain a solution. The solution is slowly cooled to 50° C. for 1 hr. The mixture is cooled to 0-5° C. for about another 1 hr. The solid is filtered and washed with isopropanol. The wet-cake is dried at 50° C. under vacuum to obtain CP-56; 164 g, purity 99%, yield 95%.

Alternatively, CP-56 can be formed using the following process:

Reaction Scheme 2

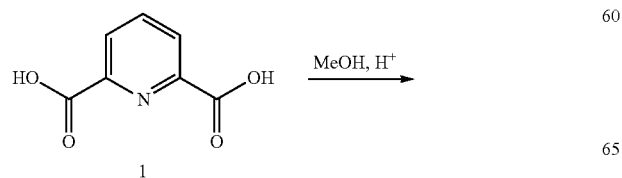

1

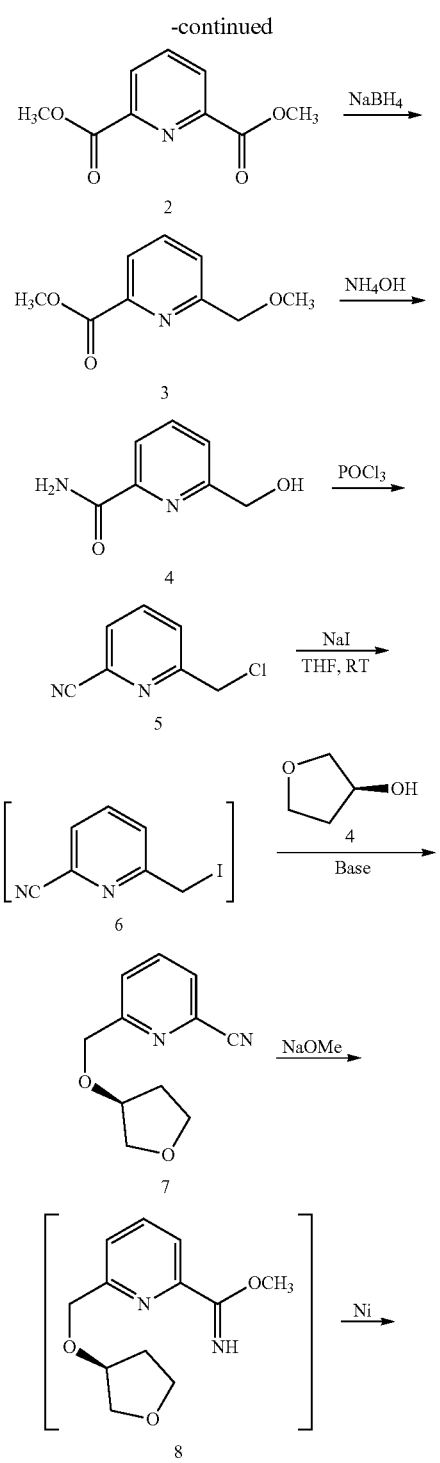

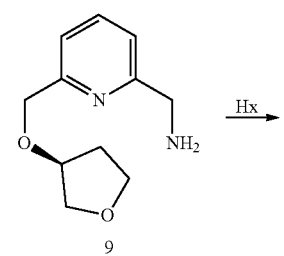

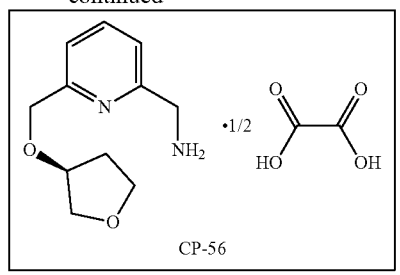

CP-56

Preparation of Dimethyl pyridine-2,6-dicarboxylate (Compound 2)

Charge diacid (1; 628 g) into reactor containing methanol (2 Kg) and heat to reflux. After reaction completion the reaction is cooled to 30 C and stirred. The wet-cake is filtered and washed with methanol (500 g). The wet-cake is dried under vacuum at about 55° C. to obtain diester (680 g, purity >99%; yield 85%).

Preparation of 6-(hydroxymethyl)picolinamide (Compound 4)

Charge diester (2; 600 g) into reactor containing methanol (1.8 kg) and tetrahydrofuran (1.2 kg). Charge slowly sodium borohydride (NaBH4; about 130 g) into the reaction solution while maintaining an internal temperature below 30° C. After reaction completion aqueous hydrochloric acid (about 350 g of 32% HCl) is charged into the reaction solution. The mixture is concentrated and then charged with dichloromethane (1.8 kg). The organic solution is extracted with water (600 g) and then concentrated to obtain the crude product (3). Crude 3 was dissolved in methanol (1.3 kg) and then charge ammonium hydroxide (20%; 1.3 kg). The solution was stirred until reaction completion before concentrating solution. The residue was taken up in water (600 g) and heated to about 60° C. before cooling to 0° C. The wet-cake was filtered, washed with water and dried in vacuum oven to obtain 6-(hydroxymethyl)picolinamide (about 220 g, >99% purity).

Preparation of 6-(chloromethyl)picolinonitrile (Compound 5)

Charge 6-(hydroxymethyl)picolinamide (about 220 g) into a rector containing acetonitrile (450 g). Charge POCl$_3$ (519 g and agitate at about 70° C. After reaction completion the solution is cooled to about 30° C. before slowly charging into a pre-cool (about 10° C.) reactor with water (305 g). Charge toluene (1.4 kg) to extract the solution mixture. The toluene phase is washed in sequence with 20% NaOH (600 g), saturated NaHCO$_3$ (300 g) and water (300 g). Toluene is concentrated to obtain crude Cl-nitrile, 5. Isopropyl alcohol (400 g) is charged to dissolve the wet-cake at about 45° C. before cooling to about 0° C. The wet-cake was filtrated and washed with heptane (150 g) and dried in vacuum oven to obtain 6-(chloromethyl)picolinonitrile (180 g; >99%.

Preparation of (S)-6-(((tetrahydrofuran-3-yl)oxy)methyl)picolinonitrile (Compound 7)

Charge Cl-nitrile (180 g) into a rector containing THF (540 g). Charge NaI (185.7 g) to the reactor and stirred at 50° C. After reaction completion, the reactor is cooled to 0° C. In another reactor, charge t-BuOK (145.6 g) and THF (320 g). Add (S)-tetrahydrofuran-3-ol (311.9 g) into the reactor while maintaining internal temperature below 50° C. to deprotonate the alcohol. Stir until t-BuOK dissolves. Add THF-OK/THF solution into 6-(iodomethyl)picolinonitrile solution (compound 6) while maintaining internal temperature below 10° C. Stir at room temperature until reaction completion. Concentrate the solution to remove THF solvent. Add ethyl acetate (630 g) and wash by water (420 g). Extract water phase by ethyl acetate (630 g). Combine organic layer and concentrate to obtain oil crude 374 g. The residue was distilled under vacuum (P=3~4 torr, internal temperature 174° C. to 188° C.) to obtain (S)-6-(((tetrahydrofuran-3-yl)oxy)methyl)picolinonitrile (compound 7) as an oily product (204 g, >96% purity; 74% yield).

Preparation of (S)-(6-(((tetrahydrofuran-3-yl)oxy)methyl)pyridin-2-yl)methanamine (Compound 9)

Charge (S)-6-(((tetrahydrofuran-3-yl)oxy)methyl)picolinonitrile (180 g) into a rector containing MeOH (1620 g). Charge NaOMe (95.3 g) to the reactor and stirred for 30 min at 30° C. until reaction completion. The methyl (S)-6-(((tetrahydrofuran-3-yl)oxy)methyl)picolinimidate solution (compound 8) was transferred to hydrogenation apparatus containing 50% Ni (60 g). Purge with N$_2$ and then increase the H$_2$ pressure. Under H$_2$ pressure of 5 kg/cm$^2$ and temperature of 30° C. until reaction completion. The reaction is filtered through celite. The filtrate is concentrated. Toluene is charged (1 kg) and then concentrated. Then add toluene (1000 g) and filter to remove salt by-products. The filtrate was concentrated to obtain the oil residue of (S)-(6-(((tetrahydrofuran-3-yl)oxy)methyl)pyridin-2-yl)methanamine (136 g; 85% yield, assay 80%, >91% purity).

Preparation of CP-56

Charge (S)-(6-(((tetrahydrofuran-3-yl)oxy)methyl)pyridin-2-yl)methanamine (170 g) into a rector containing isopropyl alcohol (600 g). Set internal temperature of 75° C. In another reactor, charge oxalic acid (41.1 g) and water (60 g) and heat solution. Add oxalic acid solution into CP-56 free-base solution. Cool to 30° C. for about 4 hours and agitate. The wet-cake was filtered and washed with isopropyl alcohol (175 g) and dried under vacuum drying with heat to obtain crude CP-56 (136.2 g). Charge CP-56 crude (123 g) into a rector containing methanol (1295 g). Stir until CP-56 was dissolved completely. Filter through celite to remove insoluble salt. The filtrate is concentrated. Charge isopropyl alcohol (500 g) and water (50 g) to dissolve CP-56 using heat. Cool to about 30° C. for about 3 hours and stir. The wet-cake was filtrated and washed by isopropyl alcohol (165 g) and dried under vacuum drying with heat to obtain CP-56 (113.4 g. purity=>99%, >99% ee).

Example 2. Preparation of CP-57

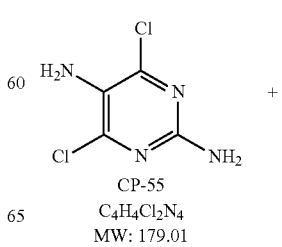

CP-55
$C_4H_4Cl_2N_4$
MW: 179.01

+

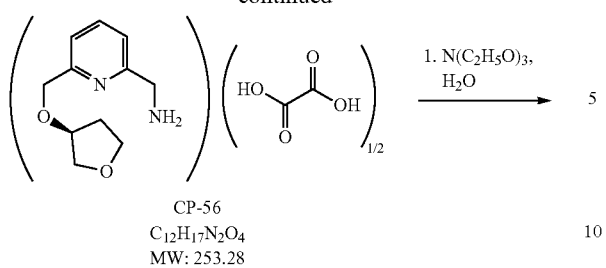

CP-56
C₁₂H₁₇N₂O₄
MW: 253.28

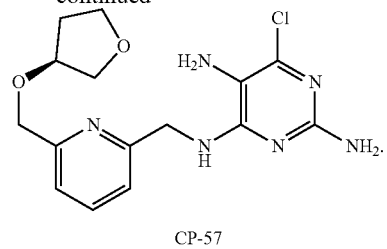

CP-57

It should be noted that base could be amine base such as DIPEA or TEA inorganic bases such as NaHCO₃ or Na₂CO₃.

To the reactor were added CP-56(10 g, 39.51 mmol), CP-55 (7.43 g, 41.48 mmol), isopropanol (35 mL), and N,N-Diisopropylethylamine (17.2 mL, 98.77 mmol; 13.38 g). The suspension was stirred and heat to reflux overnight. After reaction completion, the reaction was quenched with water (100 mL, 10 vol). The temperature of the solution was reduced to 55° C. and seed crystals were added. The solution was the cooled over 22 h to 2.5° C. and held. The suspension was filtered. The filter cake were washed with water. The wet-cake was dried under vacuum at 40° C., providing 11.93 g of CP-57 (86% yield).

Alternatively, a CP-57 dichloride salt can be formed using N-methylmorpholine, TMSCl and Methanol as follows:

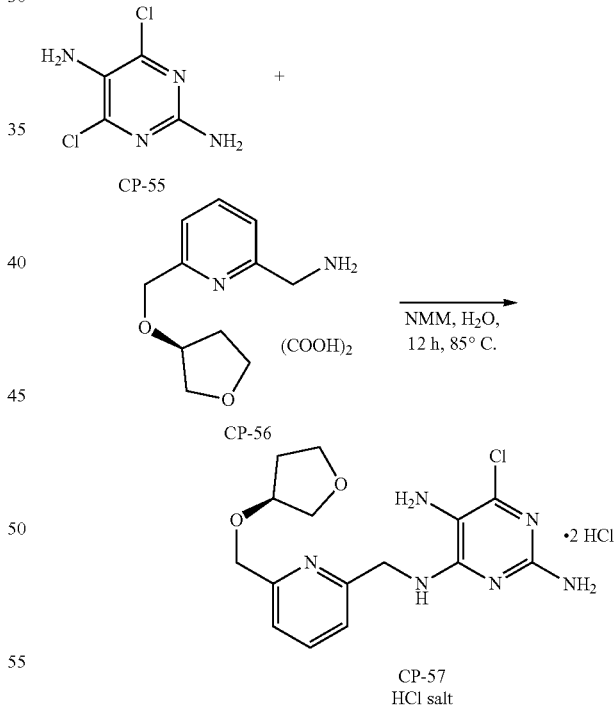

CP-57
C₁₅H₁₉ClN₆O₂
MW: 350.80

A mixture of CP-56 (1 equivalent, 95 g) and CP-55 (approximately 1 equiv, 67 g) in water (approximately 1.5 volume wrt CP-56, 140 mL) and triethanolamine (approximately 1.5 volume wrt CP-56, 140 mL) were heated to a solution at approximately 95° C. The solution was stirred for approximately 6 hours for reaction completion. The solution was cooled to approximately 90° C. before water (approximately 2 volume, 200 mL) was added at such a rate to maintain the temperature above 80° C. The solution was stirred while cooling to approximately 5° C. to precipitate out the product. The product was collected by filtration and then re-slurried in water (approximately 100 mL) and filtered. The product was re-dissolved in hot was propanol (approximately 100 mL) and water was then added (approximately 100 mL). The solid suspension was cooled to approximately 5° C. and stirred for approximately 1 hour. The product was collected by filtration and washed with water (approximately 140 mL) before drying under vacuum at approximately 40° C. to obtain CP-57. Purity 99% and conform to reference.

Alternatively, CP-57 can be prepared by the following process:

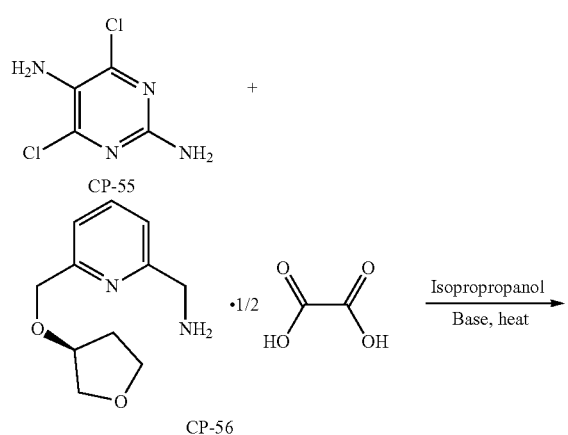

The mixture of CP-55 (10 g), CP-56 (17.5 g), NMM (40 mL) and H₂O (40 mL) was stirred at 85° C. After approximately 12 hrs, the solution was cooled to room temperature. A slurry was formed during the cooling to generate a wet cake. The wet-cake was dried in a vacuum oven to give 12.3 g of CP-57 as a free-base. The solid was redissolved in MeOH (20 mL) and then slowly added TMSCl (8.3 g); the solution was stirred at room temperature for about 30 minutes before concentrating to a residue. 2-propanol (18 mL) was added to the residue to become a slurry. Ethyl acetate (18 mL) was then added. The slurry was stirred, filtered and dried by vacuum oven to give 12.66 of CP-57 dihydrochloride salt (43%; 97% purity). The product conformed to reference.

Example 3. Preparation of CP-58

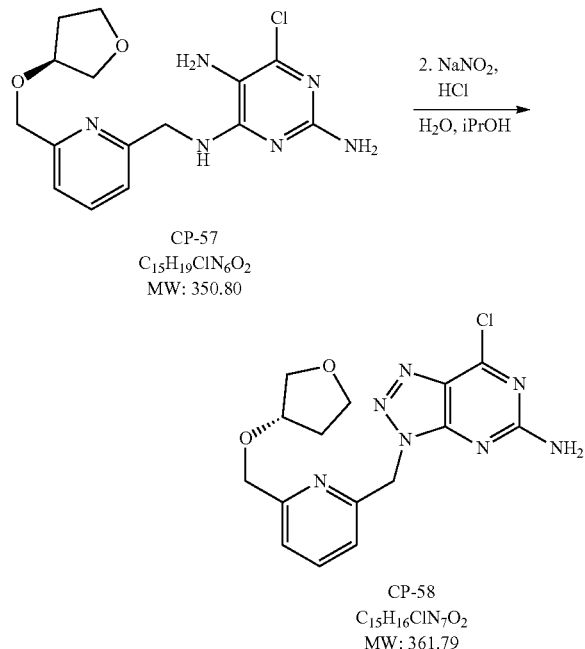

CP-57
C₁₅H₁₉ClN₆O₂
MW: 350.80

CP-58
C₁₅H₁₆ClN₇O₂
MW: 361.79

CP-57 (50.0 g, 1 equiv.) in water (approximately 280 ml) and IPA (approximately 250 ml) was added 37% aqueous HCl (approximately 22 g) and stirred for approximately 30 minutes to dissolve the CP-57 solid. The solution was cooled to approximately 5° C. A solution of sodium nitrite (approximately 12 g) in water (125 ml) was slowly added and stirred at approximately 5° C. until reaction completion. A solution of 28% ammonium hydroxide (approximately 6 g) in water (approximately 135 mL) was added. The resulting slurry was stirred for approximately 20 minutes and then filtered. The cake was washed with water (approximately 400 mL) followed by with 2-propanol (approximately 50 mL). The cake was dried overnight in a vacuum oven. The dried solid was then charged with THF (approximately 250 mL) and the slurry was heated to approximately 60° C. to obtain a solution before adding 2-propanol (approximately 250 mL). The solution was cooled to 5° C. The slurry was filtered and the cake was washed with 2-propanol (approximately 250 mL). The wet cake was dried overnight in a vacuum oven to obtain CP-58 as an off-white solid (48.84 g, 95% yield); HPLC purity=99.6 area %. CP-58 conform to reference.

Alternatively, CP-57 can be made into a CP-57 HCl salt which can then be converted step-wise into CP-58, as follows:

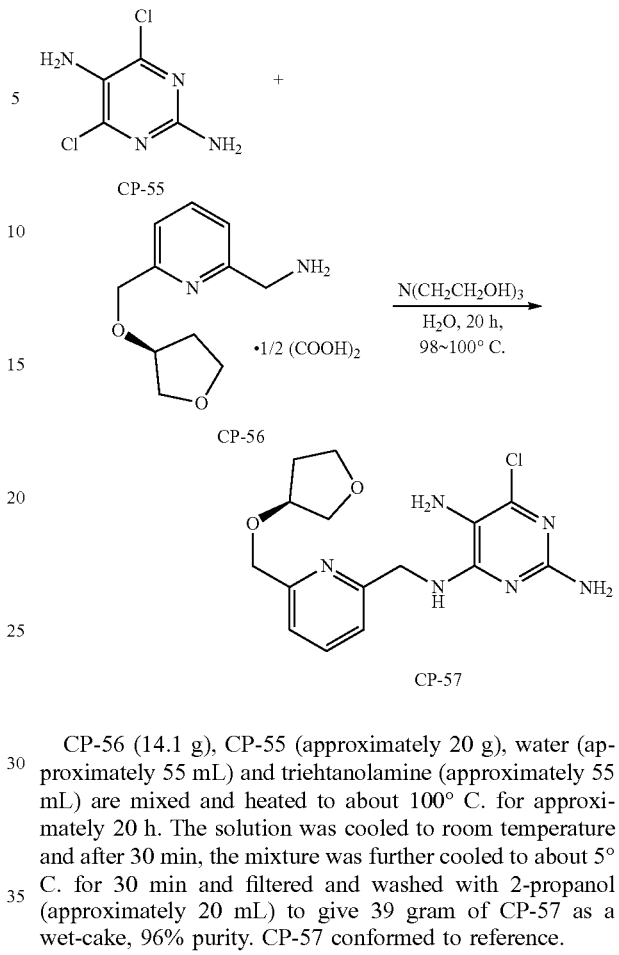

CP-56 (14.1 g), CP-55 (approximately 20 g), water (approximately 55 mL) and triehtanolamine (approximately 55 mL) are mixed and heated to about 100° C. for approximately 20 h. The solution was cooled to room temperature and after 30 min, the mixture was further cooled to about 5° C. for 30 min and filtered and washed with 2-propanol (approximately 20 mL) to give 39 gram of CP-57 as a wet-cake, 96% purity. CP-57 conformed to reference.

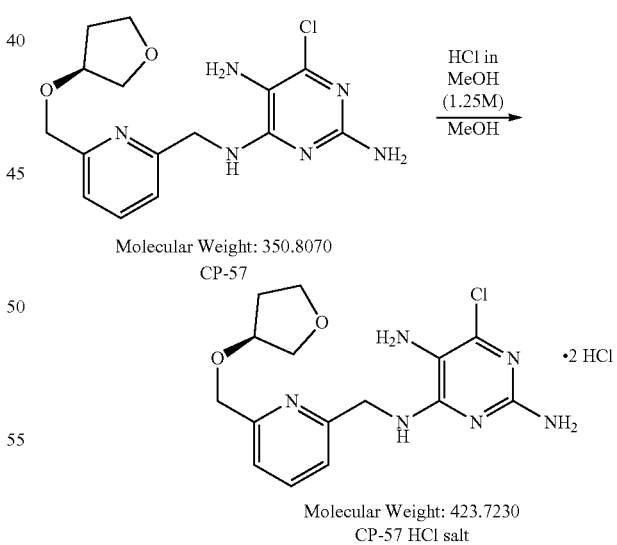

Molecular Weight: 350.8070
CP-57

Molecular Weight: 423.7230
CP-57 HCl salt

To CP-57 wet-cake (39 g) was added methanol (approximately 22 mL) to form a solution and to the solution was slowly added a solution of hydrogen chloride in methanol (1.25 M; approximately 133 mL). The solvent of the reaction was removed by evaporation and to the residue was added 2-propanol (approximately 90 mL) and MeOH (approximately 30 mL) at room temperature. The solution was added some seed crystal of CP-57 HCl (optional) to crystallize out CP-57 HCl salt. The mixture was cooled to 5° C. and stirred for another 30 minutes before filtering. The solid was dried in vacuum oven at 50° C. to give 17.4 g of CP-57 HCl salt (99.6% purity). The filtrate was concentrated and crystallized with 2-propanol to give additional 3 g of CP-57 HCl salt (99% purity). Total yield: 44%. It is to be noted that additional acid is not required as the diazotization reaction is promoted by the CP-57 dihydrochloride salt.

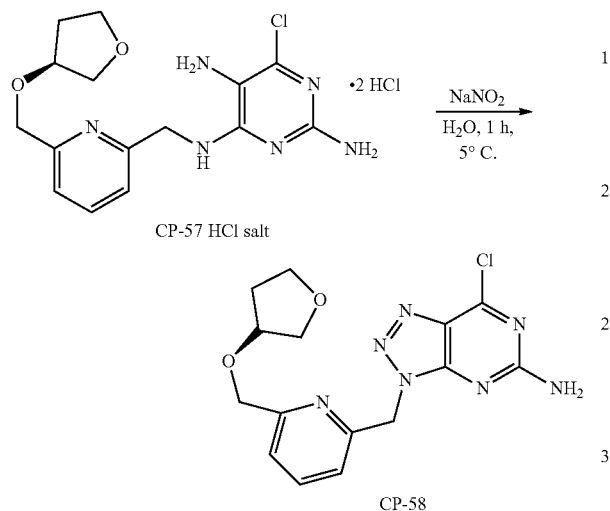

CP-57 HCl salt

CP-58

CP-57 HCl salt was dissolved in 82 mL water (approximately 80 mL) and cooled to about 5° C. The solution of sodium nitrite ($NaNO_2$; 3.5 g in $H_2O$ 10 mL) was added to the reaction in 15 mins. When the reaction was complete a solution of 12.5% $NH_4OH$ (about 5.8 g) was added to the reaction mixture at 5° C. (pH=9~10). The solid was filtered to obtain a wet-cake and dried in vacuum oven; 96% purity. The solid was recrystallized by adding THF (approximately 190 mL) and heated to 65° C. cooled to 45° C. before slowly adding hexane (approximately 190 mL). The slurry was cooled to 5° C. for 30 min and then filtered. The wet cake (17 g) dried in a vacuum oven to obtain CP-58 (14.4 g, 82% yield; 98% purity).

Example 4. Preparation of CPI-444

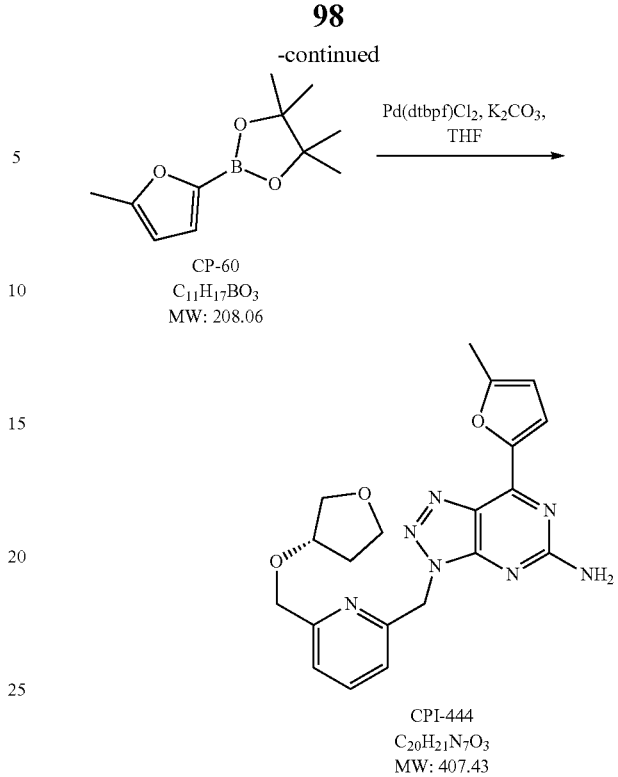

CP-60
$C_{11}H_{17}BO_3$
MW: 208.06

CPI-444
$C_{20}H_{21}N_7O_3$
MW: 407.43

It is to be noted that other Pd coupling reagents can also be used such as $Pd(PPh_3)_4$ or $Pd(PPh_3)_2Cl_2$.

A solution of CP-58 (30.0 g, 1 equiv.), CP-60 (approximately 20.8 g, 1.2 equiv.), in THF (approximately 180 mL), $K_2CO_3$ (approximately 17.5 g), Pd(dtbpf)$Cl_2$ (approximately 337 mg), and water (approximately 100 mL) were stirred and heated to about 60° C. until reaction completion. The reaction was cooled to about 50° C. and the layers were allowed to separate. The aqueous layer was removed and back extracted with THF (approximately 30 mL). The THF layers were combined and water (approximately 450 ml) was added to precipitate out crude CPI-444. The slurry was cooled to about 20° C. and stirred for approximately 60 min and the slurry was filtered. The cake was washed in sequence with water (approximately 120 ml) and 2-propanol (approximately 30 ml). The wet-cake was dried in the vacuum oven to provide an off-white solid (29.74 g, 88% yield) with a purity of 98.5%. Crude CPI-444 conforms to reference.

Alternatively, CPI-444 can be prepared by the following process:

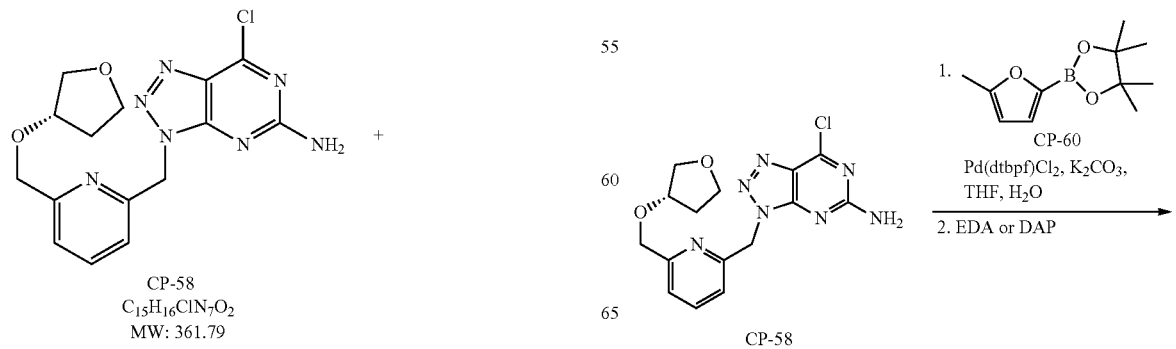

CP-58
$C_{15}H_{16}ClN_7O_2$
MW: 361.79

CP-60

CP-58

-continued

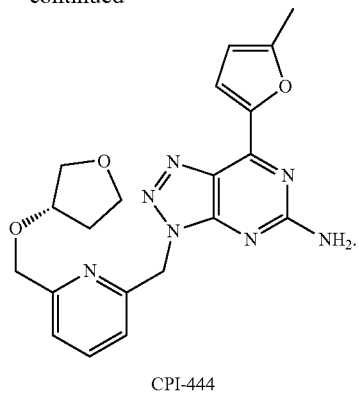

CPI-444

EDA and DAP are used to remove Palladium during CPI-444 formation.

The solution of CP-58 (10 g), CP-60 (6.9 g), Pd(dtbpf)Cl$_2$ (approx. 0.0015 mol eq) and K$_2$CO$_3$ (5.8 g) in THF (6V) and H$_2$O (3V) is heated to approximately 60° C. The reaction is complete after approximately 30 minutes. The solution is cooled to 50° C. and aqueous layer is separated. The aqueous layer is extracted with THF (9 mL); the THF layer is added to organic solution. The organics are cooled to 40° C., 1,3-diaminopropane (DAP; approximately 50 g) or ethylene diamine (EDA; approximately 45 g) is added and the mixture stirred for 1 hour. H$_2$O (15V) is added to the organic layer over 10 min. The slurry is cooled to 20° C. for 2 hours, and stirred for an additional 1 hour. The slurry is filtered and washed with H$_2$O (2V×2) and iPrOH (1V). CPI-444 wet-cake is dried at 50° C. under full vacuum. (Yield=90%; purity >99.0%).

Alternatively, CPI-444 can be prepared by the following process:

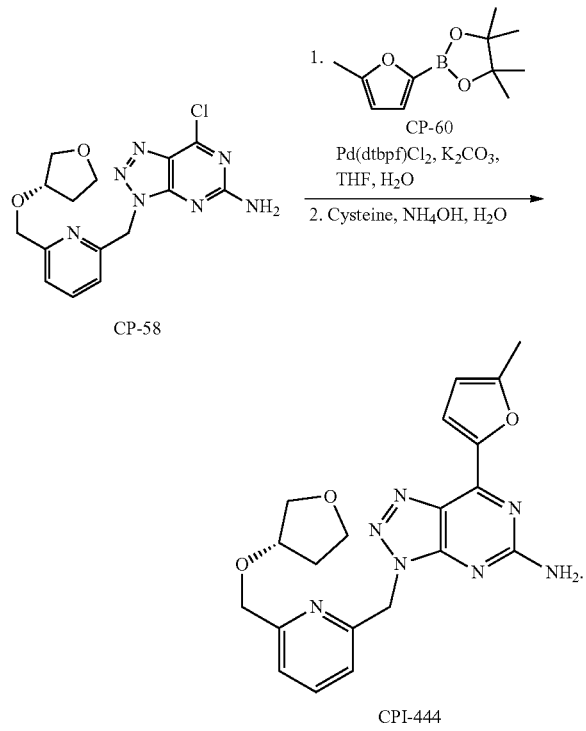

using cysteine in TNF to remove Palladium during CPI-444 formation

CP-58 (1 kg), K$_2$CO$_3$ (0.58 kg), water (3 kg), CP-60 (0.69 kg), and THF (5.3 kg), Pd(dtbpf)Cl$_2$ (3 g). The solution is heated to 60° C. The reaction is complete after approximately 30 minutes. Charge THF (4.5 kg) and cool to 50° C. The aqueous layer is separated. The organic layer is charged with cysteine (0.32 kg) and water (5 kg). The mixture is agitated. NH$_4$OH (1.1 kg) is charged to the reaction mixture and agitate for approximately 15 minutes. The layers are allowed to separate and the lower aqueous layer is separated. The organic layer is charged with cysteine (0.32 kg) and water (5 kg). The mixture is agitated. NH$_4$OH (1.1 kg) is charged to the reaction mixture and agitate for approximately 15 minutes. The layers are allowed to separate and the lower aqueous layer is separated. THF is distilled to approximately 7 volumes under atmospheric pressure. The solution is cooled to 50° C. before charging NH$_4$OH (0.5 kg) and agitate for 30 min. Water (14.5 kg) is charged while maintaining the internal temperature >40° C. The reactor is cooled to 20° C. for 2 hours and hold for an additional 1 hour. CPI-444 is filtered and washed with water followed by isopropanol. CPI-444 wet-cake is dried under vacuum at 50° C. Purity >99%, yield 85%.

Example 5. Removal of Residual Palladium with Biocap Filter Cartridge

A mixture of CPI-444 crude (16.00 g), THF (approximately 190 ml), L-cysteine (approximately 8 g), and H2O (approximately 90 ml) were mixed and heated to a solution at about 60° C. for 1 hour. A solution of 28% NH$_4$OH (approximately 20 ml) was added and heated for an additional 15 minutes. The agitation was turned off to allow the layers allowed to settle. The aqueous layer was removed; the THF layer was washed with brine solution (approximately 15 ml). The combined aqueous solutions were back extracted with THF (approximately 15 ml). A 3M Biocap filter (BC0025LR55SP; available from 3M) was pretreated with THF (approximately 150 ml) at about 50° C. The combined organic layers were recirculated through the Biocap at about 10 ml/min for approximately 3 hours and then filtered forward. The Biocap filter was rinsed with THF (approximately 130 ml) at about 50° C. The combined filtrates were concentrated. Water (approximately 80 ml) was added, and distilled to remove residual THF. 2-Propanol (approximately 110 ml) was added to the slurry, and the mixture was heated to a solution. The solution was cooled to 20° C. and water (approximately 240 ml) was added. The slurry was performed in series by heating to about 55° C. and held that that temperature for approximately 30 minutes, cooled to 20° C. over 30 minutes, and held at 20° C. for 30 minutes. This heating cycle was repeated two more. The slurry was then held at 20° C. for approximately 12 hours. The slurry was filtered, and the product was washed with water (approximately 300 ml). The wet cake (about 23 g) was dried in the vacuum oven to obtain an off white solid (13.6 g; 85% yield; 99.9% purity; Pd=25 ppm).

Reprocess of Step 4. AFC-825-106

CPI-444 (16.02 g, AFC-825-48) and THF (approximately 280 ml) were charged to a flask and heated to about 50° C. for about 30 minutes to obtain a solution. A 3M Biocap filter (BC0025LR55SP) was pretreated with THF (approximately 150 ml) at about 50° C. The CPI-444 solution was passed through the Biocap at about 10 ml/min. The Biocap filter was rinsed with THF (approximately 130 ml) at about 50° C. The combined filtrates were transferred to a reactor and concentrated. Water (approximately 80 ml) was added, and distilled to remove residual THF solvent. 2-Propanol (approximately 110 ml) was added to the slurry and heated to about 65° C. to obtain a solution. The solution was cooled to about 20° C. before adding water (approximately 240 ml). The slurry was heated to 55° C. over 30 minutes, held at 55° C. for 30 minutes, cooled to 20° C. over 30 minutes, and held at 20° C. for 30 minutes. This heating cycle was two more times. The slurry was then held at 20° C. for 12 hours. The slurry was filtered, and the product was washed with water (approximately 300 ml). The wet cake (26.6 g) was dried in the vacuum oven overnight to obtain 15 as a white solid (95% yield; 99% purity; Pd=5 ppm).

Example 6. Removal of Residual Palladium with Darco KB-G

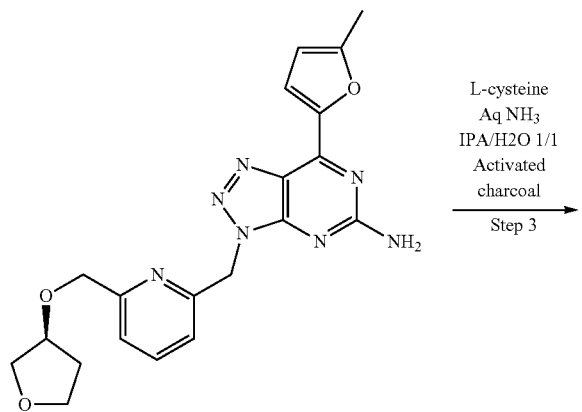

Chemical Formula: $C_{20}H_{21}N_7O_3$
Molecular Weight: 407.43
Crude CPI-444

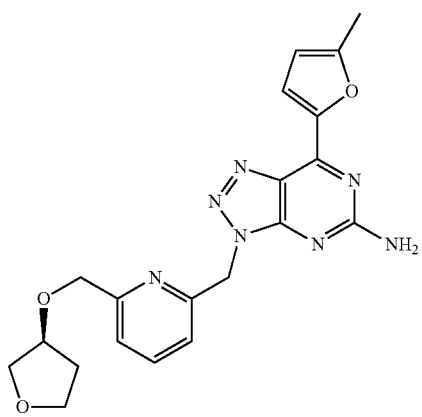

Chemical Formula: $C_{20}H_{21}N_7O_3$
Molecular Weight: 407.43
CPI-444 Drug Substance Crude CPI-444 (475 g, 1.17 mol, 1.00 eq), 2-MeTHF (11.9 L, 25.0 vol) and WFI water (2.6 L, 5.5 vol) were charged to a 19 L jacketed reactor. The mixture was mechanically agitated under a nitrogen blanket. Nitrogen was bubbled through the solution for 20 minutes. L-Cysteine (242 g, 1.99 mol, 1.71 eq) was then charged. The solution in the reactor was heated to 55±5° C. Upon reaching 50° C., the reaction mixture was stirred for 1 hour. 28-30% NH$_4$OH (594 mL, 1.25 vol) was charged via addition funnel, and then the reaction mixture was stirred for 15 min. Agitation was stopped and the reaction was allowed to separate for 1 hour. The aqueous layer was removed. The organic layer was allowed to cool to ambient. The organic layer was filtered and the frit was washed with 2-MeTHF (618 mL, 1.3 vol). The organics were concentrated off by rotary evaporation. WFI water (2.42 L, 5.1 vol) and IPA (2.38 L, 5.0 vol) were used to charge the concentrated slurry to a clean 19 L jacketed reactor under N$_2$. The mixture was heated to 65±5° C., and then was stirred for 1 hour to obtain solution. Darco KB-G activated carbon (71.3 g, 15 wt %) was charged. The reactor was heated to 75±5° C. and stirred for 15 hours. A 1 L pocket filter was prepared with filter cloth and a heating jacket and heated to 70±5° C. Reactor contents were filtered through the pocket filter using N$_2$ pressure. The pocket filter was rinsed with a mixture of IPA/WFI water (1:1, 950 mL, 2 vol) followed by a mixture of IPA/WFI water (1:1, 1.90 L, 4 vol) and IPA/WFI water (1:1, 1.90 L, 4 vol). Inside a 22 L three neck round bottom flask the filtrates were mechanically agitated under a N$_2$ blanket. WFI water (7.13 L, 15 vol) was slowly added via addition funnel over 1 h at ambient temperature, and aged for 1 h. The slurry was heated to 55±5° C. and maintained the temperature for 30 min. This heating and subsequent cooling were repeated twice more. After reaching ambient temperature the final time, the mixture was stirred for at least 2 hours. The reaction mixture was filtered and the reactor rinsed with WFI water (2.38 L, 5.0 vol, 3×). The cake was dried under N$_2$ for 30 minutes and then transferred to a glass dish. The material was dried under full vacuum at 55±5° C. The desired product was obtained 368.1 g (77%) as light yellow solids. This material was 99.6% pure by HPLC and had a Pd content of 3.6 ppm.

Example 7. Removal of Residual Palladium with Polymer-Bound Thiol (SiST)

Crude CPI-444 (24.48 g, pd=1267 ppm) and THF (244.8 mL, 10 vol) were charged to a 500 mL 4-necked flask fitted with mechanical agitation, a condenser with nitrogen balloon and a thermometer. The slurry was heated to 60° C. for 20 minutes and then slowly cooled to 45° C. SiST (36.72 g) was added to the solution and the mixture was stirred at 42° C. for 14 h. The mixture was filtered and washed by THF (24 mL, 1 vol, twice; Pd=13.12 ppm). H$_2$O (120 mL, 5 vol) and IPA (120 mL, 5 vol) were charged to the flask. The slurry was heated to 70° C. and maintained for 1 h (the slurry became solution). The solution was slowly cooled to room temperature and the slurry was added H$_2$O (360 mL, 15 vol) and heated to 55° C. for 1 h. The slurry was cooled to room temperature and then heated to 55° C. for 1 h. The slurry was cooled to rt. and stirred at rt. for 2 h. The slurry was filtered and washed by H$_2$O (100 mL, 4 vol, three times). The wet cake (28.36 g) was dried by 10 mmHg and 50° C. for overnight (14 h) and the weight of CPI-444 was 19.31 g (79% recovery).

Example 8. Removal of Residual Palladium by Recrystallization

CUNO Filter Cartridge 55 S

CPI-444 (5.0 g, Pd 14.06 ppm) and THF (50 mL, 10 vol) were charged to a 100 mL 3-necked flask fitted with stirring bar, a condenser with nitrogen balloon and a thermometer. The slurry was heated to 60° C. for 20 minutes and added CUNO 55S filter (0.75 g, 15 w %). The mixture was stirred at 60° C. for 1 h. The mixture was filtered and washed by THF (5 mL, 1 vol, twice). The filtrate was concentrated. The solid, H$_2$O (25 mL, 5 vol) and IPA (25 mL, 5 vol) were charged to 250 mL 3-necked flask fitted with stirring bar, a condenser with nitrogen balloon and a thermometer. The slurry was heated to 70° C. and maintained for 1 h (the slurry became solution). The solution was slowly cooled to rt. (40 minutes) The slurry was added $H_2O$ (75 mL, 15 vol) and then heated to 55° C. for 1 h. The slurry was cooled to rt. (30 minutes) and stirred at rt. for 2 h. The slurry was filtered and washed by $H_2O$ (20 mL, 4 vol, three times). The cake (6.355 g) was dried by 10 mmHg and 50° C. for overnight (16 h) and the weight of CPI-444 was 4.281 g (85% recovery). Pd content (ppm)=2.02 ppm.

Polymer-Bound Thiol: SiST

CPI-444(5 g; Pd 14.06 ppm) was dissolved in THF (50 mL) at 60° C. The solution was cooled to 55° C. and SiST (7.5 g) was added to the solution. The solution was stirred at 50~55° C. for 16 h. The solution was filtered through celite and a 0.2 micron filter. The filtrate was tested for Pd content. Result: 2.43 ppm.

Example 9. Preparation of CPI-144 with Alternative Palladium Catalyst gested by the present disclosure and the foregoing description thereof, without departing from the substance or scope of the present disclosure. Furthermore, any sequence(s) and/or temporal order of steps of various processes described and claimed herein are those considered to be the best mode contemplated for carrying out the present disclosure. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in various different sequences and orders, while still falling within the scope of the present inventions. In addition, some steps may be carried out simultaneously. Accordingly, while the present disclosure has been described herein in detail in relation to preferred embodiments, it is to be understood that this disclosure is only illustrative and exemplary of the present disclosure and is made merely for purposes of providing a full and enabling disclosure of the disclosure. The foregoing

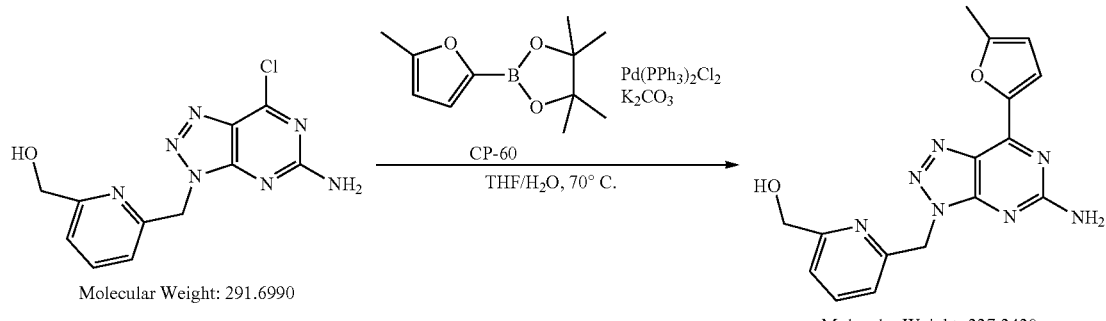

Molecular Weight: 291.6990

Molecular Weight: 337.3430

| | | | |
|---|---|---|---|
| S.M. | 0.5 g | 1.71 | 1 |
| CP-60 | 0.429 g + 0.047 g | 2.06 + 0.23 | 1.2 + 0.14 |
| Pd(PPh$_3$)$_2$Cl$_2$ | 0.0072 g | 0.01026 | 0.006 |
| K$_2$CO$_3$ | 0.359 g | 2.599 | 1.52 |
| THF | 3.9 mL | | 7.9 V |
| H$_2$O | 3.95 mL | | 7.8 V |

1. A solution of S.M., CP-60, Pd(PPh$_3$)$_2$Cl$_2$ and K$_2$CO$_3$ in THF-H$_2$O (7.9 mL, 1:1) was put in oil-bath at 70~75° C.
2. After 2 h, 0.047 g CP-60 was added to the reaction at 70~75° C.
3. After 1 hr, the reaction was cooled to rt. and 10 mL H$_2$O was added to the reaction.
4. The reaction was filtered to provide wet cake (0.812 g).
5. The solid wet cake was dried at 45° C. and 20 mmHg for 2 h to provide weight 0.499 g. (86%).
6. The solid wet cake was stirred in 2 mL DMF for 30 mins (slurry) and then filtered. The solid was dried by 45° C. and 10 mmHg for 12 h to provide weight 0.40 g; 69% yield; 98.1% purity.

In view of the foregoing detailed description of preferred embodiments of the present disclosure, it readily will be understood by those persons skilled in the art that the present disclosure is susceptible to broad utility and application. While various aspects have been described in the context of screen shots, additional aspects, features, and methodologies of the present disclosure will be readily discernable therefrom. Many embodiments and adaptations of the present disclosure other than those herein described, as well as many variations, modifications, and equivalent arrangements and methodologies, will be apparent from or reasonably sugdisclosure is not intended nor is to be construed to limit the present disclosure or otherwise to exclude any such other embodiments, adaptations, variations, modifications and equivalent arrangements, the present disclosure being limited only by the claims appended hereto and the equivalents thereof.

What is claimed is:

1. A method of isolating a precipitate of the formula (I):

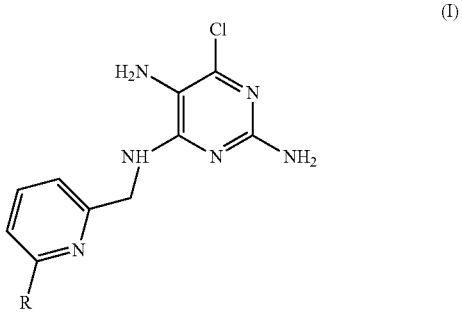

comprising the steps of:
(a) reacting a compound of the formula:

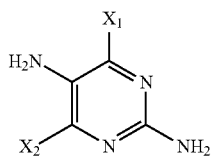

with a compound of the formula:

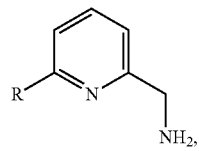

in the presence of a base;
wherein,
$X_1$ and $X_2$ are independently halo, and
wherein R is $-(CR^aR^b)-O-R^2$;
$R^a$ is H or alkyl;
$R^b$ is H or alkyl; or $R^a$ and $R^b$ together with the atom to which they are attached form a 3 to 8 membered saturated or partially saturated hydrocarbon ring or form a 4 to 8 membered saturated or partially saturated heterocyclic ring comprising a ring member selected from O, $N(R^3)$ and S;
$R^2$ is H, alkyl, cycloalkyl or heterocycloalkyl, wherein said alkyl or cycloalkyl may optionally be substituted with halo, alkoxy or heterocycloalkyl;
$R^3$ is H or alkyl;
wherein, heteroaryl is a 5 or 6 membered aromatic ring, comprising one or two ring members selected from N, $N(R^4)$, S and O;
alkyl (or the alkyl group of the alkoxy group) is a linear or branched saturated hydrocarbon containing up to 10 carbon atoms;
heterocycloalkyl is a C-linked or N-linked 3 to 10 membered non-aromatic, monocyclic ring, wherein said heterocycloalkyl ring comprises 1, 2 or 3 ring members independently selected from N, $N(R^4)$, $S(O)_q$ and O;
$R^4$ is H or alkyl; and
q is 0, 1 or 2; and
(b) isolating the precipitate of formula (I).

2. The method of claim 1, wherein X is chloro, fluoro or bromo, iodo or alkylsulfonate.

3. The method of claim 1, wherein the method comprises the step of forming a compound of the formula (II):

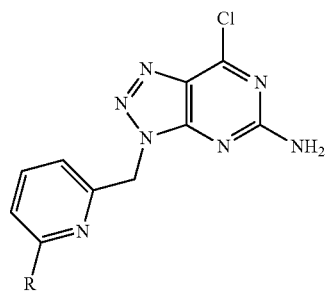

wherein R is as defined above, by:
(a) reacting the precipitate of formula (I) with a nitrite; and
(a) isolating the compound of formula (II).

4. The method of claim 3 wherein said nitrite is isoamyl nitrite or sodium nitrite.

5. The method of claim 1, wherein the precipitate of formula (I) is of the formula:

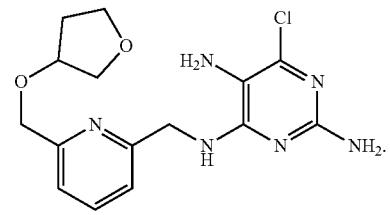 [SMILES: Nc1nc(Cl)c(N)c(NCc2cccc(COC3CCOC3)n2)n1]

6. The method of claim 3, wherein the compound of formula II is of the formula:

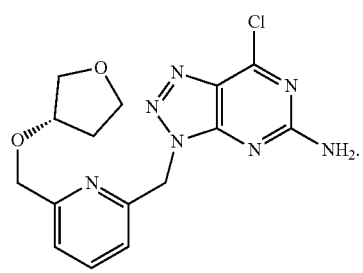 [SMILES: Nc1nc(Cl)c2nnn(Cc3cccc(CO[C@H]4CCOC4)n3)c2n1]

7. The method of claim 3, wherein the method comprises the step of forming a compound of formula (III):

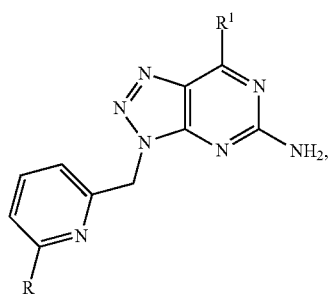

by:
(a) reacting a compound of formula (II) with a compound of the formula $R^1-Y$ in the presence of a palladium catalyst and a base, wherein Y is a leaving group, wherein R is $-(CR^aR^b)-O-R^2$;
$R^a$ is H or alkyl;
$R^b$ is H or alkyl; or $R^a$ and $R^b$ together with the atom to which they are attached form a 3 to 8 membered saturated or partially saturated hydrocarbon ring or form a 4 to 8 membered saturated or partially saturated heterocyclic ring comprising a ring member selected from O, $N(R^3)$ and S;
$R^1$ is phenyl or heteroaryl, wherein said phenyl or said heteroaryl group may be optionally substituted with alkyl, alkoxy, halo or —CN;

R² is H, alkyl, cycloalkyl or heterocycloalkyl, wherein said alkyl or cycloalkyl may optionally be substituted with halo, alkoxy or heterocycloalkyl;
R³ is H or alkyl;
wherein, heteroaryl is a 5 or 6 membered aromatic ring, comprising one or two ring members selected from N, N(R⁴), S and O;
alkyl (or the alkyl group of the alkoxy group) is a linear or branched saturated hydrocarbon containing up to 10 carbon atoms;
alkoxy is a linear or branched saturated hydrocarbon containing up to 10 carbon atoms attached to the remainder of the molecule through an oxygen linker
heterocycloalkyl is a C-linked or N-linked 3 to 10 membered non-aromatic, monocyclic ring, wherein said heterocycloalkyl ring comprises 1, 2 or 3 ring members independently selected from N, N(R⁴), S(O)$_q$ and O;
R⁴ is H or alkyl; and
q is 0, 1 or 2; and
(b) isolating the compound of formula (III).

8. The method of claim 7, further comprising the step of contacting the palladium catalyst with a palladium scavenger.

9. The method of claim 7 wherein said compound is isolated as a precipitate.

10. The method of claim 7, wherein the compound of formula (III) is of the formula:

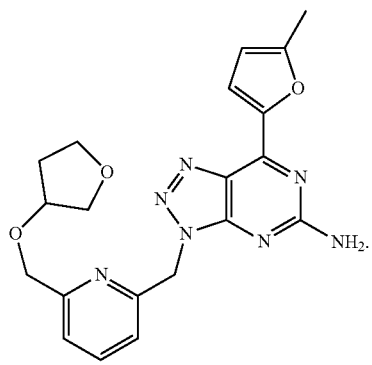 [SMILES: Cc1ccc(-c2nc(N)nc3c2nnn3Cc2cccc(COC3CCOC3)n2)o1]

11. A compound of formula (V):

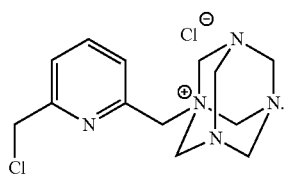

(V)

12. A method of synthesis of the compound of formula (V):

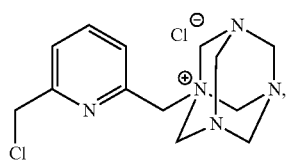 [SMILES: ClCc1cccc(C[N+]23CN4CN(CN(C4)C2)C3)n1 ; [Cl-]]

comprising reacting a compound of formula:

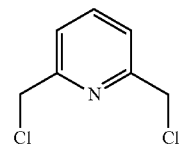

with hexamethylenetetraamine (HMTA) of formula

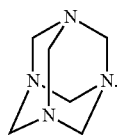

13. A compound of formula (VII):

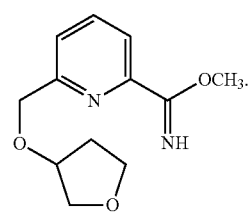

(VII)

14. A method of synthesis of the compound of formula (VII):

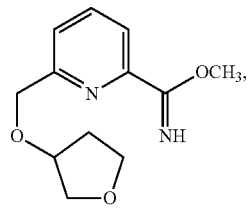 [SMILES: COC(=N)c1cccc(COC2CCOC2)n1]

comprising the step of reacting a compound of formula

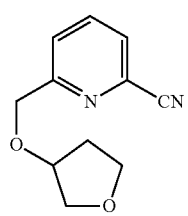 [SMILES: N#Cc1cccc(COC2CCOC2)n1]

with a methoxide, thereby forming a compound of formula

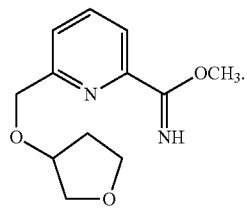 [SMILES: COC(=N)c1cccc(COC2CCOC2)n1]

15. The method of claim 1, wherein said base is N-methylmorpholine or triethanolamine.

16. The method of claim 1, wherein said precipitate is crystalline.

17. The method of claim 1, wherein the precipitate of formula (I) is isolated as a salt and wherein said salt is a hydrochloric acid salt, a di-hydrochloride acid salt, a hydrobromide salt, an alkylsulfonate salt, an acetate salt or a formate salt.

18. The method of claim 1, wherein the precipitate of formula (I) is isolated as a free base.

19. The method of claim 1, wherein the precipitate of formula (I) is isolated by re-crystallization from a polar solvent, wherein the polar solvent is 2 proponol, ethanol and methanol.

20. The method of claim 18, wherein the precipitate of formula (I) is isolated by re-crystallization from methyl alcohol, trimethylsilyl chloride, hydrochloric acid, hydrogen chloride, or dimethylformamide.

21. The method of claim 1, wherein the precipitate of formula (I) is isolated by re-crystallization from hydrogen choride in an alcohol solvent or a non-alcoholic solvent.

22. The method of claim 3, wherein said nitrite is isoamyl nitrite or sodium nitrite.

23. The method of claim 3, wherein the precipitate of formula (I) is reacted with said nitrite at a pH of about 1.0 to about 7.0.

24. The method of claim 3, wherein the compound of formula (II) is isolated as a salt and wherein the salt is hydrochloric acid salt, a di-hydrochloride acid salt, a hydrobromide salt, a di-hydrobromide salt, an alkylsulfonate salt, an acetate salt or a formate salt.

25. The method of claim 3, wherein the compound of formula (II) is isolated as a free base.

26. The method of claim 3, wherein the compound of formula (II) is isolated as a precipitate.

27. The method of claim 3, wherein the compound of formula (II) is isolated as a crystalline.

28. The method of claim 7, wherein Y is an organometallic leaving group selected from a boronate ester moiety and a boronic acid moiety.

29. The method of claim 7, wherein the compound of formula (III) is isolated by re-crystallization from an alcohol solvent, tetrahydrofuran, and water, and wherein said alcohol solvent is isopropanol.

30. The method of claim 7, wherein the base is an inorganic base selected from potassium carbonate, potassium bicarbonate, sodium carbonate, sodium bicarbonate, cesium carbonate, sodium hydroxide, sodium ethoxide and sodium methoxide.

31. The method of claim 7, wherein the palladium catalyst is a palladium complex selected from Pd(dtbpf)Cl$_2$, PdCl$_2$P(Ph$_3$)$_2$, PdP(Ph$_2$)$_4$, Pd(dppf)Cl$_2$, Pd(dippf)Cl$_2$ and Pd$_2$(dba)$_3$.

32. The method of claim 28, wherein the boronate ester moiety is pinacolborane, boronic acid, 2-(5-methylfuran-2-yl) catecholborane, 2-(5-methylfuran-2-yl)-1,3,2-dioxaborinane, diisopropyl (5-methylfuran-2-yl)boronate, (1s,5s)-9-(5-methylfuran-2-yl)-9-borabicyclo[3.3.1]nonane or (5-methylfuran-2-yl)boronic acid.

33. The method of claim 8, wherein said palladium scavenger is a charcoal particle, a polymer-bound charcoal particle, a thiol moiety, a polymer-bound thiol moiety, an amine moiety, or a polymer-bound amine moiety.

34. The method of claim 8 wherein the step of contacting the palladium catalyst with a palladium scavenger results in a reaction mixture comprising the compound of formula (III) having less than about 500 ppm residual palladium, or less than about 400 ppm residual palladium, or less than about 300 ppm residual palladium, or less than about 200 ppm residual palladium, or less than about 100 ppm residual palladium, or less than about 90 ppm residual palladium, or less than about 80 ppm residual palladium, or less than about 70 ppm residual palladium, or less than about 60 ppm residual palladium, or less than about 50 ppm residual palladium, or less than about 40 ppm residual palladium, or less than about 30 ppm residual palladium, or less than about 20 ppm residual palladium, or less than about 10 ppm residual palladium, or less than about 5 ppm residual palladium, or less than about 4 ppm residual palladium, or less than about 3 ppm residual palladium, or less than about 2 ppm residual palladium, or less than about 1 ppm residual palladium.

35. The method of claim 7, wherein the compound is crystalline.

36. The method of claim 12, further comprising forming the compound of formula:

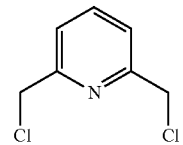

by reacting the compound of formula

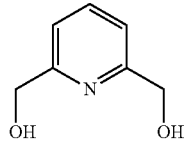

with a chlorinating agent in the presence of organic solvent.

37. The method of claim 36, wherein the chlorinating agent is thionyl chloride and the organic solvent is dichloromethane.

38. The method of claim 36, further comprising forming the compound of formula

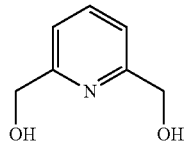

by:

(a) reacting a compound of formula

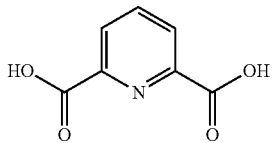

with inorganic acid in the presence of alcohol thereby providing a compound of formula

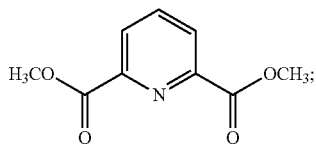 [SMILES: COC(=O)c1cccc(C(=O)OC)n1]

and (b) reacting the compound of formula

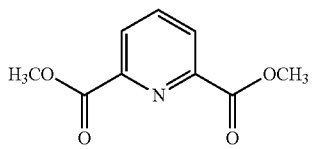 [SMILES: COC(=O)c1cccc(C(=O)OC)n1]

with a reducing agent in the presence of alcohol and a catalyst thereby forming the compound of formula

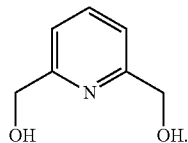

39. The method of claim 38, wherein the inorganic acid is sulfuric acid, the reducing agent is sodium borohydride, the alcohol is isopropanol, ethanol or methanol, and the catalyst is lithium aluminium hydride.

40. The method of claim 38, further comprising the step of forming a compound of formula:

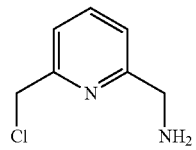

by reacting the compound of formula (V):

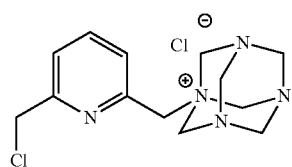 [SMILES: ClCc1cccc(C[N+]23CN4CN(CN(C4)C2)C3)n1 ; Cl]

with alcohol in the presence of inorganic acid thereby forming a compound of formula

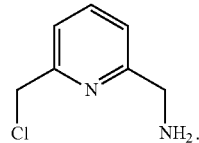

41. The method of claim 40, wherein the inorganic acid is hydrochloric acid and the alcohol is isopropanol, ethanol or methanol.

42. The method of claim 40, further comprising the step of forming a compound of formula:

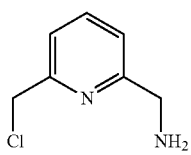

by reacting the compound of formula

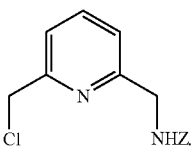

with Boc$_2$O or CbzCl in the presence of organic solvent;
wherein Z is butyloxycarbonyl (Boc) or cabroxybenzyl (Cbz), thereby forming the compound formula

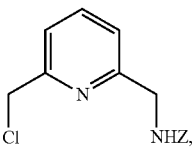

wherein the organic solvent is dichloromethane.

43. The method of claim 42, further comprising the step of forming a compound of formula:

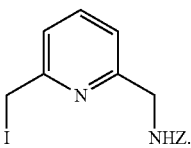

by reacting the compound of formula

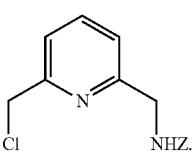

with an ionic compound in the presence of organic solvent;

thereby forming the compound of formula

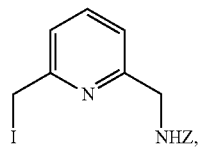

wherein the ionic compound is sodium iodide and the organic solvent is tetrahydrofuran.

44. The method of claim 43, further comprising the step of forming a compound of formula:

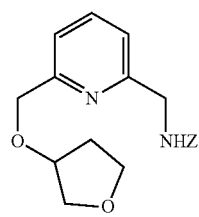 [SMILES: NCc1cccc(COC2CCOC2)n1]

by reacting the compound of formula

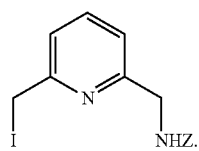

with a compound of formula

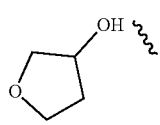

in the presence of an organic solvent and catalyst, thereby forming the compound of formula

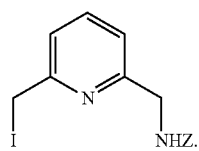

wherein the organic solvent is tetrahydrofuran or toluene and the catalyst is potassium t-butoxide.

45. The method of claim 44, further comprising the step of forming a compound of formula:

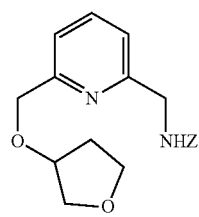 [SMILES: NCc1cccc(COC2CCOC2)n1]

by reacting the compound of formula

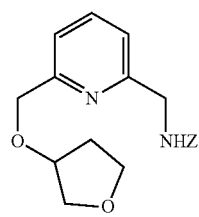 [SMILES: NCc1cccc(COC2CCOC2)n1]

with an organic acid in the presence of organic solvent, thereby forming the compound of formula

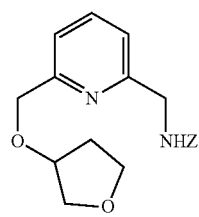 [SMILES: NCc1cccc(COC2CCOC2)n1]

wherein the organic acid is methanesulfonic acid and the organic solvent is dichloromethane.

46. The method of claim 45, further comprising the step of forming a compound of formula (VI):

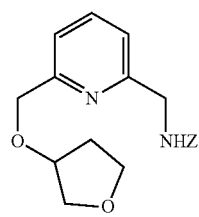 [SMILES: NCc1cccc(COC2CCOC2)n1]

by reacting the compound of formula

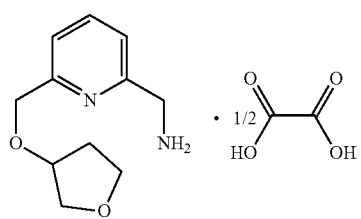 [SMILES: NCc1cccc(COC2CCOC2)n1 ; O=C(O)C(=O)O]

with an oxalic acid in the presence of organic solvent, thereby forming the compound of formula (VI):

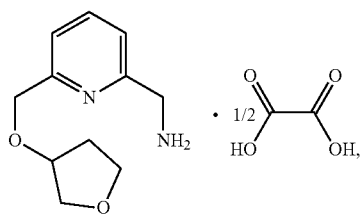 [SMILES: NCc1cccc(COC2CCOC2)n1 ; O=C(O)C(=O)O] 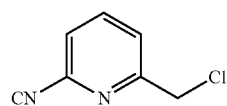

wherein the organic solvent is isopropanol, ethanol or methanol.

47. The method of claim 14, further comprising the step of forming of the compound of formula

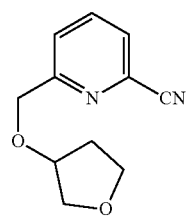 [SMILES: N#Cc1cccc(COC2CCOC2)n1]

by reacting a compound of formula

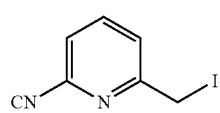

with a compound of formula

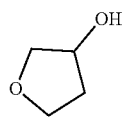

in the presence of a base thereby forming the compound of formula

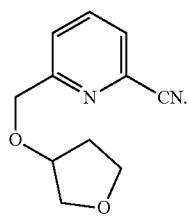 [SMILES: N#Cc1cccc(COC2CCOC2)n1]

48. The method of claim 47, further comprising the step of forming the compound of formula

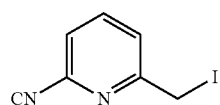

by reacting a compound of formula

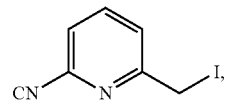

with a iodine salt in the presence of an organic solvent, thereby forming the compound of formula

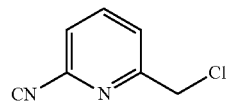

wherein the iodine salt is sodium iodide and wherein the organic solvent is tetrahydrofuran.

49. The method of claim 48, further comprising the step of forming the compound of formula

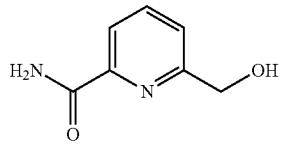 [SMILES: NC(=O)c1cccc(CO)n1]

by reacting a compound of formula

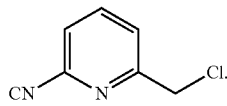

with a chloride salt, thereby forming the compound of formula

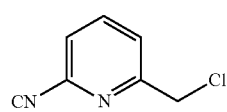

50. The method of claim 49, wherein the forming of the compound of formula

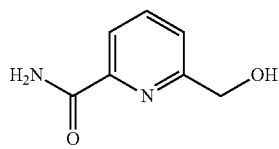

is performed in the presence of phosphoryl chloride.

51. The method of claim 50, further comprising the step of forming the compound of formula by reacting a compound of formula

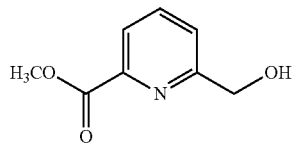 [SMILES: COC(=O)c1cccc(CO)n1]

with an ammonium base, thereby forming the compound of formula

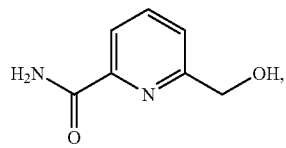 [SMILES: NC(=O)c1cccc(CO)n1]

wherein the ammonium base is ammonium hydroxide.

52. The method of claim 51, further comprising the step of forming the compound of formula

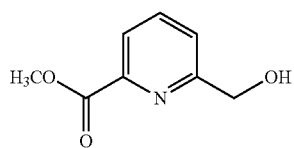

by reacting a compound of formula

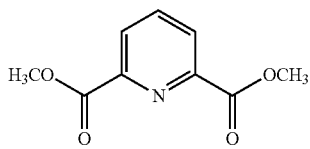 [SMILES: COC(=O)c1cccc(C(=O)OC)n1]

with a reducing agent, thereby forming the compound of formula

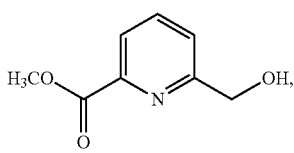

wherein the reducing agent is sodium borohydride.

53. The method of claim 52, further comprising the step of forming the compound of formula:

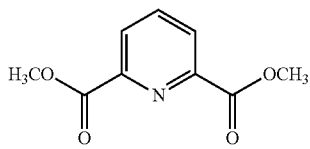 [SMILES: COC(=O)c1cccc(C(=O)OC)n1]

by reacting a compound of formula

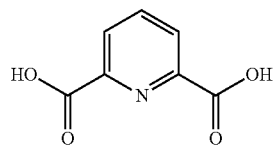 [SMILES: O=C(O)c1cccc(C(=O)O)n1]

with a methylating agent, thereby forming the compound of formula

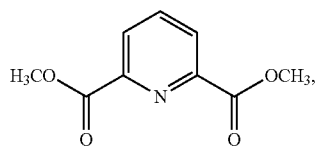 [SMILES: COC(=O)c1cccc(C(=O)OC)n1]

wherein the methylating agent is methanol.

54. The method of claim 53, further comprising the step of forming the compound of formula:

by reacting the compound of formula (VII)

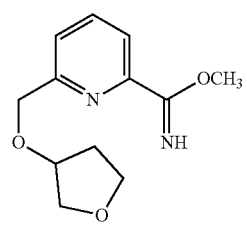 [SMILES: COC(=N)c1cccc(COC2CCOC2)n1]

with a transition metal, wherein the transition metal is iron, cobalt, copper, zinc, or nickel.

55. The method of claim 54, further comprising the step of forming the compound of formula (VI):

by reacting the compound of formula
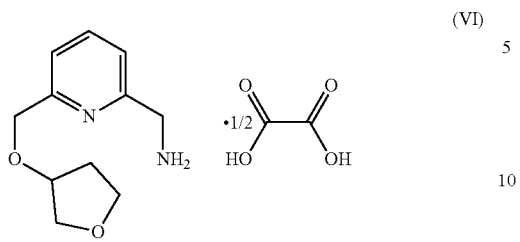
(VI)
with oxalic acid in the presence of organic solvent, wherein the organic solvent is isopropanol, ethanol or methanol.
56. The method of claim 7, further comprising 1,3-diaminopropane or ethylenediamine.
57. A compound of formula (VI):
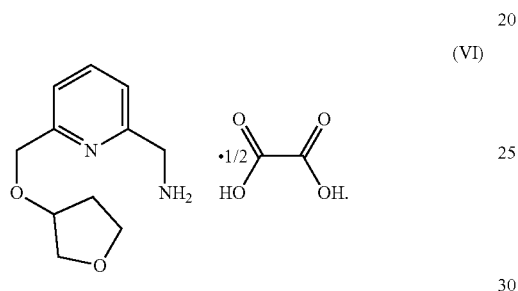
(VI)
* * * * *